US007446222B2

(12) United States Patent
Bit et al.

(10) Patent No.: US 7,446,222 B2
(45) Date of Patent: Nov. 4, 2008

(54) PHENYL COMPOUNDS

(75) Inventors: Rino Antonio Bit, Harlow (GB); Gerard Martin Paul Giblin, Harlow (GB); Adrian Hall, Harlow (GB); David Nigel Hurst, Harlow (GB); Ian Reginald Kilford, Harlow (GB); Neil Derek Miller, Harlow (GB); Tiziana Scoccitti, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 153 days.

(21) Appl. No.: 10/533,036

(22) PCT Filed: Oct. 30, 2003

(86) PCT No.: PCT/EP03/12181

§ 371 (c)(1),
(2), (4) Date: Jan. 18, 2006

(87) PCT Pub. No.: WO2004/039753

PCT Pub. Date: May 13, 2004

(65) Prior Publication Data

US 2006/0235057 A1 Oct. 19, 2006

(30) Foreign Application Priority Data

Nov. 1, 2002 (GB) .................................. 0225548.7

(51) Int. Cl.
*C07C 63/331* (2006.01)
*C07C 63/33* (2006.01)
*C07C 233/54* (2006.01)
*C07C 229/64* (2006.01)
*C07D 257/06* (2006.01)
*C07D 213/30* (2006.01)

(52) U.S. Cl. ........................... 562/469; 560/10; 560/56; 562/426; 562/427; 562/466

(58) Field of Classification Search .................. None
See application file for complete search history.

(56) References Cited

U.S. PATENT DOCUMENTS

| 5,219,856 A | 6/1993 | Olson |
| 5,232,945 A | 8/1993 | Hulin |
| 5,344,991 A | 9/1994 | Reitz et al. |
| 5,420,287 A | 5/1995 | Reitz et al. |
| 5,424,450 A | 6/1995 | Boswell et al. |
| 5,470,975 A | 11/1995 | Atwal |
| 5,474,995 A | 12/1995 | Ducharme et al. |
| 5,512,681 A | 4/1996 | Boswell et al. |
| 5,563,128 A | 10/1996 | Pauls et al. |
| 5,663,180 A | 9/1997 | Reitz et al. |
| 5,723,483 A | 3/1998 | Labeeuw et al. |
| 5,807,896 A | 9/1998 | Gericke et al. |
| 5,811,459 A | 9/1998 | Oldfield et al. |
| 5,840,746 A | 11/1998 | Ducharme et al. |
| 5,972,986 A | 10/1999 | Seibert et al. |
| 6,048,859 A | 4/2000 | Dorn et al. |
| 6,066,766 A | 5/2000 | Haber et al. |
| 6,136,839 A | 10/2000 | Isakson et al. |
| 6,440,963 B1 | 8/2002 | Leonardi et al. |
| 6,451,843 B1 | 9/2002 | Lieb et al. |
| 6,458,965 B1 | 10/2002 | Lieb et al. |
| 6,492,411 B1 | 12/2002 | Talley et al. |
| 6,495,149 B1 | 12/2002 | Scavone et al. |
| 7,232,821 B2 | 6/2007 | Giblin et al. |
| 2001/0020100 A1 | 9/2001 | Manning et al. |
| 2001/0047024 A1 | 11/2001 | Seibert et al. |
| 2002/0045605 A1 | 4/2002 | Kargman et al. |
| 2002/0095041 A1 | 7/2002 | Chan et al. |
| 2002/0107276 A1 | 8/2002 | Isakson et al. |
| 2003/0073844 A1 | 4/2003 | Ku et al. |

FOREIGN PATENT DOCUMENTS

| AU | 8311483 | 3/1982 |
| BE | 611179 | 12/1960 |
| DE | 2405171 | 2/1973 |
| DE | 4032522 | 4/1992 |
| DE | 4034728 | 5/1992 |
| DE | 4407488 | 9/1995 |
| DE | 19612101 | 10/1997 |
| DE | 20211496 | 11/2002 |
| EP | 52300 | 11/1980 |
| EP | 131302 | 1/1985 |

(Continued)

OTHER PUBLICATIONS

Ahmad, et al. "Prostaglandin EP1 Receptor Contributes to Excitotoxicity and Focal Ischemic Brain Damage." Toxicological Sciences, Oct. 19, 2005, 89(1), pp. 265-270.
Blank, B., et al. "Synthesis of Biphenyl Portion of Decinine." Journal of Chemical and Engineering Data, vol. 16, No. 2, 1971, pp. 254-257.
Karig Gunter; Directed Deprotonation-Transmetalation as a Route to substutited Pyridines; Organ Letters, 2001; 3(6); pp. 835-838.

(Continued)

*Primary Examiner*—James O. Wilson
*Assistant Examiner*—Yevgeny Valenrod
(74) *Attorney, Agent, or Firm*—R. Steve Thomas

(57) ABSTRACT

Compounds of formula (I) or derivatives thereof:

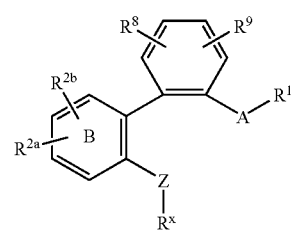

(I)

wherein A, B, Z, $R^1$, $R^{2a}$, $R^{2b}$, $R^x$, $R^8$, and $R^9$ are as defined in the specification, a process for the preparation of such compounds, pharmaceutical compositions comprising such compounds and the use of such compounds in medicine.

9 Claims, No Drawings

FOREIGN PATENT DOCUMENTS

| | | |
|---|---|---|
| EP | 0470794 | 2/1992 |
| EP | 499415 | 8/1992 |
| EP | 499416 | 8/1992 |
| EP | 540009 | 5/1993 |
| EP | 0647629 | 4/1995 |
| EP | 706795 | 4/1996 |
| EP | 0752421 | 1/1997 |
| EP | 0799823 | 10/1997 |
| EP | 733366 | 4/1998 |
| EP | 707007 | 12/2001 |
| EP | 1251126 | 10/2002 |
| EP | 1264847 | 12/2002 |
| EP | 1270559 | 1/2003 |
| EP | 1312605 | 5/2003 |
| GB | 2272899 | 6/1994 |
| JP | 04076087 | 3/1992 |
| JP | 04235933 | 8/1992 |
| JP | 05224442 | 9/1993 |
| JP | 06065213 | 3/1994 |
| JP | 2002275064 | 9/2002 |
| JP | 2002363748 | 12/2002 |
| JP | 2003192659 | 7/2003 |
| NE | 6610022 | 8/1965 |
| WO | WO 91/15479 | 10/1991 |
| WO | WO 92/02257 | 2/1992 |
| WO | WO 92/20642 | 11/1992 |
| WO | WO 93/04045 | 3/1993 |
| WO | WO 93/04046 | 3/1993 |
| WO | WO 94/05658 | 3/1994 |
| WO | WO 95/00501 | 1/1995 |
| WO | WO 95/05372 | 2/1995 |
| WO | WO 95/11883 | 5/1995 |
| WO | WO 95/17393 | 6/1995 |
| WO | WO 95/26724 | 10/1995 |
| WO | WO 95/27692 | 10/1995 |
| WO | WO 96/10012 | 4/1996 |
| WO | WO 96/11676 | 4/1996 |
| WO | WO 96/11902 | 4/1996 |
| WO | WO 96/16934 | 6/1996 |
| WO | WO 96/36623 | 11/1996 |
| WO | WO 96/37496 | 11/1996 |
| WO | WO 96/41645 | 12/1996 |
| WO | WO 97/03667 | 2/1997 |
| WO | WO 97/05131 | 2/1997 |
| WO | WO 97/11701 | 4/1997 |
| WO | WO 97/16435 | 5/1997 |
| WO | WO 97/29748 | 8/1997 |
| WO | WO 97/38986 | 10/1997 |
| WO | WO 98/16227 | 4/1998 |
| WO | WO 98/25896 | 6/1998 |
| WO | WO 98/28257 | 7/1998 |
| WO | WO 98/55468 | 12/1998 |
| WO | WO 99/17776 | 4/1999 |
| WO | WO 99/58487 | 11/1999 |
| WO | WO 00/02887 | 1/2000 |
| WO | WO 00/47553 | 8/2000 |
| WO | WO 00/53149 | 9/2000 |
| WO | WO 00/59506 | 10/2000 |
| WO | WO 00/76489 | 12/2000 |
| WO | WO 01/19814 | 3/2001 |
| WO | WO 01/21582 | 3/2001 |
| WO | WO 01/55146 | 8/2001 |
| WO | WO 01/64646 | 9/2001 |
| WO | WO 01/81332 | 11/2001 |
| WO | WO 02/12210 | 2/2002 |
| WO | WO 02/20004 | 3/2002 |
| WO | WO 02/50002 | 6/2002 |
| WO | WO 02/099435 | 12/2002 |
| WO | WO 02/100838 | 12/2002 |
| WO | WO 03/002548 | 1/2003 |
| WO | WO 03/006628 | 1/2003 |
| WO | WO 03/010145 | 2/2003 |
| WO | WO 03/020790 | 3/2003 |
| WO | WO 03/045552 | 6/2003 |
| WO | WO 03/048257 | 6/2003 |
| WO | WO 03/051860 | 6/2003 |
| WO | WO 03/053927 | 7/2003 |
| WO | WO 03/084917 | 10/2003 |
| WO | WO 03/101959 | 12/2003 |
| WO | WO 2004/039753 | 5/2004 |
| WO | WO 2004/083185 | 9/2004 |

OTHER PUBLICATIONS

Hori, M., et al. "Dibenzothiophenes and Related Compounds. III. 1,2) Reactions of 10-Substituted 9,9-Dimethylthioxanthenium and 5-Substituted Dibenzothiophenium Salts with Organolithiums." Chemical & Pharmaceutical Bulletin (1974), 22(9), pp. 2004-2013.

Kawahara, et al. "A Prostaglandin E2 Receptor Subtype EP1 Receptor Antagonist (ONO-8711) Reduces Hyperalgesia, Allodynia, and C-fos Gene Expression in Rats with Chronic Nerve Constriction." Anesth Analg. 2001, 93, pp. 1012-1017.

Kawano, et al. "Prostaglandin E2 EP1 Receptors: Downstream Effectors of Cox-2 Neurotoxicity." Nature Medicine, Feb. 2006, 12(2), pp. 225-229.

Lacombe, P., et al. "2,3-Diarylthiophene as potent ligands for the human EP1 prostanoid receptor." Abstracts of Papers American Chemical Society, vol. 220, No. Part 1, 2000, pp. MED1 246.

Malik, O.P., et al. "Studies on Cannabinoids: Part III. Synthesis of 9,10,11,11a-Tetrahydro-6H,8H-Pyrido(1,2-c][1,3]benzoxazine." Indian Journal of Chemistry, Section B: Organic Chemistry Including Medicinal Chemistry, 1976, 14B(12), pp. 975-978.

Omote, et al. "The Effects of Intrathecal Administration of an Antagonist for Prostaglandin E Receptor Subtype EP1 on Mechanical and Thermal Hyperalgesia in a Rat Model of Postoperative Pain." Anesth Analg. 2002, 95, pp. 1708-1712.

Omote, et al.. "The Effects of Peripheral Administration of a Novel Selective Antagonist for Prostaglandin E Receptor Subtype EP1, ONO-8711, in a Rat Model of Postoperative Pain." Anesth Analg., 2001, 92, pp. 233-238.

Panthan et al. "2-Aryl-3-(2'-p-Chlorophenyl-1',3'4'-Oxadiazol-5'-Phenyl)-4-Thiazolidinones." Journal of the Institution of Chemists (India): 72(5), pp. 190-191.

Panthan MD, et al. 514183; Chemical Abstracts Services; 2001.

Rahim Abdur M et al. Isometric acetoxy analogues of rofecoxib: A novel class of highly potent and selective cyclooxygenase-2 inhibitors; Bioorganic and Medicinal Chemistry Letters, 2001, 12(19), pp. 2753-2756.

Rathore, R., et al. "Efficient Hydrogenation of Sterically Hindered Olefins with Borane-Methyl Sulfide Complex." Journal of Organic Chemistry, 1996, 61(16), pp. 5246-5256.

Rebstock Anne-Sophie. Synthesis and deprotonation of 2-(pyridyl)phenosis and 2-(pyridyl)amilines, Organic and Biomolecular Chemistry, 2003, 17, pp. 3064-3068.

Rosenberg Saul H et al. Convergent and efficient synthesis of spiro[benzofuran-3(2H),4'piperidines]; Journal of Organic Chemistry, 1984, 49(1), pp. 56-62.

Sarkar, et al.. "The Prostaglandin E2 Receptor-1 (EP1) Mediates Acid-Induced Visceral Pain Hypersensitivity in Humans." Gastroenterology, 2003, 124, pp. 18-25.

Stock, et al.. "The Prostaglandin E2 EP1 Receptor Mediates Pain Perception and Regulates Blood Pressure." The Journal of Clinical Investigation, Feb. 2001, 107(3), pp. 325-331.

Stoyanovich, F.M., et al. "Reactions of Arylsulfonyl Compounds with An Excess of Organolithium Reagent. 11. Polar Addition to 3-Lithioarynes and Synthesis of 2-Substituted Isophthalic Acids." Izv. Akad. Nauk SSSR, Ser. Khim (1978), 142-150. (English Abstract Only).

Synergistic Mixtures of Strobilurin and Pyrimidine Analogs. Research Disclosure, Dec. 1995, pp. 823-824.

Trivedit GS et al. "Synthesis and Antimicrobial Activity of Some 4-Thiazolidinones." Indian Journal of Chemistry, 1992, 31B, pp. 366-369.

Whitesell, J.K., et al. "Synthesis and Resolution of a New Chiral C2-Symmetric Bisphenol: Trans-1,2-Bis(2-Hydroxyphenyl)cyclopentane." Tetrahedron Letters, 1997, 38(15), pp. 2589-2592.

Imai, Y., et al. "Novel axial chiral sulfur-oxazoline ligands with a biphenyl backbone." Synlett, No. 8, 1999, pp. 1319-1321.

Baker, R.W., et al. Formal synthesis of both atropisomers of desertorin C and an example of chirality transfer from a biphenyl axis to a spiro center and its reverse. Australian Journal of Chemistry, vol. 53, No. 6, 2000, pp. 487-506.

Rippert, A.J. "New axially chiral bis(dihydrooxazoles) as ligands in steroselective transition-metal catalysis." Helvetica Chimica ACTA, vol. 81, No. 4, 1998, pp. 676-687.

Fuson, R.C., et al. "Synthesis of 2-iodo-2'-methoxybiphenyl. A new route to .omicron.-terphenyls." Journal of American Chemical Society, vol. 81, 1959, pp. 87-490.

Fuson, R.C., et al. "Reaction of o-methoxyphenylmagnesium bromide with hindered ketones." Journal of Organic Chemistry, vol. 27, 1962, pp. 1578-1581.

Moorlag, H., et al. "An asymmetric synthesis of a C2 symmetric tetrasubstituted biaryl: 2,2'-dihydroxy-6,6'-dimethyl,1,1'-biphenyl, a stable chiral system." Tetrahedron Letters, vol. 34, No. 44, 1993, pp. 6993-6996.

Moorlag, H., et al. "Oxazoline-mediated biaryl coupling reactions. Stereocontrolled synthesis of 2,2,'6,6-tetrasubstituted biphenyls." Tetrahedron Letters, vol. 34, No. 44, 1993, pp. 6989-6992.

Baker, R.W., et al. "Chirality transfer from a piphenyl axis to a spiro center and its reverse sequential self-immolation." Tetrahedron Letters, vol. 40, No. 17, 1999, pp. 3475-3478.

PHENYL COMPOUNDS

This application is filed pursuant to 35 U.S.C. §371 as a United States National Phase Application of International Application No. PCT/EP2003/012181, filed 30 Oct. 2003, which claims priority to Great Britain Priority Patent Application Serial No. 0225548.7, filed 1 Nov. 2002.

This invention relates to phenyl derivatives, to processes for their preparation, to pharmaceutical compositions containing them and to their use in medicine, in particular their use in the treatment of conditions mediated by the action of $PGE_2$ at the $EP_1$ receptor.

The $EP_1$ receptor is a 7-transmembrane receptor and its natural ligand is the prostaglandin $PGE_2$. $PGE_2$ also has affinity for the other EP receptors (types $EP_2$, $EP_3$ and $EP_4$). The $EP_1$ receptor is associated with smooth muscle contraction, pain (in particular inflammatory, neuropathic and visceral), inflammation, allergic activities, renal regulation and gastric or enteric mucus secretion. We have now found a novel group of compounds which bind with high affinity to the $EP_1$ receptor.

A number of review articles describe the characterization and therapeutic relevance of the prostanoid receptors as well as the most commonly used selective agonists and antagonists: *Eicosanoids; From Biotechnology to Therapeutic Applications*, Folco, Samuelsson, Maclouf, and Velo eds, Plenum Press, New York, 1996, chap. 14, 137-154 and Journal of Lipid Mediators and Cell Signalling, 1996, 14, 83-87 and *Prostanoid Receptors, Structure, Properties and Function*, S Narumiya et al, Physiological Reviews 1999, 79(4), 1193-126. An article from *The British Journal of Pharmacology* (1994, 112, 735-740) suggests that Prostaglandin $E_2$ ($PGE_2$) exerts allodynia through the $EP_1$ receptor subtype and hyperalgesia through $EP_2$ and $EP_3$ receptors in the mouse spinal cord. Furthermore an article from *The Journal of Clinical Investigation* (2001, 107 (3), 325) shows that in the $EP_1$ knock-out mouse pain-sensitivity responses are reduced by approximately 50%. Two papers from *Anesthesia and Analgesia* have shown that (2001, 93, 1012-7) an $EP_1$ receptor antagonist (ONO-8711) reduces hyperalgesia and allodynia in a rat model of chronic constriction injury, and that (2001, 92, 233-238) the same antagonist inhibits mechanical hyperalgesia in a rodent model of post-operative pain. S. Sarkar et al in *Gastroenterology*, 2003, 124(1), 18-25 demonstrate the efficacy of $EP_1$ receptor antagonists in the treatment of visceral pain in a human model of hypersensitivity. Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, inhibit hormone-induced uterine contractions and have anti-cancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced effect on bleeding times and a lessened ability to induce asthma attacks in aspirin-sensitive asthmatic subjects. Moreover, by sparing potentially beneficial prostaglandin pathways, these agents may have enhanced efficacy over NSAIDS and/or COX-2 inhibitors.

In The American Physiological Society (1994, 267, R289R-294), studies suggest that $PGE_2$-induced hyperthermia in the rat is mediated predominantly through the $EP_1$ receptor. WO 96/06822 (Mar. 7, 1996), WO 96/11902 (Apr. 25, 1996), EP 752421-A1 (Jan. 08, 1997) and WO 01/19814 (22 Mar. 2001) disclose compounds as being useful in the treatment of prostaglandin mediated diseases.

P. Lacombe et al (220th National Meeting of The American Chemical Society, Washington D.C., USA, 20-24 Aug. 2000) disclosed 2,3-diarylthiophenes as potent ligands for the human $EP_1$ prostanoid receptor. By way of comparison the terphenyl compound 2-benzyloxy[1,1';2',1"]terphenyl-4"-carboxylic acid was also disclosed, but the presented data suggested that this terphenyl compound was less potent and less selective than the comparable 2,3-diarylthiophene compound.

It is now suggested that a novel group of phenyl derivatives surprisingly are selective for the $EP_1$ receptor over the $EP_3$ receptor, and are therefore indicated to be useful in treating conditions mediated by the action of $PGE_2$ at $EP_1$ receptors. Such conditions include pain, or inflammatory, immunological, bone, neurodegenerative or renal disorders.

Accordingly the present invention provides a compound of formula (I):

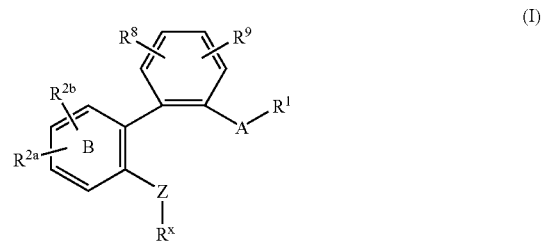

wherein:
A represents an optionally substituted aryl, or an optionally substituted 5- or 6-membered heterocyclyl ring, or an optionally substituted bicyclic heterocyclyl group;
B represents a phenyl or pyridyl ring;
Z represents O, S, SO, or $SO_2$;
$R^1$ represents $CO_2R^4$, CN, $CONR^5R^6$, $CH_2CO_2R^4$, optionally substituted alkyl, optionally substituted alkenyl, optionally substituted $SO_2$alkyl, $SO_2NR^5R^6$, $NR^5CONR^5R^6$, COalkyl, 2H-tetrazol-5-yl-methyl, optionally substituted bicyclic heterocycle or optionally substituted heterocyclyl;
$R^{2a}$ and $R^{2b}$ independently represents hydrogen, halogen, optionally substituted alkyl, optionally substituted alkoxy, CN, $SO_2$alkyl, $SR^5$, $NO_2$, optionally substituted aryl, $CONR^5R^6$ or optionally substituted heteroaryl;
$R^x$ represents optionally substituted alkyl wherein 1 or 2 of the non-terminal carbon atoms are optionally replaced by a group independently selected from $NR^4$, O and $SO_n$, wherein n is 0, 1 or 2: or $R^x$ represents optionally substituted $CQ^aQ^b$-heterocyclyl, optionally substituted $CQ^aQ^b$-bicyclic heterocyclyl or optionally substituted $CQ^aQ^b$-aryl;
$R^4$ represents hydrogen or an optionally substituted alkyl;
$R^5$ represents hydrogen or an optionally substituted alkyl;
$R^6$ represents hydrogen or optionally substituted alkyl, optionally substituted heteroaryl, optionally substituted $SO_2$aryl, optionally substituted $SO_2$alkyl, optionally substituted $SO_2$heteroaryl, CN, optionally substituted $CQ^aQ^b$aryl, optionally substituted $CQ^aQ^b$heteroaryl or $COR^7$;
$R^7$ represents hydrogen, optionally substituted alkyl, optionally substituted heteroaryl or optionally substituted aryl;
$R^8$ and $R^9$ independently represent hydrogen, chloro, fluoro, $CF_3$, $C_{1-3}$alkoxy or $C_{1-3}$alkyl;

$Q^a$ and $Q^b$ are independently selected from hydrogen and $CH_3$;

wherein when A is a 6-membered ring the $R^1$ substituent and phenyl ring are attached to carbon atoms 1,2-, 1,3- or 1,4-relative to each other, and when A is a five-membered ring or bicyclic heterocyclyl group the $R^1$ substituent and phenyl ring are attached to substitutable carbon atoms 1,2- or 1,3-relative to each other;

and derivatives thereof;

provided that the compound is not 2-benzyloxy[1,1';2',1'']terphenyl-4''-carboxylic acid.

Preferably when A is a 6-membered ring, the $R^1$ substituent and phenyl ring are attached to carbon atoms 1,2-, or 1,3- relative to each other.

Suitably A includes phenyl, naphthyl, pyridyl, pyridazinyl, pyrazinyl or pyrimidinyl, all of which may be optionally substituted. Preferably A is phenyl, pyridyl or pyrazinyl, all of which may be optionally substituted. More preferably A is optionally substituted pyridyl or optionally substituted pyrazinyl.

Optional substituents for A include up to four substituents, preferably 0 or 1 substituent, independently selected from halogen, CN, optionally substituted $CO_2C_{1-6}$alkyl, $CONR^5R^6$, $NR^5R^6$, optionally substituted $NR^5COC_{1-6}$alkyl, optionally substituted $NR^5CO$phenyl, optionally substituted $NR^5CO$piperidinyl, optionally substituted $NR^5CO$heterocyclyl, optionally substituted $NR^5SO_2C_{1-6}$alkyl, OH, optionally substituted $OC_{1-6}$alkyl, optionally substituted $C_{1-6}$alkyl and $NR^{10}R^{11}$ wherein $R^{10}$ and $R^{11}$ together with the nitrogen atom to which they are attached form a morpholine ring, a 5- or 6-membered lactam ring or a 5- or 6-membered cyclic sulphonamide, wherein $R^5$ and $R^6$ are as defined above for compounds of formula (I).

Suitably optional substituents for A include halogen, CN, $CO_2C_{1-4}$alkyl, $CONR^5R^6$, $NR^5R^6$, $NR^5COC_{1-4}$alkyl optionally substituted by $NH_2$, phenyl, thienyl, $OC_{1-4}$alkyl or $OCH_2$phenyl, $NR^5CO$phenyl, optionally substituted $NR^5CO$piperidinyl, e.g. NHCO-1-acetylpiperidinyl, NHCO-dimethylisoxazolyl, $NR^5SO_2C_{1-4}$alkyl, $OC_{1-4}$alkyl, $C_{1-4}$alkyl and 2-oxopyrrolidinyl, wherein $R^5$ and $R^6$ are as defined above for compounds of formula (I).

Preferred optional substituents for A include F, Cl, CN, $CO^2C_{1-4}$alkyl, $CONH_2$, $CONHC_{1-4}$alkyl, $CONHCH_2CH_2OH$, $CONHCH_2$pyridyl, $NH_2$, $NHCOC_{1-4}$alkyl, $NHCOCH_2NH_2$, NHCOphenyl, NHCO-dimethylisoxazolyl, NHCO-1-acetylpiperidinyl, $NHCOCH_2OCH_2$phenyl, $NHCOCH_2$phenyl, $NHCOCH_2OC_{1-4}$alkyl, $NHCOCH_2$thienyl, $NHSO_2C_{1-4}$alkyl, $OC_{1-4}$alkyl, $C_{1-4}$alkyl, and 2-oxopyrrolidinyl.

In an alternative aspect optional substituents for A when a phenyl group include up to four substituents, preferably 0 or 1 substituent, independently selected from halogen, $NR^5R^6$, $NR^5COC_{1-6}$alkyl, $NR^5SO_2C_{1-6}$alkyl, $OR^5$, $C_{1-6}$alkyl and $NR^{10}R^{11}$ wherein $R^{10}$ and $R^{11}$ together with the nitrogen atom to which they are attached form a morpholine ring, a 5- or 6-membered lactam ring or a 5 or 6-membered cyclic sulphonamide, wherein $R^5$ and $R^6$ are as defined above for compounds of formula (I). Alternative optional substituents for A are selected from halogen, $NR^5R^6$, $NHCOC_{1-6}$alkyl, $NHSO_2C_{1-6}$alkyl, $C_{1-6}$-alkyl and $NR^{10}R^{11}$.

Optional substituents for A when a 5 or 6-membered heterocyclyl group include $NH_2$. When A is pyridyl it may be substituted on the ring nitrogen by an oxygen to give a pyridine N-oxide.

When B is pyridyl, preferably the pyridine N atom is positioned 1,2-relative to the ring carbon carrying either the phenyl or Z substituent.

n a preferred aspect at least one of the A and B rings contain a nitrogen atom.

Suitably Z is O.

Suitably $R^1$ includes $CO_2H$, optionally substituted $CONHSO_2$aryl, $CH_2CO_2H$, $SO_2NHCOR^7$, $SO_2NHCOC_{1-6}$alkyl or tetrazolyl. Preferably $R^1$ includes $CO_2H$, $CONHSO_2$phenyl, $CONHSO_2$(4-nitrophenyl), $CH_2CO_2H$, $SO_2NHCO$phenyl, $SO_2NHCOC_{1-4}$alkyl or tetrazolyl.

Alternatively $R^1$ includes $CO_2R^4$, $CONHSO_2$aryl, $CH_2CO_2R^4$, $SO_2NHCOR^7$, $SO_2NHCOC_{1-6}$alkyl or tetrazolyl.

Preferably $R^1$ represents $CO_2H$.

Preferably $R^{2a}$ is hydrogen.

Preferably $R^{2b}$ represents hydrogen, halogen, $CF_3$, optionally substituted $C_{1-6}$alkyl, CN or $SO_2C_{1-6}$alkyl, more preferably $R^{2b}$ represents hydrogen, halogen, or $CF_3$.

Preferably $R^{2b}$ is positioned 1,4-relative to the Z substituent and 1,3-relative to the phenyl ring.

Suitably $R^x$ includes optionally substituted $C_{1-8}$alkyl, optionally substituted $CH_2$phenyl, $CH_2$pyridyl, or $CH_2$thienyl. Preferably $R^x$ represents $C_{1-8}$-alkyl, optionally substituted $CH_2$phenyl or $CH_2$thienyl, most preferably $R^x$ represents $C_{1-8}$alkyl or optionally substituted $CH_2$phenyl.

Suitably optional substituents for $R^x$ when $CH_2$phenyl include one to three substituents selected from Cl, F, Br, and $CF_3$. Particular examples include Cl and F.

When $R^x$ is $C_{1-8}$alkyl examples include propyl, isopropyl, n-butyl, iso-butyl, sec-butyl, 3-methylbutyl, cyclopentylmethyl and cyclohexylmethyl.

Suitably $R^4$ includes hydrogen and $C_{1-6}$alkyl. Preferably $R^4$ is hydrogen.

Suitably $R^5$ includes hydrogen and $C_{1-6}$alkyl. Preferably $R^5$ is selected from hydrogen and $C_{1-3}$alkyl.

Suitably $R^6$ includes hydrogen, $C_{1-6}$alkyl optionally substituted by phenyl, thienyl, pyridyl, or OH, $SO_2$phenyl and $COR^7$.

Suitably $R^7$ includes hydrogen, phenyl and $C_{1-6}$alkyl.

Suitably $R^8$ and $R^9$ include hydrogen, chloro, fluoro, $CF_3$, $OCH_3$ and $CH_3$. In one alternative $R^8$ and $R^9$ are each hydrogen.

An example of $Q^a$ is hydrogen.

An example of $Q^b$ is hydrogen.

In one aspect the present invention provides a compound of formula (Ia):

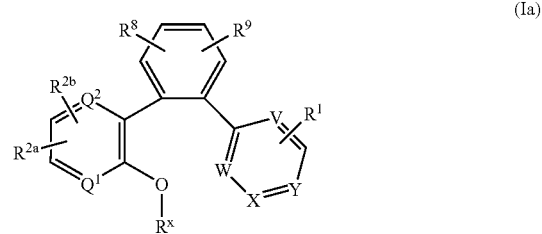

wherein:

W, X, and Y each represents $CR^{12}$ or N;

V represents $CR^1$, $CR^{12}$ or N;

wherein at least two of W, X, Y or V is $CR^{12}$; and $R^{12}$ is independently selected from hydrogen, halogen, CN, optionally substituted $CO_2C_{1-6}$alkyl, $CONR^5R^6$, $NR^5R^6$, optionally substituted $NR^5COC_{1-6}$alkyl, optionally substituted $NR^5CO$phenyl, optionally substituted $NR^5CO$piperidinyl, optionally substituted $NR^5CO$heterocyclyl, optionally substituted $NR^5SO_2C_{1-6}$ alkyl, OH, optionally substituted $OC_{1-6}$alkyl, optionally substituted $C_{1-6}$alkyl and $NR^{10}R^{11}$;

$Q^1$ and $Q^2$ each represents CH, or one of $Q^1$ and $Q^2$ is N and the other is CH;

$R^1$ is $CO_2H$, optionally substituted $CONHSO_2$aryl, $CH_2CO_2H$, $SO_2NHCOR^7$, $SO_2NHCOC_{1-6}$alkyl or tetrazolyl and is positioned 1,2-, or 1,3-relative to the phenyl ring;

$R^{2a}$ and $R^{2b}$ are independently selected from hydrogen, halo, or $CF_3$;

$R^x$ represents optionally substituted $C_{1-8}$alkyl, or $R^x$ represents optionally substituted $CQ^aQ^b$-heterocyclyl or optionally substituted $CQ^aQ^b$-phenyl wherein $Q^a$ and $Q^b$ are independently selected from hydrogen and $CH_3$;

$R^4$ represents hydrogen or an optionally substituted $C_{1-6}$alkyl;

$R^5$ represents hydrogen or an optionally substituted $C_{1-6}$alkyl;

$R^6$ represents hydrogen or an optionally substituted $C_{1-6}$alkyl, optionally substituted $SO_2$phenyl, optionally substituted $SO_2$heterocyclyl group, CN, optionally substituted $CH_2$phenyl or $COR^7$;

$R^7$ represents hydrogen, optionally substituted heteroaryl or optionally substituted phenyl;

$R^8$ and $R^9$ independently represent hydrogen, chloro, fluoro, $CF_3$, $C_{1-3}$alkoxy or $C_{1-3}$alkyl; and $R^{10}$ and $R^{11}$ together with the nitrogen atom to which they are attached form a morpholine ring, a 5- or 6-membered lactam ring or a 5- or 6-membered cyclic sulphonamide, and derivatives thereof.

Suitably $R^x$ includes $C_{1-8}$alkyl, $CH_2$thienyl or $CH_2$phenyl optionally substituted by one, two or three substituents selected from $CF_3$ and halogen, e.g. Br, Cl and F.

In one aspect $R^1$ is positioned 1,3-relative to the phenyl ring.

In another aspect at least one of W, X, Y and V is N.

In yet another aspect one of $Q^1$ and $Q^2$ is N.

A particular set of compounds are those wherein one or two of W, X, Y and V is N and $Q^1$ and $Q^2$ are both CH; or one of $Q^1$ and $Q^2$ is N and W, X, Y, and V are each $CR^{12}$.

Preferably $Q^1$ is N or CH and $Q^2$ is CH.

Suitably $R^{12}$ includes hydrogen, halogen, CN, $CO_2C_{1-4}$alkyl, $CONR^5R^6$, $NR^5R^6$, $NR^5COC_{1-4}$alkyl optionally substituted by $NH_2$, phenyl, thienyl, $OC_{1-4}$alkyl or $OCH_2$phenyl, $NR^5CO$phenyl, optionally substituted $NR^5CO$piperidinyl, e.g. NHCO-1-acetylpiperidinyl, NHCO-dimethylisoxazolyl, $NR^5SO_2C_{1-4}$alkyl, $OC_{1-4}$alkyl, $C_{1-4}$alkyl and 2-oxopyrrolidinyl, wherein $R^5$ and $R^6$ are as defined above for compounds of formula (I).

Particular examples of $R^{12}$ include hydrogen F, Cl, CN, $CO_2C_{1-4}$alkyl, $CONH_2$, $CONHC_{1-4}$alkyl, $CONHCH_2CH_2OH$, $CONHCH_2$pyridyl, $NH_2$, $NHCOC_{1-4}$alkyl, $NHCOCH_2NH_2$, NHCOphenyl, NHCO-dimethylisoxazolyl, NHCO-1-acetylpiperidinyl, $NHCOCH_2OCH_2$phenyl, $NHCOCH_2$phenyl, $NHCOCH_2OC_{1-4}$alkyl, $NHCOCH_2$thienyl, $NHSO_2C_{1-4}$alkyl, $OC_{1-4}$alkyl, $C_{1-4}$alkyl, and 2-oxopyrrolidinyl.

When one or two of W, X, Y and V is N, examples of $R^{12}$ include hydrogen and $NH_2$.

Preferably $R^{2a}$ is hydrogen.

Preferably $R^{2b}$ is positioned 1,4-relative to $OR^x$ and 1,3-relative to the phenyl ring.

Preferably $R^{2b}$ is selected from F, Cl, Br and $CF_3$.

In one aspect $R^8$ and $R^9$ are both hydrogen.

In an alternative aspect the present invention provides compounds of formula (Ib):

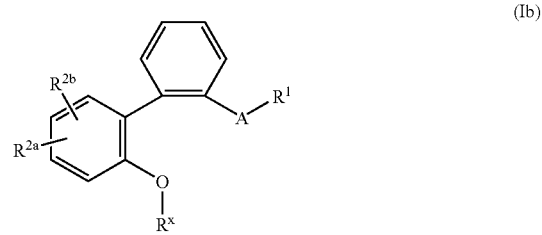

(Ib)

wherein:

A represents optionally substituted phenyl, an optionally substituted 5- or 6-membered heterocyclyl ring or an optionally substituted bicyclic heterocyclyl group;

$R^1$ represents hydrogen, $CO_2R^4$, $CONR^5R^6$, $CH_2CO_2R^4$, optionally substituted $C_{1-6}$alkyl, optionally substituted $C_{1-6}$alkenyl, optionally substituted $SO_2C_{1-6}$alkyl, $SO_2NR^5R^6$, $NR^5CONR^5R^6$, $CONR^5R^6$, 2H-tetrazol-5-yl-methyl or optionally substituted heterocyclyl;

wherein when A is a 6-membered ring the $R^1$ and phenyl group are attached to carbon atoms 1,2-, 1,3- or 1,4-relative to each other, and when A is a five-membered ring or bicyclic heterocyclyl group the $R^1$ and phenyl group are attached to substitutable carbon atoms 1,2- or 1,3-relative to each other;

$R^{2a}$ and $R^{2b}$ independently represent hydrogen, halo, $CF_3$, optionally substituted $C_{1-6}$alkyl, CN, $SO_2R^5$, $NO_2$, optionally substituted aryl, $CONR^5R^6$ or optionally substituted heteroaryl;

$R^x$ represents optionally substituted $C_{1-8}$alkyl wherein 1 or 2 of the non-terminal carbon atoms may optionally be replaced by a group independently selected from $NR^4$, O or $SO_n$, wherein n is 0, 1 or 2; or $R^x$ may be optionally substituted $CQ_2$-heterocyclyl or optionally substituted $CQ_2Ph$ wherein each Q is independently selected from H and $CH_3$;

$R^4$ represents hydrogen or an optionally substituted $C_{1-6}$alkyl;

$R^5$ represents hydrogen or an optionally substituted $C_{1-6}$alkyl;

$R^6$ represents hydrogen, optionally substituted $C_{1-6}$alkyl, optionally substituted $SO_2$aryl, optionally substituted $SO_2$heterocyclyl group, CN or $COR^7$;

$R^7$ represents optionally substituted aryl or heteroaryl;

and derivatives thereof.

In one aspect the derivatives are pharmaceutically acceptable derivatives.

Examples of compounds of formula (Ib) are compounds of formula (Ic):

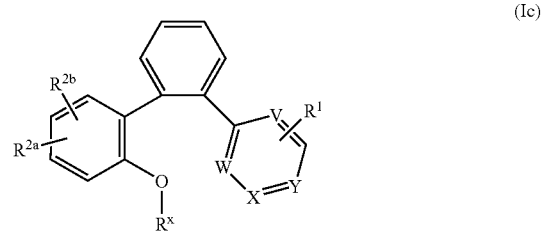

(Ic)

wherein:
$R^1$ is $CO_2R^4$, $CONHSO_2Ph$, $CH_2CO_2R^4$, $SO_2NHCOPh$, $SO_2NHCOC_{1-6}$alkyl or tetrazolyl;
$R^{2a}$ and $R^{2b}$ are independently selected from hydrogen, halo, or $CF_3$;
$R^x$ represents optionally substituted $C_{1-8}$alkyl, or $R^x$ may be optionally substituted $CQ_2$-heterocyclyl or optionally substituted $CQ_2$-phenyl wherein Q is independently selected from hydrogen and $CH_3$;
$R^4$ is hydrogen or an optionally substituted $C_{1-6}$alkyl;
W, X, Y and V represents CH or N wherein at least one of W, X, Y or V is CH;
or derivatives thereof.

In one aspect the derivatives are pharmaceutically acceptable derivatives.

Examples of $R^x$ include $C_{1-8}$alkyl or optionally substituted $CH_2$phenyl.

Preferably $R^4$ is hydrogen.

In another aspect the compounds of formula (I) include compounds of formula (Id):

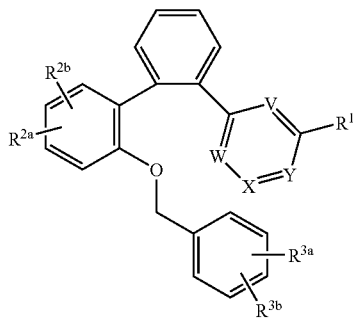

(Id)

$R^1$ is $CO_2R^4$;
$R^{2a}$ and $R^{2b}$ are independently selected from hydrogen, halo, optionally substituted $C_{1-6}$alkyl, $CF_3$, CN or $SO_2C_{1-6}$alkyl;
$R^{3a}$ and $R^{3b}$ are independently selected from hydrogen, halo or optionally substituted $OC_{1-6}$alkyl;
$R^4$ is hydrogen or an optionally substituted $C_{1-6}$alkyl, preferably hydrogen;
W, X, Y and V represents CH or N wherein at least one of W, X, Y or V is CH;

and derivatives thereof.

In one aspect the derivatives are pharmaceutically acceptable derivatives.

In another aspect W, X, Y and V each represents CH.

Preferably $R^{3a}$ and $R^{3b}$ independently represent hydrogen, halo or optionally substituted $O(C_{1-6})$alkyl, more preferably hydrogen or halo.

Examples of the compounds of formula (I) include the compounds of Examples 1 to 90 and derivatives thereof.

In one aspect examples of compounds of formula (I) include:
2-benzyloxy-5-chloro-[1,1';2',1'']terphenyl-3''-carboxylic acid;
(2-benzyloxy-5-chloro-[1,1';2',1'']terphenyl-3''-yl)-acetic acid;
(2-benzyloxy-5-chloro[1,1';2',1'']terphenyl-2''-yl)acetic acid;
(2-benzyloxy-5-chloro[1,1';2',1'']terphenyl-4''-yl)acetic acid;
5''-acetylamino-2-benzyloxy-5-chloro[1,1';2',1'']terphenyl-3''-carboxylic acid;
2-benzyloxy-5-chloro-5''-propionylamino[1,1';2',1'']terphenyl-3''-carboxylic acid;
2-benzyloxy-5-chloro-5''-(2-methylpropanoylamino)-[1,1';2',1'']terphenyl-3''-carboxylic acid;
2-benzoyloxy-5''-butyrylamino-5-chloro[1,1';2',1'']terphenyl-3''-carboxylic acid;
2-benzyloxy-5-chloro-5''-[(1-phenyl-methanoyl)amino]-[1,1';2',1'']terphenyl-3''-carboxylic acid;
2-benzyloxy-5-chloro-5''-methanesulfonylamino-[1,1';2',1''] terphenyl-3''-carboxylic acid
5''-amino-2-benzyloxy-5-chloro[1,1';2',2'']-3''-carboxylic acid;
2-benzyloxy-5''-butyrylamino-5-trifluoromethyl[1,1';2',1''] terphenyl-3''-carboxylic acid-3-carboxylic acid;
2-benzyloxy-4''-chloro[1,1';2',1'']terphenyl 2''-carboxylic acid;
2-benzyloxy-5''-fluoro-[1,1';2',1'']terphenyl-2''-carboxylic acid;
2-benzyloxy-4''-fluoro-[1,1';2',1'']terphenyl-2''-carboxylic acid;
2''-benzyloxy-5-fluoro-[1,1';2',1'']terphenyl-3-carboxylic acid;
4''-amino-2-benzyloxy-[1,1';2',1'']terphenyl-3''-carboxylic acid;
5''-acetylamino-2-benzyloxy-[1,1';2',1'']terphenyl-2''-carboxylic acid;
2-benzyloxy-5-chloro-[1,1';2',1'']terphenyl-2''-carboxylic acid;
2-benzyloxy-[1,1';2',1'']terphenyl-3''-carboxylic acid;
2-benzyloxy-5-chloro-[1,1';2',1'']terphenyl-2''-carboxylic acid amide;
5-(2-benzyloxy-5-chloro-[1,1';2',1'']terphenyl-3''-yl)-1H-tetrazole;
N-[1-(2-benzyloxy-5-chloro-[1,1';2',1'']terphenyl-2''-yl)-methanoyl]-benzenesulfonamide;
2-benzyloxy-[1,1';2',1'']terphenyl-4''-sulfonic acid (1-phenyl-methanoyl)-amide;
2-benzyloxy-[1,1';2',1'']terphenyl-4''-sulfonic acid [1-(4-nitro-phenyl)-methanoyl]-amide;
2-benzyloxy-[1,1';2',1'']terphenyl-3''-sulfonic acid acetylamide;
5-chloro-2-(3-methyl-butoxy)-[1,1';2',1'']terphenyl-3''-carboxylic acid;
5-chloro-2-(4-fluoro-benzyloxy)-[1,1';2',1'']terphenyl-3''-carboxylic acid;
5-chloro-2-(2,4-difluoro-benzyloxy)-[1,1';2',1'']terphenyl-3''-carboxylic acid;
5-chloro-2-(4-chloro-benzyloxy)-[1, 1';2',1'']terphenyl-3''carboxylic acid;
5-chloro-2-(2-fluoro-4-chloro-benzyloxy)-[1,1';2',1'']terphenyl-3''carboxylic;
5-chloro-2-(4-isobutoxy)-[1,1';2',1'']terphenyl-3''-carboxylic acid;
5-chloro-2-(pyridin-2-ylmethoxy)-[1,1';2',1'']terphenyl-3''carboxylic acid;
5-chloro-2-(pyridin-4-ylmethoxy)-[1,1';2',1'']terphenyl-3''carboxylic acid;
5-chloro-2-(pyridin-3-ylmethoxy)-[1,1';2',1'']terphenyl-3''carboxylic acid;
5-chloro-2-cyclohexylmethoxy-[1,1';2',1'']terphenyl-3''carboxylic acid;
5-chloro-2-(thiophen-3-ylmethoxy)-[1,1';2',1'']terphenyl-3''carboxylic acid;
5-chloro-2-(thiophen-2-ylmethoxy)-[1,1';2',1'']terphenyl-3''carboxylic acid;
5-chloro-2-cyclopentylmethoxy-[1,1';2',1'']terphenyl-3''carboxylic acid;

5-chloro-2-propoxy-[1,1';2',1"]terphenyl-3"-carboxylic acid;
2-butoxy-5-chloro-[1,1';2',1"]terphenyl-3"-carboxylic acid;
5-chloro-2-isopropoxy-[1,1';2',1"]terphenyl-3"-carboxylic acid;
5-chloro-2-isobutoxy-[1,1';2',1"]terphenyl-2"-carboxylic acid;

and derivatives thereof.

Further examples of the invention include the compounds of Examples 44 to 90 and derivatives thereof.

Preferred examples include the compounds of Examples 52, 72, 73, 74, 75, 76, 85 and 88 and derivatives thereof.

Preferably compounds are selective for $EP_1$ over $EP_3$. More preferably the compounds are 100 fold selective, more preferably 1000 fold selective for $EP_1$ over $EP_3$.

Derivatives of the compounds of formula (I) include pharmaceutically acceptable derivatives.

The invention is described using the following definitions unless otherwise indicated.

The term "pharmaceutically acceptable derivative" means any pharmaceutically acceptable salt, ester, salt of such ester or solvate of the compounds of formula (I), or any other compound which upon administration to the recipient is capable of providing (directly or indirectly) a compound of formula (I).

It will be appreciated by those skilled in the art that the compounds of formula (I) may be modified to provide pharmaceutically acceptable derivatives thereof at any of the functional groups in the compounds, and that the compounds of formula (I) may be derivatised at more than one position.

It will be appreciated that, for pharmaceutical use, the salts referred to above will be pharmaceutically acceptable salts, but other salts may find use, for example in the preparation of compounds of formula (I) and the pharmaceutically acceptable salts thereof.

Pharmaceutically acceptable salts include those described by Berge, Bighley and Monkhouse, *J. Pharm. Sci.*, 1977, 66, 1-19. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperdine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropyl amine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acid.

Preferred examples of pharmaceutically acceptable salts include those formed from maleic, fumaric, benzoic, ascorbic, pamoic, succinic, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

The terms "halogen or halo" are used to represent fluorine, chlorine, bromine or iodine, more preferably fluorine, chlorine and bromine.

The term "alkyl" as a group or part of a group means a straight, branched or cyclic chain alkyl group or combinations thereof. Unless hereinbefore defined, examples of alkyl include $C_{1-8}$alkyl, for example methyl, ethyl, n-propyl, iso-propyl, n-butyl, sec-butyl, iso-butyl, tert-butyl, pentyl, hexyl, 1,1-dimethylethyl, cyclopentyl or cyclohexyl or combinations thereof.

The term "alkoxy" as a group or as part of a group means a straight, branched or cyclic chain alkyl group having an oxygen atom attached to the chain. Unless hereinbefore defined examples of alkoxy include $C_{1-8}$alkoxy, for example methoxy, ethoxy, n-propoxy, iso-propoxy, n-butoxy, sec-butoxy, iso-butoxy, tert-butoxy, pentoxy, hexyloxy, cyclopentoxy or cyclohexyloxy.

The term "alkenyl" means linear or branched structures and combinations thereof, of the indicated number of carbon atoms, having at least one carbon-to-carbon double bond, wherein hydrogen may be replaced by an additional carbon to carbon double bond. $C_{2-6}$alkenyl, for example, includes ethenyl, propenyl, 1-methylethenyl, butenyl and the like.

The term "heterocyclyl" as a group or as part of a group means an aromatic or non-aromatic five or six membered ring which contains from 1 to 4 heteroatoms selected from nitrogen, oxygen or sulfur and unsubstituted or substituted by, for example, up to three substituents, preferably one or two substituents. Examples of 5-membered heterocyclyl groups include furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl or tetrazolyl. Examples of 6-membered heterocyclyl groups are pyridyl, pyridazinyl, pyrimidinyl, pyrazinyl, triazinyl or tetrazinyl.

The term "bicyclic heterocyclyl" when used herein means a fused bicyclic aromatic or non-aromatic bicyclic heterocyclyl ring system comprising up to four, preferably one or two, heteroatoms each selected from oxygen, nitrogen and sulphur. Each ring may have from 4 to 7, preferably 5 or 6, ring atoms. A bicyclic heteroaromatic ring system may include a carbocyclic ring. Examples of bicyclic heterocyclyl groups include quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl or naphthyridinyl.

The term "aryl" as a group or as part of a group means a 5- or 6-membered aromatic ring for example phenyl, or a 7 to 12 membered bicyclic ring system where at least one of the rings is aromatic, for example naphthyl. An aryl group may be substituted by up to four, preferably one to three substituents. Preferably the aryl group is phenyl.

The term "heteroaryl" as a group or as part of a group means a monocyclic five or six membered aromatic ring, or a fused bicyclic aromatic ring system comprising two of such monocyclic five or six membered aromatic rings. These heteroaryl rings contain one or more heteroatoms selected from nitrogen, oxygen or sulfur, where N-oxides, sulfur oxides and sulfur dioxides are permissible heteroatom substitutions. A heteroaryl group may be optionally substituted by one or more substituents for example one or two substituents. Examples of "heteroaryl" used herein include furyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyrimidinyl, quinolinyl, isoquinolinyl, benzofuryl, benzothienyl, indolyl, and indazolyl.

Optional substituents for alkyl or alkenyl groups unless hereinbefore defined include OH, CO$_2$R$^4$, NR$^4$R$^5$, (O), —OC$_{1-6}$alkyl or halo e.g. Cl, Br or F, wherein R$^4$, and R$^5$ are as hereinbefore defined for compounds of formula (I). An alkyl or alkenyl group may be substituted by one or more optional substituents, for example up to 5, 4, 3, or 2 optional substituents. Particular substituted alkyl groups include those susbituted by one or more fluorine atoms e.g. CH$_2$F, CHF$_2$, CF$_3$, C$_2$F$_5$ etc, especially CF$_3$.

Optional substituents for alkoxy groups unless hereinbefore defined include OH, and halo e.g. Cl, Br or F. An alkoxy group may be substituted by one or more optional substituents, for example up to 5, 4, 3, or 2 optional substituents. Particular substituted alkoxy groups include those subsituted by one or more fluorines e.g. OCH$_2$F, OCHF$_2$, OCF$_3$, OC$_2$F$_5$ etc.

Optional substituents for A, aryl, heteroaryl or heterocyclyl groups, unless hereinbefore defined, include one or two substituents selected from halogen; optionally substituted C$_{1-6}$alkyl; optionally substituted C$_{1-6}$alkoxy; optionally substituted C$_{2-6}$alkenyl; optionally substituted C$_{2-6}$alkynyl; C$_{1-6}$haloalkyl; C$_{1-6}$ haloalkoxy; NO$_2$; CN; NR$^4$R$^5$; CONR$^4$R$^5$; SO$_2$NR$^4$R$^5$; optionally substituted SO$_n$C$_{1-6}$alkyl; optionally substituted NR$^5$(CO)C$_{1-6}$alkyl; NR$^5$(CO)aryl optionally substituted by one or two substituents selected from halo, NR$^4$R$^5$, C$_{1-6}$alkyl, and OC$_{1-6}$alkyl; NR$^5$(CO)heteroaryl optionally substituted by one or two substituents selected from halo, NR$^4$R$^5$, C$_{1-6}$alkyl, and OC$_{1-6}$alkyl; and optionally substituted NR$^5$(SO$_2$)C$_{1-6}$alkyl; wherein n, R$^4$ and R$^5$ are as hereinbefore defined for compounds of formula (I).

Unless otherwise defined, certain optional substituents for A, aryl, heteroaryl or heterocyclyl groups include halogen; C$_{1-6}$alkyl; C$_{1-6}$alkoxy; C$_{2-6}$alkenyl; C$_{2-6}$alkynyl; C$_{1-6}$haloalkyl; C$_{1-6}$haloalkoxy; NO$_2$; CN; NR$^4$R$^5$; CONR$^4$R$^5$; SO$_2$NR$^4$R$^5$; SO$_2$C$_{1-6}$alkyl; NR$^5$(CO)C$_{1-6}$alkyl; NR$^5$(CO)phenyl; and NR$^5$(CO)heteroaryl; wherein R$^4$ and R$^5$ are as hereinbefore defined for compounds of formula (I). Alternative optional substiuents include halogen, C$_{1-6}$alkyl, and C$_{1-6}$alkoxy.

When the heteroatom nitrogen replaces a carbon atom in a C$_{1-8}$alkyl group, or when nitrogen is present in a heteroaryl, heterocyclyl or bicyclic heterocyclyl group the nitrogen atom will, where appropriate be substituted by one or two substituents selected from hydrogen and C$_{1-8}$alkyl, preferably hydrogen and C$_{1-6}$alkyl, more preferably hydrogen.

Compounds of formula (I) can be prepared as set forth in the following scheme and in the examples. The following processes form another aspect of the present invention.

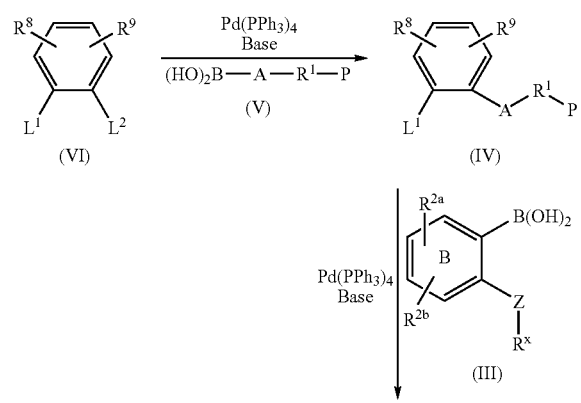

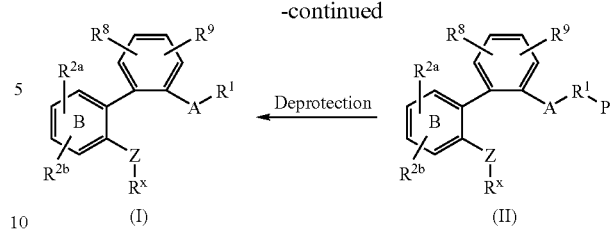

wherein L$^1$ and L$^2$ are each a leaving group for example halo, e.g. bromo; P is an optional protecting group for example methyl, ethyl or benzyl esters; and A, B, R$^{2a}$, R$^{2b}$, Z, R$^8$, R$^9$, R$^1$ and R$^x$ are as defined for compounds of formula (I).

The skilled person will recognise when the use of a protecting group is necessary.

Suitable reaction conditions for the deprotection of a compound of formula (II) include heating in ethanolic sodium hydroxide solution.

Suitable reaction conditions for the reaction of a compound of formula (VI) with a boronic acid of formula (V), or a compound of formula (IV) with a boronic acid of formula (III) include heating with tetrakis(triphenylphosphine)palladium (0) and an inorganic base, for example potassium carbonate or silver carbonate, in a solvent, e.g. ethylene glycol dimethyl ether (DME), toluene and ethanol, preferably in a ratio of 1:1.

Accordingly the present invention also provides a process for the preparation of a compound of formula (I) or a derivative thereof:

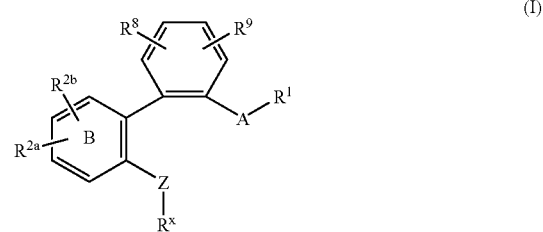

wherein:
A represents an optionally substituted aryl, or an optionally substituted 5- or 6-membered heterocyclyl ring, or an optionally substituted bicyclic heterocyclyl group;
B represents a phenyl or pyridyl ring;
Z represents O, S, SO, or SO$_2$;
R$^1$ represents CO$_2$R$^4$, CN, CONR$^5$R$^6$, CH$_2$CO$_2$R$^4$, optionally substituted alkyl, optionally substituted alkenyl, optionally substituted SO$_2$alkyl, SO$_2$NR$^5$R$^6$, NR$^6$CONR$^5$R$^6$, COalkyl, 2H-tetrazol-5-yl-methyl, optionally substituted bicyclic heterocycle or optionally substituted heterocyclyl;
R$^{2a}$ and R$^{2b}$ independently represents hydrogen, halogen, optionally substituted alkyl, optionally substituted alkoxy, CN, SO$_2$alkyl, SR$^5$, NO$_2$, optionally substituted aryl, CONR$^5$R$^6$ or optionally substituted heteroaryl;
R$^x$ represents optionally substituted alkyl wherein 1 or 2 of the non-terminal carbon atoms are optionally replaced by a group independently selected from NR$^4$, O and SO$_n$, wherein n is 0, 1 or 2: or R$^x$ represents optionally substituted CQ$^a$Q$^b$-heterocyclyl, optionally substituted CQ$^a$Q$^b$-bicyclic heterocyclyl or optionally substituted CQ$^a$Q$^b$-aryl;

$R^4$ represents hydrogen or an optionally substituted alkyl;

$R^5$ represents hydrogen or an optionally substituted alkyl;

$R^6$ represents hydrogen or optionally substituted alkyl, optionally substituted heteroaryl, optionally substituted $SO_2$aryl, optionally substituted $SO_2$alkyl, optionally substituted $SO_2$heteroaryl, CN, optionally substituted $CQ^aQ^b$aryl, optionally substituted $CQ^aQ^b$heteroaryl or $COR^7$;

$R^7$ represents hydrogen, optionally substituted alkyl, optionally substituted heteroaryl or optionally substituted aryl;

$R^8$ and $R^9$ independently represent hydrogen, chloro, fluoro, $CF_3$, $C_{1-3}$alkoxy or $C_{1-3}$alkyl;

$Q^a$ and $Q^b$ are independently selected from hydrogen and $CH_3$;

wherein when A is a 6-membered ring the $R^1$ substituent and phenyl ring are attached to carbon atoms 1,2-, 1,3- or 1,4-relative to each other, and when A is a five-membered ring or bicyclic heterocyclyl group the $R^1$ substituent and phenyl ring are attached to substitutable carbon atoms 1,2- or 1,3-relative to each other;

comprising:

reacting a compound of formula (IV):

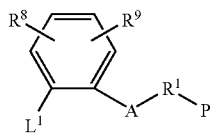

(IV)

wherein $R^8$, $R^9$, A, and $R^1$ are as hereinbefore defined above for a compound of formula (I), $L^1$ is a leaving group and P is an optional protecting group;

with a compound of formula (III):

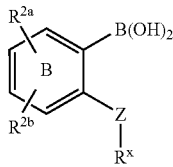

(III)

wherein $R^{2a}$, $R^{2b}$, B, Z, and $R^x$ are as hereinbefore defined above for a compound of formula (I);

and where required, and in any order converting:

one group A to another group A, and/or one group $R^x$ to another group $R^x$:

and where required carrying out the following optional steps in any order:

effecting deprotection; and/or converting one group $R^1$ to another group $R^1$; and/or forming a derivative of the compound of formula (I) so formed.

The present invention also provides a process for the preparation of a compound of formula (Ia) or a derivative thereof:

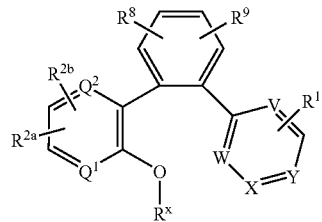

(Ia)

W, X, and Y each represents $CR^{12}$ or N;

V represents $CR^1$, $CR^{12}$ or N;

wherein at least two of W, X, Y or V is $CR^{12}$; and $R^{12}$ is independently selected from hydrogen, halogen, CN, optionally substituted $CO_2C_{1-6}$alkyl, $CONR^5R^6$, $NR^5R^6$, optionally substituted $NR^5COC_{1-6}$alkyl, optionally substituted $NR^5CO$phenyl, optionally substituted $NR^5CO$piperidinyl, optionally substituted $NR^5CO$heterocyclyl, optionally substituted $NR^5SO_2C_{1-6}$alkyl, OH, optionally substituted $OC_{1-6}$alkyl, optionally substituted $C_{1-6}$alkyl and $NR^{10}R^{11}$;

$Q^1$ and $Q^2$ each represents CH, or one of $Q^1$ and $Q^2$ is N and the other is CH;

$R^1$ is $CO_2H$, optionally substituted $CONHSO_2$aryl, $CH_2CO_2H$, $SO_2NHCOR^7$, $SO_2NHCOC_{1-6}$alkyl or tetrazolyl and is positioned 1,2-, or 1,3-relative to the phenyl ring;

$R^{2a}$ and $R^{2b}$ are independently selected from hydrogen, halo, or $CF_3$;

$R^x$ represents optionally substituted $C_{1-8}$alkyl, or $R^x$ represents optionally substituted $CQ^aQ^b$-heterocyclyl or optionally substituted $CQ^aQ^b$-phenyl wherein $Q^a$ and $Q^b$ are independently selected from hydrogen and $CH_3$;

$R^4$ represents hydrogen or an optionally substituted $C_{1-6}$alkyl;

$R^5$ represents hydrogen or an optionally substituted $C_{1-6}$alkyl;

$R^6$ represents hydrogen or an optionally substituted $C_{1-6}$alkyl, optionally substituted $SO_2$phenyl, optionally substituted $SO_2$heterocyclyl group, CN, optionally substituted $CH_2$phenyl or $COR^7$;

$R^7$ represents hydrogen, optionally substituted heteroaryl or optionally substituted phenyl;

$R^8$ and $R^9$ independently represent hydrogen, chloro, fluoro, $CF_3$, $C_{1-3}$alkoxy or $C_{1-3}$alkyl; and $R^{10}$ and $R^{11}$ together with the nitrogen atom to which they are attached form a morpholine ring, a 5- or 6-membered lactam ring or a 5- or 6-membered cyclic sulphonamide, comprising:

reacting a compound of formula (IVa):

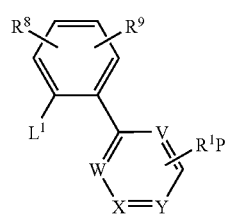

(IVa)

wherein $R^8$, $R^9$, X, Y, V and $R^1$ are as hereinbefore defined above for a compound of formula (I), $L^1$ is a leaving group and P is an optional protecting group;
with a compound of formula (IIIa):

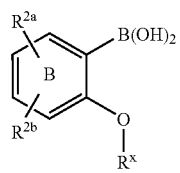

(IIIa)

wherein $R^{2a}$, $R^{2b}$, B, and $R^x$ are as hereinbefore defined above for a compound of formula (I);
and where required, and in any order converting:
one group $R^{12}$ to another group $R^{12}$, and/or
one group $R^x$ to another group $R^x$;
and where required carrying out the following optional steps in any order:
effecting deprotection; and/or
converting one group $R^1$ to another group $R^1$; and/or
forming a derivative of the compound of formula (I) so formed.

Alternatively the compounds of formula (I) may be prepared by the route described below:

compound of formula (VII) with a boronic acid of formula (VIII) include heating with tetrakis(triphenylphosphine)palladium (0) and an inorganic base, for example potassium carbonate or silver carbonate, in a solvent, e.g. ethylene glycol dimethyl ether (DME), toluene and ethanol, preferably in a ratio of 1:1.

Suitable reaction conditions for the conversion of a compound of formula (IX) to a compound of formula (VIII) include reacting the compound of formula (IX) wherein $L^2$ is Br or I with butyl lithium (BuLi) or iso-propyl magnesium chloride in a solvent such as diethyl ether or tetrahydrofuran, treating with trimethyl borate and subsequent acidification.

Accordingly the present invention also provides a process for the preparation of a compound of formula (I) or a derivative thereof:

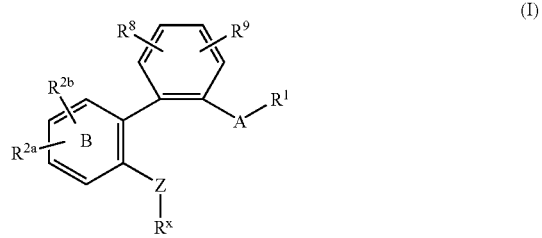

(I)

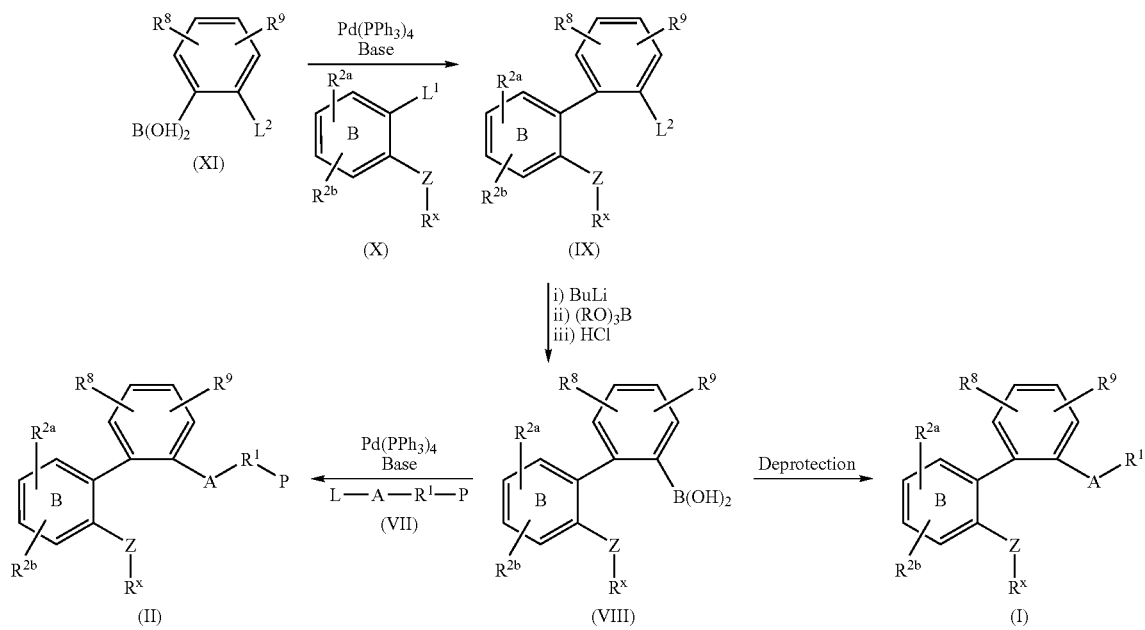

wherein L, $L^1$ and $L^2$ are each a leaving group for example halo, e.g. bromo; P is an optional protecting group, R is $C_{1-4}$ alkyl e.g. methyl or isopropyl, and A, B, $R^{2a}$, $R^{2b}$, Z, $R^8$, $R^9$, $R^1$ and $R^x$ are as defined for compounds of formula (I).

When $R^1$ is $CO_2H$ examples of protecting groups include $C_{1-4}$alkyl, e.g. methyl, ethyl, or benzyl esters.

Suitable reaction conditions for the deprotection of a compound of formula (II) include heating in ethanolic sodium hydroxide solution.

Suitable reaction conditions for the reaction of a compound of formula (X) with a boronic acid of formula (XI), or a wherein:

A represents an optionally substituted aryl, or an optionally substituted 5- or 6-membered heterocyclyl ring, or an optionally substituted bicyclic heterocyclyl group;

B represents a phenyl or pyridyl ring;

Z represents O, S, SO, or $SO_2$;

$R^1$ represents $CO_2R^4$, CN, $CONR^5R^6$, $CH_2CO_2R^4$, optionally substituted alkyl, optionally substituted alkenyl, optionally substituted $SO_2$alkyl, $SO_2NR^5R^6$, NR⁵CONR⁵R⁶, COalkyl, 2H-tetrazol-5-yl-methyl, optionally substituted bicyclic heterocycle or optionally substituted heterocyclyl;

$R^{2a}$ and $R^{2b}$ independently represents hydrogen, halogen, optionally substituted alkyl, optionally substituted alkoxy, CN, SO₂alkyl, SR⁵, NO₂, optionally substituted aryl, CONR⁵R⁶ or optionally substituted heteroaryl;

$R^x$ represents optionally substituted alkyl wherein 1 or 2 of the non-terminal carbon atoms are optionally replaced by a group independently selected from NR⁴, O and SO$_n$, wherein n is 0, 1 or 2: or $R^x$ represents optionally substituted $CQ^aQ^b$-heterocyclyl, optionally substituted $CQ^aQ^b$-bicyclic heterocyclyl or optionally substituted $CQ^aQ^b$-aryl;

R⁴ represents hydrogen or an optionally substituted alkyl;

R⁵ represents hydrogen or an optionally substituted alkyl;

R⁶ represents hydrogen or optionally substituted alkyl, optionally substituted heteroaryl, optionally substituted SO₂aryl, optionally substituted SO₂alkyl, optionally substituted SO₂ heteroaryl, CN, optionally substituted $CQ^aQ^b$aryl, optionally substituted $CQ^aQ^b$heteroaryl or COR⁷;

R⁷ represents hydrogen, optionally substituted alkyl, optionally substituted heteroaryl or optionally substituted aryl;

R⁸ and R⁹ independently represent hydrogen, chloro, fluoro, CF₃, C₁₋₃alkoxy or C₁₋₃alkyl;

$Q^a$ and $Q^b$ are independently selected from hydrogen and CH₃;

wherein when A is a 6-membered ring the R¹ substituent and phenyl ring are attached to carbon atoms 1,2-, 1,3- or 1,4-relative to each other, and when A is a five-membered ring or bicyclic heterocyclyl group the R¹ substituent and phenyl ring are attached to substitutable carbon atoms 1,2- or 1,3-relative to each other;

comprising:
reacting a compound of formula (VIII):

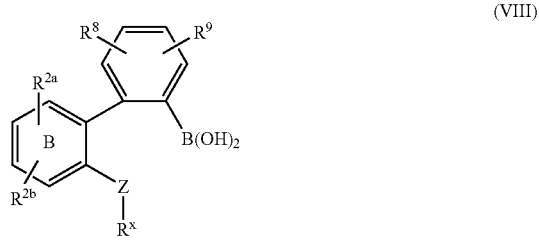

(VIII)

wherein B, $R^{2a}$, $R^{2b}$, Z, R⁸, R⁹, and $R^x$ are as defined for compounds of formula (I),
with a compound of formula (VII):

L-A-R¹P  (VII)

wherein A and R¹ are as hereinbefore defined for compounds of formula (I), L is a leaving group and P is an optional protecting group;
and where required, and in any order, converting:
one group A to another group A, and/or
one group $R^x$ to another group $R^x$;
and where required carrying out the following optional steps in any order:
effecting deprotection; and/or
converting one group R¹ to another group R¹; and/or
forming a derivative of the compound of formula (I) so formed.

The present invention also provides a process for the preparation of a compound of formula (Ia) or a derivative thereof.

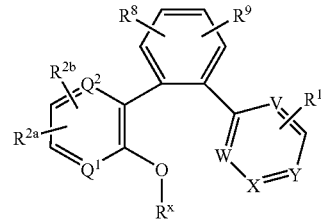

(Ia)

W, X, and Y each represents $CR^{12}$ or N;

V represents $CR^1$, $CR^{12}$ or N;

wherein at least two of W, X, Y or V is $CR^{12}$; and $R^{12}$ is independently selected from hydrogen, halogen, CN, optionally substituted CO₂C₁₋₆alkyl, CONR⁵R⁶, NR⁵R⁶, optionally substituted NR⁵COC₁₋₆alkyl, optionally substituted NR⁵COphenyl, optionally substituted NR⁵COpiperidinyl, optionally substituted NR⁵COheterocyclyl, optionally substituted NR⁵SO₂C₁₋₆alkyl, OH, optionally substituted OC₁₋₆alkyl, optionally substituted C₁₋₆alkyl and NR¹⁰R¹¹;

Q¹ and Q² each represents CH, or one of Q¹ and Q² is N and the other is CH;

R¹ is CO₂H, optionally substituted CONHSO₂aryl, CH₂CO₂H, SO₂NHCOR⁷, SO₂NHCOC₁₋₆alkyl or tetrazolyl and is positioned 1,2-, or 1,3-relative to the phenyl ring;

$R^{2a}$ and $R^{2b}$ are independently selected from hydrogen, halo, or CF₃;

$R^x$ represents optionally substituted C₁₋₈alkyl, or $R^x$ represents optionally substituted $CQ^aQ^b$-heterocyclyl or optionally substituted $CQ^aQ^b$-phenyl wherein $Q^a$ and $Q^b$ are independently selected from hydrogen and CH₃;

R⁴ represents hydrogen or an optionally substituted C₁₋₆alkyl;

R⁵ represents hydrogen or an optionally substituted C₁₋₆alkyl;

R⁶ represents hydrogen or an optionally substituted C₁₋₆alkyl, optionally substituted SO₂phenyl, optionally substituted SO₂heterocyclyl group, CN, optionally substituted CH₂phenyl or COR⁷;

R⁷ represents hydrogen, optionally substituted heteroaryl or optionally substituted phenyl;

R⁸ and R⁹ independently represent hydrogen, chloro, fluoro, CF₃, C₁₋₃alkoxy or C₁₋₃alkyl; and R¹⁰ and R¹¹ together with the nitrogen atom to which they are attached form a morpholine ring, a 5 or 6-membered lactam ring or a 5 or 6-membered cyclic sulphonamide, comprising:
reacting a compound of formula (VIIIa):

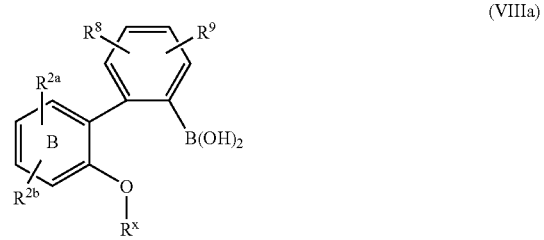

(VIIIa)

wherein B, $R^{2a}$, $R^{2b}$, R⁸, R⁹, and $R^x$ are as defined for compounds of formula (Ia), with a compound of formula (VIIa):

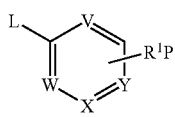

(VIIa)

wherein V, W, X, Y and $R^1$ are as hereinbefore defined for compounds of formula (I), L is a leaving group and P is an optional protecting group;
and where required, and in any order, converting:
one group $R^{12}$ to another group $R^{12}$; and/or
one group $R^x$ to another group $R^x$;
and where required carrying out the following optional steps in any order:
effecting deprotection; and/or
converting one group $R^1$ to another group $R^1$; and/or
forming a derivative of the compound of formula (I) so formed.

It will be appreciated that certain substituents in intermediates and compounds of formula (I) may be converted to other substituents by conventional methods known to those skilled in the art.

A group $R^1$ may be converted to another group $R^1$ by use of conventional organic transformations known to those skilled in the art. For example $R^1=CO_2H$ may be converted to an amide, e.g. $CONHCQ^aQ^b$aryl or $CONHCQ^aQ^b$heteroaryl wherein $Q^a$ and $Q^b$ are selected from hydrogen and $CH_3$, by conventional methods for the preparation of amides as described in, for example, Richard Larock, *Comprehensive Organic Transformations*, 2nd edition, Wiley-VCH, ISBN 0-471-19031-4.

Certain substituents in any of the reaction intermediates and compounds of formula (I) may be converted to other substituents by conventional methods known to those skilled in the art. Examples of substituents which may be converted include one group $R^x$ to another group $R^x$; and one substituent on a group A to another substituent on a group A. Examples of such transformations include the reduction of a nitro group to give an amino group; alkylation and amidation of amino groups; hydrolysis of esters, alkylation of hydroxy and amino groups; and amidation and esterification of carboxylic acids. Such transformations are well known to those skilled in the art and are described in for example, Richard Larock, *Comprehensive Organic Transformations*, 2nd edition, Wiley-VCH, ISBN 0-471-19031-4.

For example, when $R^x$ is p-methoxybenzyl, cleavage of the ether to give the phenol or pyridinol is carried out using, for example, using acid e.g. HCl/dioxane or HBr/acetic acid or using sodium methanethiolate. When $R^x$ is methyl, cleavage of the ether to give the phenol is carried out using, for example, sodium methanethiolate. Cleavage of the ether to give a pyridinol is carried out in the presence of, for example, trifluoroacetic acid. Conversion to another $R^x$ group, for example a substituted benzyl group, may be effected by reaction of the phenol or pyridinol with a suitable substituted benzyl bromide. The skilled person will appreciate that conversion of the protecting group P to another protecting group P may also occur under the reaction conditions used. When $R^x$ is benzyl, cleavage of the ether to give the phenol or pyridinol may be carried out by hydrogenation according to known methods e.g. $H_2$—Pd/C or $NH_4CO_2H$—Pd/C. The resulting phenol or pyridinol can then be converted to another group $R^x$ as described above.

It will be appreciated by those skilled in the art that it may be necessary to protect certain reactive substituents during some of the above procedures. The skilled person will recognise when a protecting group is required. Standard protection and deprotection techniques, such as those described in Greene T. W. 'Protective groups in organic synthesis', New York, Wiley (1981), can be used. For example, carboxylic acid groups can be protected as esters. Deprotection of such groups is achieved using conventional procedures known in the art. It will be appreciated that protecting groups may be interconverted by conventional means.

Phenyl intermediates of the formula (VI):

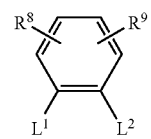

(VI)

wherein $L^1$, $L^2$ are as defined above, and $R^8$ and $R^9$ are as hereinbefore defined for compounds of formula (I) are commercially available or may be readily prepared according to known methods.

Compounds of the formula (III):

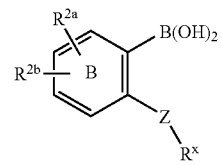

wherein $L^4$ is as hereinbefore defined, $R^{2a}$, $R^{2b}$, Z, B and $R^x$ and are as defined for compounds of formula (I) are commercially available, or may readily be prepared by methods known to those skilled in the art, for example from suitable commercially available pyridinols, anisoles or phenols or compounds of formula (X) using methods as described in the examples.

Intermediates of the formula (V):

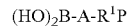

(HO)$_2$B-A-$R^1$P wherein P is an optional protecting group and $R^1$ and A are as hereinbefore defined for compounds of formula (I) are commercially available or may readily be prepared, for example, from suitable halobenzoic acid esters according to known methods, for example using methods as described in the examples.

Intermediates of the formula (VII):

L-A-$R^1$P herein L is a leaving group, e.g. Br, P is an optional protecting group and $R^1$ and A are as hereinbefore defined for compounds of formula (I) are commercially available or may readily be prepared according to known methods, for example using methods as described in the examples.

Phenyl intermediates of the formula (XI):

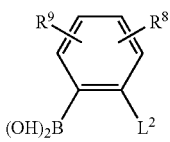

wherein $L^2$ is a leaving group, and $R^8$ and $R^9$ are as hereinbefore defined for compounds of formula (I) are commercially available or may be readily prepared according to known methods from the corresponding compound of formula (VI).

Compounds of the formula (X):

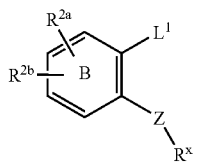

wherein $L^1$ is leaving group, $R^{2a}$, $R^{2b}$, Z, B and $R^x$ and are as defined for compounds of formula (I) are commercially available, or may readily be prepared by methods known to those skilled in the art, for example from suitable commercially available pyridinols, anisoles or phenols using methods as described in the examples.

The preparation and reactions of boronic acids of formula (III), formula (V), formula (VIII) and (XI) is reviewed in Suzuki et al, *Synth. Commun.*, 1981, 11, 513; Martin et al, *Acta. Chim. Scand.*, 1993, 47, 221; and Miyaura et al, *Chem. Rev.*, 1995, 95, 2457. For example, 2-benzyloxy-5-chlorophenylboronic acid may be prepared from 2-benzyloxy-5-chloro-iodobenzene. 2-Benzyloxy-5-chloro-iodobenzene may be prepared from 4-chloro-2-iodoanisole by demethylation followed by benzylation according to known methods.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoismers, including mixtures thereof. The different isomeric forms may be separated or resolved one from the other by conventional methods, or any given isomer may be obtained by conventional synthetic methods or by stereospecific or asymmetric syntheses.

The compounds of the invention bind to the $EP_1$ receptor and they are therefore considered to be useful in treating conditions mediated by the action of $PGE_2$ at $EP_1$ receptors.

Conditions mediated by the action of $PGE_2$ at $EP^1$ receptors include pain; fever; inflammation; immunological diseases; abnormal platelet function diseases; impotence or erectile dysfunction; bone disease; hemodynamic side effects of non-steroidal anti-inflammatory drugs; cardiovascular diseases; neurodegenerative diseases and neurodegeneration; neurodegeneration following trauma; tinnitus; dependence on a dependence-inducing agent; complications of Type I diabetes; and kidney dysfunction.

The compounds of formula (I) are considered to be useful as analgesics. They are therefore considered useful in the treatment or prevention of pain.

The compounds of formula (I) are considered useful as analgesics to treat acute pain, chronic pain, neuropatic pain, inflammatory pain, visceral pain, pain associated with cancer and fibromyalgia, pain associated with migraine, tension headache and cluster headaches, and pain associated with functional bowel disorders, non-cardiac chest pain and non-ulcer dispepsia.

The compounds of formula (I) are considered useful in the treatment of chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of the invention are considered to be particularly useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formula (I) are also considered useful in the treatment of fever.

The compounds of formula (I) are also considered useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, chronic obstructive pulmonary disease, (COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, gingivitis, myocardial ischemia, pyrexia, systemic lupus erythematosus, polymyositis, tendinitis, bursitis, and Sjogren's syndrome.

The compounds of formula (I) are also considered useful in the treatment of immunological diseases such as autoimmune diseases, immunological deficiency diseases or organ transplantation. The compounds of formula (I) are also effective in increasing the latency of HIV infection.

The compounds of formula (I) are also considered useful in the treatment of diseases relating to abnormal platelet function (e.g. occlusive vascular diseases).

The compounds of formula (I) are also considered useful for the preparation of a drug with diuretic action.

The compounds of formula (I) are also considered useful in the treatment of impotence or erectile dysfunction.

The compounds of formula (I) are also considered useful in the treatment of bone disease characterised by abnormal bone metabolism or resorbtion such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis.

The compounds of formula (I) are also considered useful for attenuating the hemodynamic side effects of non-steroidal anti-inflammatory drugs (NSAID's) and cyclooxygenase-2 (COX-2) inhibitors.

The compounds of formula (I) are also considered useful in the treatment of cardiovascular diseases such as hypertension or myocardiac ischemia; functional or organic venous insufficiency; varicose therapy; haemorrhoids; and shock states associated with a marked drop in arterial pressure (e.g. septic shock).

The compounds of formula (I) are also considered useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of formula (I) are also considered useful in the treatment of neuroprotection and in the treatment of neurodegeneration following trauma such as stroke, cardiac arrest, pulmonary bypass, traumatic brain injury, spinal cord injury or the like.

The compounds of formula (I) are also considered useful in the treatment of tinnitus.

The compounds of formula (I) are also considered useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

The compounds of formula (I) are also considered useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of formula (I) are also considered useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

It is to be understood that reference to treatment includes both treatment of established symptoms and prophylactic treatment, unless explicitly stated otherwise.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by the action of $PGE_2$ at $EP^1$ receptors.

According to a further aspect of the invention, we provide a method of treating a human or animal subject suffering from a condition which is mediated by the action of $PGE_2$ at $EP^1$ receptors which comprises administering to said subject an effective amount of a compound of formula (I) or a pharmaceutically acceptable derivative thereof.

According to a further aspect of the invention we provide a method of treating a human or animal subject suffering from a pain, or an inflammatory, immunological, bone, neurodegenerative or renal disorder, which method comprises administering to said subject an effective amount of a compound of formula (I) or a pharmaceutically acceptable derivative thereof.

According to another aspect of the invention, we provide the use of a compound of formula (I) or a pharmaceutically acceptable derivative thereof for the manufacture of a therapeutic agent for the treatment of a condition which is mediated by the action of $PGE_2$ at $EP^1$ receptors.

According to another aspect of the invention we provide the use of a compound of formula (I) or a pharmaceutically acceptable derivative thereof for the manufacture of a therapeutic agent for the treatment or prevention of a condition such as a pain, or an inflammatory, immunological, bone, neurodegenerative or renal disorder.

The compounds of formula (I) and their pharmaceutically acceptable derivatives are conveniently administered in the form of pharmaceutical compositions. Such compositions may conveniently be presented for use in conventional manner in admixture with one or more physiologically acceptable carriers or excipients.

Thus, in another aspect of the invention, we provide a pharmaceutical composition comprising a compound of formula (I) or a pharmaceutically acceptable derivative thereof adapted for use in human or veterinary medicine.

The compounds of formula (I) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously).

The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The $EP_1$ receptor compounds for use in the instant invention may be used in combination with other therapeutic agents, for example COX-2 inhibitors, such as celecoxib, deracoxib, rofecoxib, valdecoxib, parecoxib or COX-189; 5-lipoxygenase inhibitors; NSAID's, such as diclofenac, indomethacin, nabumetone or ibuprofen; leukotriene receptor antagonists; DMARD's such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; $EP_4$ receptor ligands; $EP_2$ receptor ligands; $EP_3$ receptor ligands; $EP_4$ antagonists; $EP_2$ antagonists and $EP_3$ antagonists; cannabanoid receptor ligands; bradykinin receptor ligands and vanilloid receptor ligand. When the compounds are used in combination with other therapeutic agents, the compounds may be administered either sequentially or simultaneously by any convenient route.

Additional COX-2 inhibitors are disclosed in U.S. Pat. No. 5,474,995 U.S. Pat. No. 5,633,272; U.S. Pat. No. 5,466,823, U.S. Pat. No. 6,310,099 and U.S. Pat. No. 6,291,523; and in WO 96/25405, WO 97/38986, WO 98/03484, WO 97/14691, WO 99/12930, WO 00/26216, WO 00/52008, WO 00/38311, WO 01/58881 and WO 02/18374.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A proposed daily dosage of compounds of formula (I) or their pharmaceutically acceptable derivatives for the treatment of man is from 0.01 to 30 mg/kg body weight per day and more particularly 0.1 to 10 mg/kg body weight per day, calculated as the free base, which may be administered as a single or divided dose, for example one to four times per day.

The dose range for adult human beings is generally from 8 to 2000 mg/day, such as from 20 to 1000 mg/day, preferably 35 to 200 mg/day, calculated as the free base.

The precise amount of the compounds of formula (I) administered to a host, particularly a human patient, will be the responsibility of the attendant physician. However, the dose employed will depend on a number of factors including the age and sex of the patient, the precise condition being treated and its severity, and the route of administration.

No unacceptable toxicological effects are expected with compounds of the invention when administered in accordance with the invention.

All publications, including but not limited to patents and patent applications, cited in this specification are herein incorporated by reference as if each individual publication were specifically and individually indicated to be incorporated by reference herein as though fully set forth.

The following non-limiting Examples illustrate the preparation of pharmacologically active compounds of the invention.

EXAMPLES

Abbreviations:
Bn (benzyl), Bu, Pr, Me, Et (butyl, propyl, methyl ethyl), DMSO (dimethyl sulfoxide), DCM (dichloromethane), DME (ethylene glycol dimethyl ether), DMF (N,N-dimethylformamide), EDC (1-(3-dimethylaminopropyl)-3-ethylcarbodiimide), EtOAc (ethyl acetate), EtOH (ethanol), HPLC (High pressure liquid chromatography), LCMS (Liquid chromatography/Mass spectroscopy), MDAP (Mass Directed Purification), MeOH (methanol), NMR (Nuclear Magnetic Resonance (spectrum)), Ph (phenyl), pTSA (para-toluene sulphonic acid), SPE (Solid Phase Extraction), TBAF (tetrabutylammonium fluoride), THF (tetrahydrofuran), s, d, t, q, m, br (singlet, doublet, triplet, quartet, multiplet, broad.)

LCMS
  Column: 3.3 cm×4.6 mm ID, 3 um ABZ+PLUS
  Flow Rate: 3 ml/min
  Injection Volume: 5 μl
  Temp: RT
  UV Detection Range: 215 to 330 nm

| Solvents: | A: 0.1% Formic Acid + 10 m Molar Ammonium Acetate. B: 95% Acetonitrile + 0.05% Formic Acid. | | |
|---|---|---|---|
| Gradient: | Time | A % | B % |
| | 0.00 | 100 | 0 |
| | 0.70 | 100 | 0 |
| | 4.20 | 0 | 100 |
| | 5.30 | 0 | 100 |
| | 5.50 | 100 | 0 |

Mass Directed Autopreparation

Hardware:
Waters 600 gradient pump
Waters 2767 inject/collector

Waters Reagent Manager
Micromass ZMD mass spectrometer
Gilson Aspec—waste collector
Gilson 115 post-fraction UV detector Software:
Micromass Masslynx version 4.0

Column

The column used is typically a Supelco LCABZ++ column Whose dimensions are 20 mm internal diameter by 100 mm in length. The stationary phase particle size is 5 μm.

Solvents:
A:. Aqueous solvent=Water+0.1% Formic Acid
B: Organic solvent=MeCN: Water 95:5+0.05% Formic Acid
Make up solvent=MeOH: Water 80:20+50 mMol Ammonium Acetate
Needle rinse solvent=MeOH: Water DMSO 80:10:10

The method used depends on the analytical retention time of the compound of interest. 15-minute runtime, which comprises a 10-minute gradient followed by a 5-minute column flush and re-equilibration step.
MDP 1.5-2.2=0-30% B
MDP 2.0-2.8=5-30% B
MDP 2.5-3.0=15-55% B
MDP 2.8-4.0=30-80% B
MDP 3.8-5.5=50-90% B Flow rate:
flow rate 20 ml/min.

Example 1

2-Benzyloxy-5-chloro-[1,1';2',1'']terphenyl-3''-carboxylic acid a) 2'-Bromo-biphenyl-3-carboxylic acid ethyl ester A mixture of 1,2-dibromobenzene (0.63 ml, 5.2 mmol), (3-ethoxycarbonylphenyl)boronic acid (506 mg, 2.6 mmol), tetrakis(triphenylphosphine)palladium(0) (640 mg, 0.6 mmol) and potassium carbonate (2.879 g, 20.9 mmol) was heated in toluene-ethanol (1:1, 10 ml at 90° C. for 3 hours. Upon cooling, the mixture was diluted with ethyl acetate and water. The layers were separated and the aqueous phase was extracted with ethyl acetate. The combined extracts were dried ($Na_2SO_4$), filtered and concentrated. The residue was purified by chromatography using Biotage with iso-hexane containing a gradient of DCM (2-15%) to yield the title compound (538 mg, 34%).

$^1$H NMR ($CDCl_3$) δ 1.40 (3H, t, J=7 Hz), 4.40 (2H, q, J=7 Hz), 7.20-7.25 (1H, m), 7.30-7.40 (2H, m), 7.50 (1H, t, J=8 Hz), 7.62 (1H, br d, J=7 Hz), 7.68 (1H, d, J=8 Hz), 8.05-8.10 (2H, m). $R_f$ 0.31 (5% EtOAc in iso-hexane).

b) 2-Benzyloxy-5-chloro-[1,1';2',1'']terphenyl-3''-carboxylic acid ethyl ester

2'-Bromo-biphenyl-3-carboxylic acid ethyl ester (157 mg, 0.5 mmol), 2-benzyloxy-5-chloro-phenylboronic acid (157 mg, 0.6 mmol), tetrakis(triphenylphosphine)palladium(0) (66 mg, 0.06 mmol) and potassium carbonate (568 mg, 4.1 mmol) was heated in toluene-ethanol (1:1, 5 ml) at 90° C. for 4.5 hours. Upon cooling, the mixture was diluted with ethyl acetate and water. The layers were separated and the aqueous phase was extracted with ethyl acetate. The combined extracts were dried ($Na_2SO_4$), filtered and concentrated. The residue was purified by chromatography using Biotage with iso-hexane containing a gradient of ethyl acetate (1-5%) to yield the title compound (105 mg, 46%) as a white solid.

$^1$H NMR ($CDCl_3$) δ (3H, t, J=7 Hz), 4.28 (2H, q, J=7 Hz), 4.50-4.80 (2H, br. s), 6.60 (1H, d, J=9 Hz), 6.94-6.98 (2H, m), 7.10 (1H, dd, J=3 Hz, J=9 Hz), 7.18-7.25 (6H, m's excess), 7.35-7.50 (4H, m), 7.83 (1H, s), 7.88 (1H, dt, J=1 Hz, J=7.5 Hz). $R_f$ 0.15 (5% EtOAc in iso-hexane). LC/MS t=4.23 (100%), [MH+] 443.

c) 2-Benzyloxy-5-chloro-[1,1';2',1'']terphenyl-3''-carboxylic acid

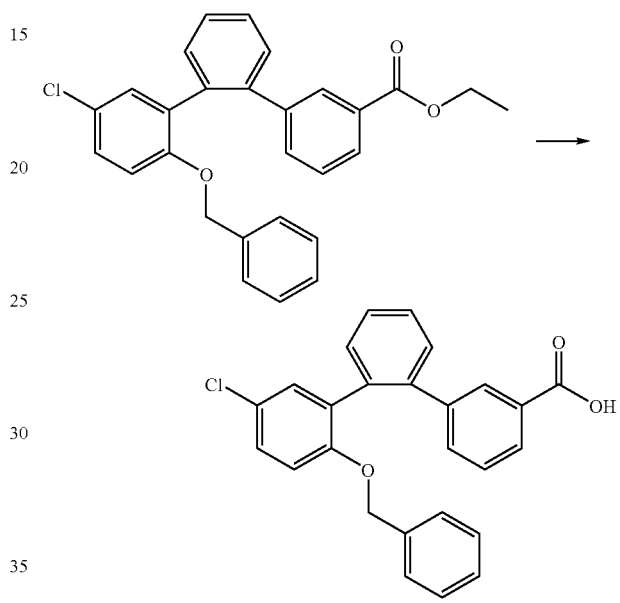

2-Benzyloxy-5-chloro-[1,1',2,2']terphenyl-3''-carboxylic acid ethyl ester (103 mg, 0.2 mmol) was heated at 90° C. in ethanol (2 ml) containing 2M sodium hydroxide (1 ml) in a reacti-vial for 2 hrs. The mixture was cooled to room temperature, diluted with ethyl acetate and washed with 2M HCl, dried ($Na_2SO_4$), filtered and concentrated to yield the title compound (82 mg, 85%).

$^1$H NMR ($CDCl_3$) δ 4.52-4.82 (2H, br. s), 6.62 (1H, d, J=9 Hz), 6.99 (2H, m), 7.12 (1H, dd, J=3 Hz, J=8.5 Hz), 7.18-7.30 (6H, m's excess), 7.36-7.50 (4H, m), 7.90-7:95 (2H, m). LC/MS t=3.97 (100%), [MH−] 413, 415.

Example 2

(2-Benzyloxy-5-chloro-[1,1';2',1'']terphenyl-3''-yl)-acetic acid a) 1-(2'-Bromo-biphenyl-3-yl)-ethanone A mixture of 3-acetylphenylboronic acid (1.64 g, 10 mmol), 1,2-dibromobenzene (4.72 g, 20 mmol), potassium carbonate (6.9 g, 50 mmol) and tetrakis(triphenylphosphine) palladium(0) (0.58 g, 0.5 mmol) in 1:1 toluene/ethanol (40 ml) was stirred and heated at 90° C. under nitrogen for 16 hours. After cooling the mixture was diluted with diethyl ether and water and the organic phase dried ($MgSO_4$) and evaporated to dryness. The residue was purified by chromatography using Biotage with iso-hexane containing a gradient of dichloromethane (20-50%) to yield the title compound as a white solid (1.74 g 63%).

¹H NMR (CDCl₃) δ: 2.64 (3H, s), 7.24-7.39 (3H, m), 7.52-7.70 (3H, m), 7.98-8.00 (2H, m). LC/MS t=3.42, [MH+] 276.9.

b) (2'-Bromophenyl-3-yl)-acetic acid methyl ester

Iodine (533 mg, 2.1 mmol) was added to a stirred suspension of 1-(2'-bromo-biphenyl-3-yl)-ethanone (550 mg, 2 mmol) and silver nitrate (714 mg, 4.2 mmol) in methanol (9 ml) and trimethyl orthoformate (3 ml) and the resulting mixture refluxed for 16 hours. After cooling the mixture was filtered, diluted with water and diethyl ether and the organic phase dried (MgSO₄) and evaporated to dryness. The residue was purified using Biotage with dichloromethane/iso-hexane (3:7) to yield the title compound as a colourless gum (499 mg 82%).

¹H NMR (CDCl₃) δ: 3.69 (2H, s), 3.71 (3H, s), 7.19-7.39 (7H, s), 7.66 (1H, d, J=8 Hz). LC/MS t=3.49, [MH+] 306.9.

c) (2-Benzyloxy-5-chlorol[1,1';2',1"]terphenyl-3"-yl) acetic acid ethyl ester A mixture of (2'-bromo-biphenyl-3-yl)-acetic acid methyl ester (76 mg, 0.25 mmol), 2-benzyloxy-5-chloro-phenyl-boronic acid (72 mg, 0.275 mmol), potassium carbonate (276 mg, 2 mmol) and tetrakis(triphenylphosphine)palladium(0) (29 mg, 0.025 mmol) in 1:1 toluene/ethanol (3 ml) was heated and stirred at 90° C. under nitrogen for 2 hours. After cooling the mixture was diluted with water and diethyl ether and the organic phase dried (MgSO₄) and evaporated to dryness. The residue was purified by chromatography using Biotage with ethyl acetate/iso-hexane (1:19) to yield the title compound as a colourless gum (112 mg, 98%).

¹H NMR (CDCl₃) δ: 1.2 (3H, t, J=7 Hz), 3.40 (2H, s), 4.06 (2H, q, J=7 Hz), 4.66 (2H, br s), 6.59 (1H, d, J=8 Hz), 6.96-7.42 (15H, m).

d) (2-Benzyloxy-5-chloro-[1,1';2'1"]terphenyl-3"-yl)-acetic acid

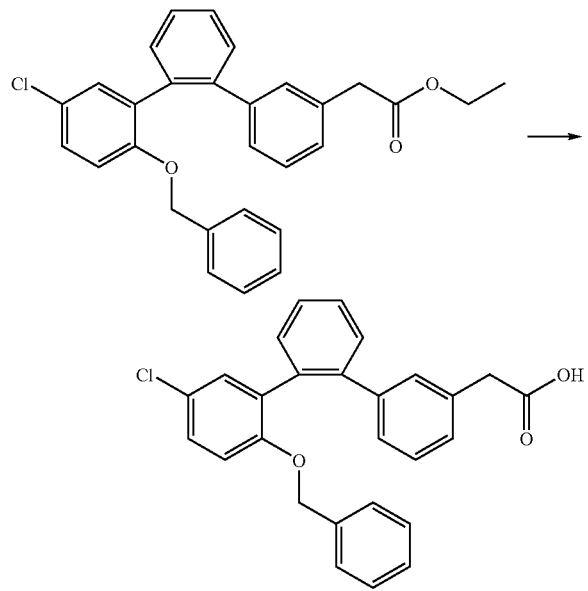

A solution of (2-benzyloxy-5-chloro-[1,1';2',1"]terphenyl-3"-yl)-acetic acid ethyl ester (112 mg, 0.25 mmol) in ethanol (5 ml) and 2M sodium hydroxide (1 ml, 2 mmol) was stirred at room temperature for 1 hour then diluted with water and 1:1 diethyl ether/iso-hexane. The aqueous suspension was separated, acidified with 1M hydrochloric acid and extracted with diethyl ether. The organic solution was dried (MgSO₄) evaporated to dryness and the residue triturated with iso-hexane to give the title compound as a white solid (86 mg, 80%).

¹H NMR (CDCl₃) δ: 3.56 (2H, s), 4.78 (2H, br s), 6.71 (1H, d, J=8 Hz), 7.10-7.59 (15H, m). LC/MS t=3.86, [MH−] 427, 429

Examples 3 and 4 were prepared in a similar manner:

Example 3

(2-Benzyloxy-5-chloro[1,1';2',1"]terphenyl-2"-yl) acetic acid a) 1-(2'-Bromo-biphenyl-2-yl)-ethanone

¹H NMR (CDCl₃) δ: 2.36 (3H, s), 7.38-7.91 (8H, m). LC/MS t=3.31, [MH+]276.9 b) (2'-Bromo-biphenyl-2-yl)-acetic acid methyl ester

¹H NMR (CDCl₃) δ: 3.47 (2H, q), 3.56 (3H, s), 7.16-7.64 (7H, m), 7.65 (1H, d).

c) (2-Benzyloxy-5-chloro[1,1';2',1"]terphenyl-2"-yl) acetic acid ethyl ester ¹H NMR (CDCl₃) δ: 1.15 (3H, t, J=7 Hz), 3.20 (1H, br d), 3.43 (1H, d, J=16 Hz), 4.03 (2H, q, J=7 Hz), 4.86 (2H, q), 6.61 (1H, d), 6.99-7.40 (15H, m).

d) (2-Benzyloxy-5-chloro[1,1';2',1"]terphenyl-2"-yl) acetic acid

¹H NMR (CDCl₃) δ: 3.18 (1H, br d), 3.44 (1H, d, J=16 Hz), 4.83 (2H, q), 6.60 (1H, d, J=9 Hz) 7.02-7.40 (15H, m). LC/MS t=3.81, [MH−] 427, 429.1

Example 4

(2-Benzyloxy-5-chloro[1,1';2',1"]terphenyl-4"-yl) acetic acid a) 1-(2'-Bromo-biphenyl-4-yl)-ethanone

¹H NMR (CDCl₃) δ: 2.66 (3H, s), 7.25-7.39 (3H, m), 7.52 (2H, d, J=8 Hz), 7.69 (1H, d, J=8 Hz), 8.03 (2H, d, J=8 Hz). LC/MS t=3.45, [MH+] 274.9 b) (2'Bromo-biphenyl-4-yl)-acetic acid methyl ester

¹H NMR (CDCl₃) δ: 3.68 (2H, s), 3.73 (3H, s), 7.17-7.40 (7H, m), 7.67 (1H, d, J=8 Hz)

c) (2-Benzyloxy-5-chloro[1,1';2',1"]terphenyl-4"-yl) acetic acid ethyl ester ¹H NMR (CDCl₃) δ: 1.22 (3H, t, J=7 Hz), 3.56 (2H, s), 4.14 (2H, q, J=7 Hz), 4.64 (2H, br s), 6.61 (1H, d, J=8 Hz), 6.99-7.41 (15H, m).

d) (2-Benzyloxy-5-chloro[1,1';2',1"]terphenyl-4"-yl) acetic acid $^1$H NMR (CDCl$_3$) δ: 3.61 (2H, s), 4.62 (2H, br s), 6.59 (1H, d, J=8 Hz), 6.98-7.42 (15H, m).

Example 5

5"-Acetylamino-2-benzyloxy-5-chloro[1,1';2',1"]terphenyl-3"-carboxylic acid a) 5-Amino-2'-bromobiphenyl-3-carboxylic acid methyl ester

A mixture of (3-amino-5-methoxycarbonylphenyl)boronic acid (1.02 g, 5.23 mmol), 1,2-dibromobenzene (2.47 g, 10.46 mmol), potassium carbonate (5.52 g, 40 mmol) and tetrakis(triphenylphosphine)palladium(0) (606 mg, 0.523 mmol) in 1:1 toluene/ethanol (30 ml) was stirred and heated at 90° C. under nitrogen for 2 hours. After cooling the mixture was diluted with diethyl ether and water and the organic phase dried (MgSO$_4$) and evaporated to dryness. The residue was purified using Biotage with ethyl acetate/iso-hexane (3:17) to yield the title compound as a colourless gum (1.21 g, 76%).

$^1$H NMR (CDCl$_3$) δ: 3.86 (2H, br s), 3.90 (3H, s), 6.90 (1H, s), 7.19-7.38 (4H, m), 7.45 (1H, s), 7.65 (1H, d, J=8 Hz).

b) 5"-Amino-2-benzyloxy-5-chloro[1,1';2',1"]terphenyl-3"-carboxylic acid ethyl ester A mixture of 2-benzyloxy-5-chloro-phenyl-boronic acid (197 mg, 0.75 mmol), 5-amino-2'-bromo-biphenyl-3-carboxylic acid methyl ester (216 mg, 0.71 mmol), potassium carbonate (828 mg, 6 mmol) and tetrakis(triphenylphosphine)palladium(0) (79 mg, 0.068 mmol) in 1:1 toluene/ethanol (8 ml) was stirred and heated at 90° C. under nitrogen for 2 hours. After cooling the mixture was diluted with diethyl ether and water and the organic phase dried (MgSO$_4$) and evaporated to dryness. The residue was purified using Biotage with ethyl acetate/iso-hexane (1:4) to yield the title compound as a pale yellow gum. (288 mg, 89%).

$^1$H NMR (CDCl$_3$) δ: 1.25 (3H, t, J=7 Hz), 3.52 (2H, br s), 4.23 (2H, q, J=7 Hz), 4.68 (2H, br s), 6.52 (1H, s), 6.63 (1H, d, J=9 Hz), 7.00-7.41 (13H, m). LC/MS t=3.93, [MH+] 458.2, 460.2.

c) 5"-Acetylamino-2-benzyloxy-5-chloro[1,1';2',1"]terphenyl-3"-carboxylic acid ethyl ester Acetic anhydride (53 mg, 0.5 mmol) was added to a solution of 5"-amino-2-benzyloxy-5-chloro-[1,1';2',1"]terphenyl-3"-carboxylic acid ethyl ester (96 mg, 0.21 mmol) in pyridine (2 ml) and the mixture left at room temperature for 1 hour. The resulting solution was diluted with diethyl ether, washed with 1M hydrochloric acid and saturated sodium bicarbonate solution, dried (MgSO$_4$) and evaporated to dryness to yield the title compound as a colourless gum. (102 mg, 97%).

$^1$H NMR (CDCl$_3$) δ: 1.29 (3H, t, J=7 Hz), 2.10 (3H, s), 4.25 (2H, q), 4.70 (2H, br d), 6.63 (1H, d, J=9 Hz), 6.99-7.43 (12H, m), 7.50 (1H, s), 8.00 (1H, s). LC/MS t=3.86, [MH+] 500, 502.1.

d) 5"-Acetylamino-2-benzyloxy-5-chloro[1,1';2',1"]terphenyl-3"-carboxylic acid

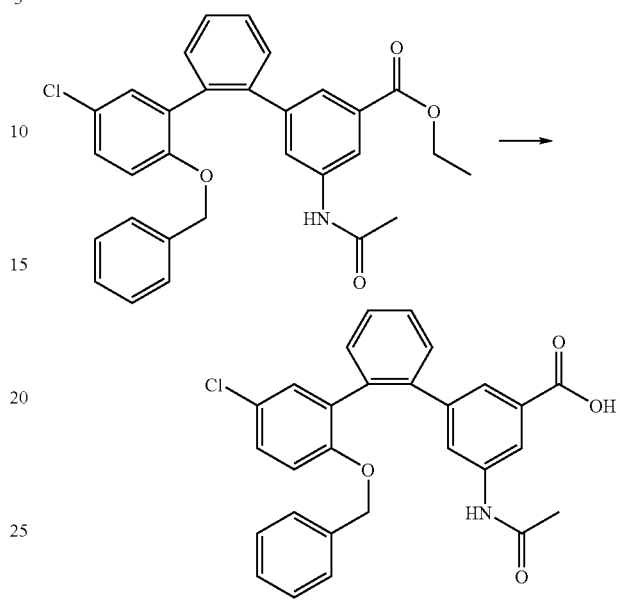

5"-Acetylamino-2-benzyloxy-5-chloro-[1,1',2',1"]terphenyl-3"-carboxylic acid ethyl ester (102 mg, 0.2 mmol) was dissolved in a mixture of ethanol (5 ml) and 2M sodium hydroxide (1 ml, 2 mmol) and left at room temperature for 5 hours. The resulting solution was diluted with water, washed with diethyl ether and the aqueous phase separated, acidified with 1M hydrochloric acid and extracted with diethyl ether. The organic phase was dried (MgSO$_4$) and evaporated to dryness to yield the title compound as a white solid. (81 mg, 84%).

$^1$H NMR (CDCl$_3$) δ: 2.12 (3H, s), 4.70 (2H, br d), 6.65 (1H, d, J=8 Hz), 7.00-7.45 (12H, m) 7.58 (1H, s), 8.07 (1H, s). LC/MS t=3.59, [MH−] 470.1, 472.1.

Example 6

2-Benzyloxy-5-chloro-5"-propionylamino[1,1';2',1"]terphenyl-3"-carboxylic acid a) 2-Benzyloxy-5-chloro-5"-propionylamino[1,1';2',1"]terphenyl-3"-carboxylic acid ethyl ester Propionyl chloride (10 mg, 0.11 mmol) was added to a solution of 5"-amino-2-benzyloxy-5-chloro-[1,1',2',1"]terphenyl-3"-carboxylic acid ethyl ester (47 mg, 0.1 mmol) and triethylamine (12 mg, 0.12 mmol) in dichloromethane (2 ml) and the mixture left at room temperature for 2 hours. The resulting solution was diluted with diethyl ether, washed with 1M hydrochloric acid and saturated sodium bicarbonate solution then dried (MgSO$_4$) and evaporated to dryness. The residue was purified by chromatography using Biotage with ethyl acetate/iso-hexane (1:3) to yield the title compound as a colourless gum. (49 mg, 95%).

$^1$H NMR (CDCl$_3$) δ: 1.21 (3H, t, J=7 Hz), 1.30 (3H, t, J=7 Hz), 2.30 (2H, q, J=7 Hz), 4.25 (2H, q, J=7 Hz), 4.68 (2H, br d), 6.63 (1H, d, J=9 Hz), 6.88 (1H, s), 7.00-7.50 (13H, m), 8.03 (1H, s). LC/MS t=4.03, [MH+] 514.2, 516.2.

b) 2-Benzyloxy-5-chloro-5"-propionylamino[1,1';2', 1"]terphenyl-3"-carboxylic acid

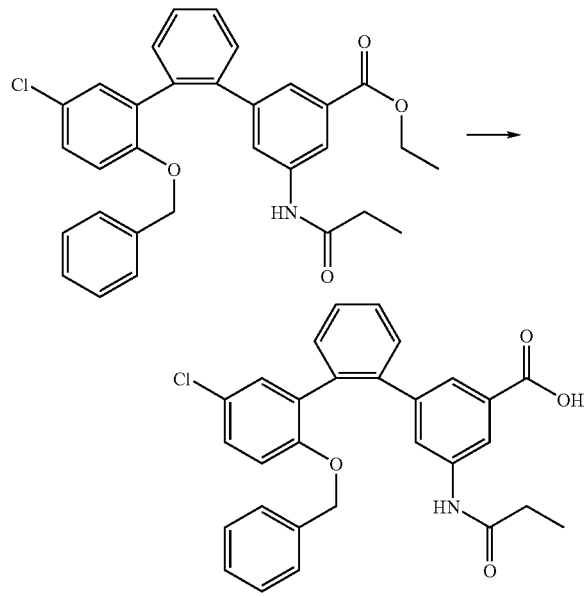

2-Benzyloxy-5-chloro-5"-propionylamino-[1,1';2',1"]ter-phenyl-3"-carboxylic acid ethyl ester (49 mg, 0.095 mmol) was dissolved in ethanol (5 ml) and 1M sodium hydroxide (1 ml, 1 mmol) and left at room temperature for 5 hours. The resulting solution was diluted with water acidified with 1M hydrochloric acid and extracted with diethyl ether. The organic phase was dried (MgSO$_4$) evaporated to dryness and triturated with iso-hexane to yield the title compound as an off-white solid. (31 mg, 67%).

$^1$H NMR (CDCl$_3$) δ: 1.21 (3H, t, J=7 Hz), 2.33 (2H, q, J=7 Hz), 4.70 (2H, br d), 6.65 (1H, d, J=9 Hz), 6.90 (1H, s), 7.03-7.46 (12H, m), 7.57 (1H, s), 8.10 (1H, s). LC/MS t=3.75, [MH−] 484.3, 486.2.

Examples 7 to 9 were prepared in a similar manner:

Example 7

2-Benzyloxy-5-chloro-5"-(2-methylpropanoy-lamino)-[1,1';2',1"]terphenyl-3"-carboxylic acid a) 2-Benzyloxy-5-chloro-5"-(2-methylpropanoy-lamino)-[1,1';2',1"]terphenyl-3"-carboxylic acid ethyl ester $^1$H NMR (CDCl$_3$) δ: 1.20 (3H, s), 1.22 (3H, s), 1.30 (3H, t, J=7 Hz), 2.42 (1H, m), 4.25 (2H, q, J=7 Hz), 4.70 (2H, br d), 6.63 (1H, d, J=9 Hz), 6.90-7.50 (14H, m), 8.02 (1H, s). LC/MS t=4.11, [MH+] 528.3, 530.2.

b) 2-Benzyloxy-5-chloro-5"-(2-methylpropanoy-lamino)-[1,1';2',1"]terphenyl-3"-carboxylic acid $^1$H NMR (CDCl$_3$) δ: 1.17 (3H, s), 1.21 (3H, s), 2.43 (1H, m), 4.70 (2H, br d), 6.66 (1H, d, J=9 Hz), 6.91 (1H, s), 7.03-7.47 (12H, m), 7.57 (1H, s), 8.10 (1H, s). LC/MS t=3.85, [MH−]498.2, 500.2.

Example 8

2-Benzoyloxy-5"-butyrylamino-5-chloro[1,1';2',1"]terphenyl-3"-carboxylic acid a): 2-Benzoyloxy-5"-butyrylamino-5-chloro[1,1';2', 1"]terphenyl-3"-carboxylic acid ethyl ester $^1$H NMR (CDCl$_3$) δ: 0.95 (3H, t, J=7 Hz), 1.29 (3H, t, J=7 Hz), 1.70 (2H, m), 2.26 (2H, t, J=7 Hz), 4.25 (2H, q, J=7 Hz), 4.70 (2H, br d), 6.63 (1H, d, J=9 Hz), 6.91 (1H, s), 7.01-7.51 (12H, m), 8.02 (1H, s). LC/MS t=4.12, [MH+] 528.1, 530.1.

b): 2-Benzoyloxy-5"-butyrylamino-5-chloro[1,1';2', 1"]terphenyl-3"-carboxylic acid $^1$H NMR (CDCl$_3$) δ: 0.99 (3H, t, J=7 Hz). 1.72 (2H, m), 2.27 (2H, t, J=7 Hz), 4.71 (2H, br d), 6.65 (1H, d, J=9 Hz), 6.87 (1H, s), 7.02-7.46 (12H, m), 7.58 (1H, s), 8.09 (1H, s). LC/MS t=3.86, [MH−] 498.1, 500.1.

Example 9

2-Benzyloxy-5-chloro-5"-[(1-phenyl-methanoyl)amino]-[1,1';2',1"]terphenyl-3"-carboxylic acid a) 2-Benzyloxy-5-chloro-5"-[(1-phenyl-methanoyl)amino]-[1,1';2',1"]terphenyl-3"-carboxylic acid ethyl ester $^1$H NMR (CDCl$_3$) δ: 1.26 (3H, t, J=7 Hz), 4.26 (2H, q, J=7 Hz), 4.70 (2H, br d), 6.65 (1H, J=9 Hz), 7.02-7.57 (16H, m), 7.79 (2H, m), 8.15 (1H, s). LC/MS t=4.22, [MH+] 562.2, 564.2.

b) 2-Benzyloxy-5-chloro-5"-[(1-phenyl-methanoyl)amino]-[1,1';2',1"]terphenyl-3"-carboxylic acid $^1$H NMR (CDCl$_3$) δ: 4.70 (2H, br d), 6.67 (1H, d, J=9 Hz), 7.04-7.61 (17H, m), 7.80 (2H, d, J=7 Hz), 8.23 (1H, s). LC/MS t=4.01, [MH−] 532.2, 534.3.

Example 10

2-Benzyloxy-5-chloro-5"-methanesulfonylamino-[1, 1';2',1"]terphenyl-3"-carboxylic acid a) 2-Benzyloxy-5-chloro-5"-dimethanesulfony-lamino-[1,1';2',1"]terphenyl-3"-carboxylic acid ethyl ester Methanesulphonyl chloride (25 mg, 0.22 mmol) was added to a solution of 5"-amino-2-benzyloxy-5-chloro-[1,1',2',1"]terphenyl-3"-carboxylic acid ethyl ester (47 mg, 0.1 mmol) and triethylamine (25 mg, 0.25 mmol) and the mixture left at room temperature for 3 hours. The resulting solution was diluted with diethyl ether, washed with 1M hydrochloric acid and saturated sodium bicarbonate solution then dried (MgSO$_4$) and evaporated to dryness. The residue was purified by chromatography using Biotage with ethyl acetate/iso-hexane (1:4) to yield the title compound as a colurless gum. (56 mg, 91%).

$^1$H NMR (CDCl$_3$) δ: 1.26 (3H, t, J=7 Hz), 3.14 (6H, br d), 4.18 (2H, br s), 4.48 (1H, br d), 4.69 (1H, br d), 6.66 (1H, d, J=9 Hz), 6.94-7.51 (12H, m), 7.80 (1H, s), 7.95 (1H, s).

b) 2-Benzyloxy-5-chloro-5"-methanesulfonylamino-[1,1';2',1"]terphenyl-3"-carboxylic acid

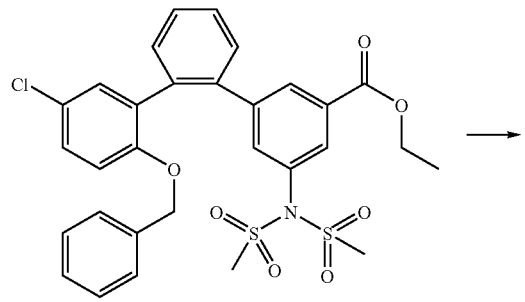

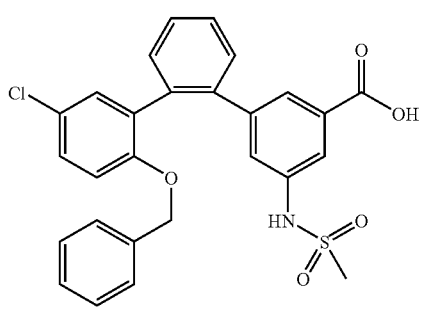

2-Benzyloxy-5-chloro-5"-dimethanesulfonylamino-[1,1'; 2',1"]terphenyl-3"-carboxylic acid ethyl ester was dissolved in ethanol (5 ml) and 1M sodium hydroxide (1 ml, 1 mmol) and left at room temperature for 5 hours then heated at 50° C. for 1 hour. The resulting solution was diluted with water, acidified with 1M hydrochloric acid and extracted with diethyl ether. The organic phase was dried (MgSO$_4$), evaporated to dryness and triturated with diethyl ether/iso-hexane to yield the title compound as a white solid. (21 mg, 46%).

$^1$H NMR (DMSO-d$_6$) δ: 2.67 (3H, s), 4.85 (2H, br s), 6.91 (1H, d, J=9 Hz), 7.03-7.53 (13H, m), 7.67 (1H, s), 9.87 (1H, s), 12.9 (1H, br s). LC/MS t=3.68, [MH–] 506.2, 508.2.

Example 11

5"-Amino-2-benzyloxy-5-chloro[1,1';2',1"]-terphenyl-4"-carboxylic acid

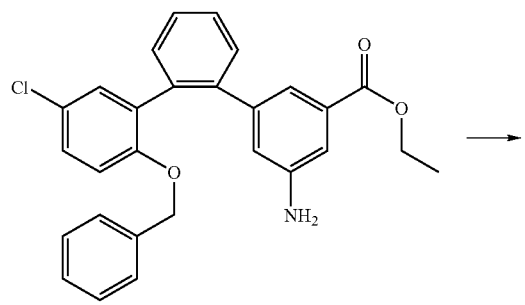

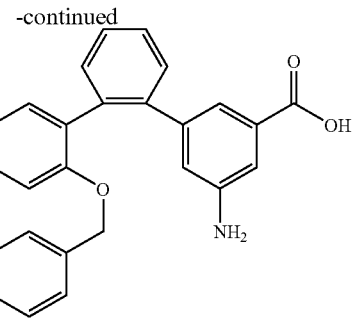

5"-Amino-2-benzyloxy-5-chloro-[1,1';2',1"]terphenyl-3"-carboxylic acid ethyl ester (192 mg, 0.42 mmol) was dissolved in ethanol (5 ml) and 2M sodium hydroxide (2 ml, 4 mmol) and heated at 60° C. for 1 hour. The resulting solution was diluted with water acidified with acetic acid and extracted with diethyl ether. The organic phase was dried (MgSO$_4$) evaporated to dryness and triturated with iso-hexane/diethyl ether to yield the title compound as a white solid. (141 mg, 78%).

$^1$H NMR (DMSO-d$_6$) δ: 4.9 (2H, br s), 5.23 (2H, br s), 6.58 (1H, s), 6.89 (1H, s), 6.95 (1H, d, J=9 Hz), 7.02 (1H, dd, J=9 Hz, 2 Hz), 7.13 (1H, d, J=9 Hz), 7.24-7.41 (10H, m), 12.4 (1H, br s). LC/MS t=3.59 [MH–] 470.1, 472.1.

Example 12

2-Benzyloxy-5"-butyrylamino-5-trifluoromethyl[1,1';2',1"]terphenyl-3"-carboxylic acid a) 2'-Bromo-5-butyrylamino-biphenyl-3-carboxylic acid methyl ester Butyryl chloride (55 mg, 0.52 mmol) was added to a solution of 5-amino-2'-bromo-biphenyl-3-carboxylic acid methyl ester (153 mg, 0.5 mmol) and triethylamine (76 mg, 0.75 mmol) in dichloromethane (5 ml) and the mixture left at room temperature for 30 minutes. The resulting solution was diluted with diethyl ether, washed with 1M hydrochloric acid and saturated sodium bicarbonate, dried (MgSO$_4$) and evaporated to dryness to yield the title compound as a light yellow gum. (161 mg, 88%).

$^1$H NMR (CDCl$_3$) δ: 1.01 (3H, t, J=7 Hz), 1.77 (2H, m), 2.37 (2H, t, J=7 Hz), 3.92, (3H, s), 7.20-7.36 (3H, m), 7.43 (1H, br s), 7.66 (1H, d, J=8 Hz), 7.83 (1H, s), 7.94 (1H, s), 8.10 (1H, s). LC/MS t=3.54, [MH+] 378.

b) 4-Benzyloxy-3-bromobenzotrifluoride

A solution of 3-bromo-4-hydroxybenzotrifluoride (6.03 g, 25 mmol) in acetone (1000 ml) was treated with benzyl bromide (4.67 g, 3.25 ml, 27.5 mmol) and potassium carbonate (5.18 g, 37.5 mmol). The mixture was stirred and heated to reflux under nitrogen for 2 h. After cooling, diethyl ether (300 ml) and water (300 ml) were added and the aqueous phase re-extracted with diethyl ether (100 ml). The combined organic layers were washed with water, dried (MgSO$_4$) and the solvent removed in vacuo. The orange oil was flash chromatographed (silica gel, 2-5% dichloromethane-isohexane) to give the title compound as a clear oil (7.0 g, 85%).

$^1$H NMR (CDCl$_3$) δ: 5.22 (2H, s), 6.98 (1H, d, J=9 Hz), 7.34-7.51 (6H, m), 7.83 (1H, s). The product contains a trace impurity that can be removed by recrystallisation from iso-hexane at −78° C.

c) 2-Benzyloxy-5-trifluoromethylbenzeneboronic acid

A solution of 4-benzyloxy-3-bromobenzotrifluoride (4.48 g, 13.54 mmol) in tetrahydrofuran (100 ml) was cooled to −100° C. (diethyl ether/liquid nitrogen) with stirring under nitrogen. 1.6 M n-butyllithium in hexanes (9.3 ml, 14.89 mmol) was added over 20 mins. at −100° C. and the mixture warmed to −78° C. (acetone/Drikold) and stirred for 1 h. Triisopropylborate (7.64 g, 9.38 ml, 40.66 mmol) was added dropwise at −78° C. and the reaction stirred and allowed to warm to room temperature over 1.5 h. 1M Hydrochloric acid (100 ml) was added and the mixture stirred vigorously for 1 h. The layers were separated and the aqueous layer extracted with diethyl ether (50 ml). The combined organic phases were washed with water, dried (MgSO$_4$) and the solvent removed in vacuo. The yellow waxy solid was flash chromatographed (silica gel, 4-20% EtOAc-isohexane) and the product triturated with hexane. The white solid was filtered and dried in vacuo to give the title compound (1.53 g, 38%).

$^1$H NMR (CDCl$_3$) δ: 5.20 (2H, s), 5.76 (2H, s), 7.05 (1H, d, J=9 Hz), 7.42-7.44 (5H, m), 7.68 (1H, dd J=2 Hz, J=9 Hz), 8.15 (1H, s).

d) 2-Benzyloxy-5"-butyrylamino-5-trifluoromethyl [1,1';2',1"]terphenyl-3"-carboxylic acid ethyl ester A mixture of 2-benzyloxy-5-trifluoromethyl-phenyl-boronic acid (38 mg, 0.13 mmol), 2'-bromo-5-butyrylamino-biphenyl-3-carboxylic acid methyl ester (45 mg, 0.12 mmol), potassium carbonate (138 mg, 1 mmol) and tetrakis(triphenylphosphine)palladium(0) (14 mg, 0.012 mmol) in 1:1 toluene/ethanol (3 ml) was stirred and heated at 90° C. under nitrogen for 2 hours. After cooling the mixture was diluted with diethyl ether and water and the organic phase dried (MgSO$_4$) and evaporated to dryness. The residue was purified using Biotage with ethyl acetate/iso-hexane (1:4) to yield the title compound as a colourless gum (51 mg, 76%).

$^1$H NMR (CDCl$_3$) δ: 0.97 (3H, t, J=7 Hz), 1.26 (3H, t, J=7 Hz), 1.71 (2H, m), 2.25 (2H, t, J=7 Hz), 4.23 (2H, q, J=7 Hz), 6.75 (1H, d, J=8 Hz), 6.89 (1H, s), 7.02 (2H, m) 7.24-7.47 (11H, m), 7.51 (1H, s), 7.97 (1H, s). LC/MS=4.13, [MH−] 560.2.

e) 2-Benzyloxy-5"-butyrylamino-5-trifluoromethyl [1,1';2',1"]terphenyl-3"-carboxylic acid

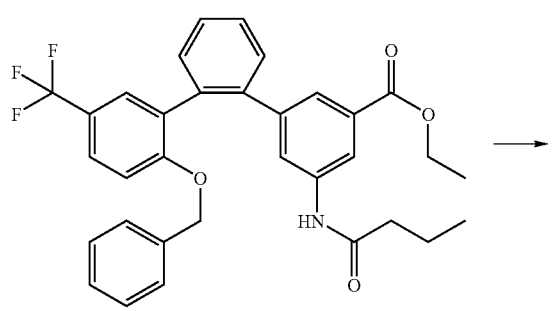

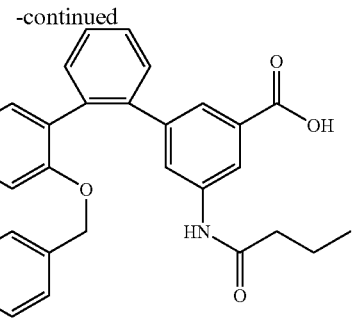

2-Benzyloxy-5"-butyrylamino-5-trifluoromethyl-[1,1',2',1"]terphenyl-3"-carboxylic acid ethyl ester (51 mg, 0.091 mmol) was dissolved in ethanol (5 ml) and 2M sodium hydroxide (1 ml, 2 mmol) and left at room temperature for 18 hours. The resulting solution was diluted with water acidified with 1M hydrochloric acid and extracted with diethyl ether. The organic phase was dried (MgSO$_4$) evaporated to dryness and triturated with iso-hexane to yield the title compound as an off-white solid. (40 mg, 83%).

$^1$H NMR (CDCl$_3$) δ: 0.97 (3H, t, J=7 Hz), 1.71 (2H, m), 2.26 (2H, t, J=7 Hz), 4.82 (2H, br s), 6.78 (1H, d, J=9 Hz), 6.88 (1H, s), 7.04 (2H, d, J=7 Hz), 7.25-7.48 (10H, m), 7.54 (1H, s), 8.03(1H, s). LC/MS t=3.87, [MH−] 532.2.

Example 13

2-Benzyloxy-4"-chloro[1,1';2',1"]terphenyl 2"-carboxylic acid a) 2'-Benzyloxy-2-bromobiphenyl

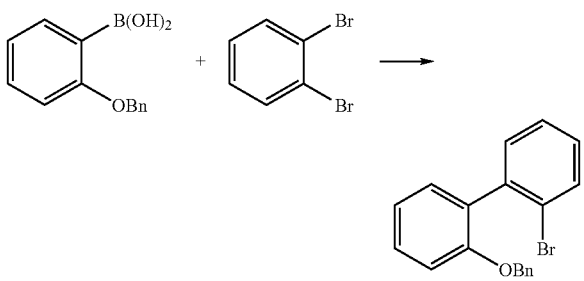

A solution of 2-benzyloxyphenylboronic acid (4.3 g. 19.3 mmol) and 1,2-dibromobenzene (9.11 g, 4.66 ml, 38.6 mmol) in 1:1 toluene:ethanol (150 ml) was stirred under nitrogen and tetrakis(triphenylphosphine)palladium(0) (1.12 g, 0.95 mmol) and potassium carbonate (21.3 g, 154 mmol) added. The reaction was stirred at 90° C. under nitrogen for 2 hours. After cooling, diethyl ether (100 ml) and water (100 ml) were added and the organic phase separated. The aqueous phase was extracted with diethyl ether (50 ml) and the combined organic layers washed with water, dried (MgSO$_4$) and the solvent removed in vacuo. The residue was flash chromatographed (silica gel, 5-15% CH$_2$Cl$_2$-isohexane) to give the title compound as a clear oil (4.53 g, 69%).

$^1$H NMR (CDCl$_3$) δ: 5.07 (2H, s), 7.02 (2H, m), 7.19-7.34 (10H, m), 7.65 (1H, d, J=8 Hz).

b) 2'-Benzyloxy-biphenyl-2-boronic acid

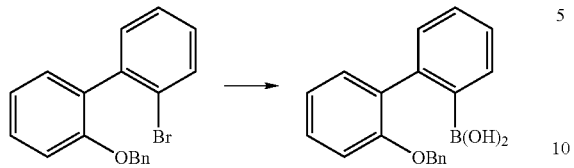

A solution of 2'-benzyloxy-2-bromobiphenyl (2.41 g, 7.09 mmol) in tetrahydrofuran (50 ml) was stirred under nitrogen and cooled to −100° C. (diethyl ether/liquid nitrogen). 1.6M "Butyllithium in hexanes (4.87 ml, 7.80 mmol) was added over 15 mins. at −100° C. and the mixture warmed to −78° C. (acetone/Drikold) and stirred for 1 h. Triisopropyl borate (4.00 g (5.02 ml, 21.30 mmol) was added at −78° C. and the reaction allowed to warm to room temperature with stirring over 1.5 h. 1M Hydrochloric acid (50 ml) was added and the mixture stirred vigorously for 1 h. The organic layer was separated and the aqueous layer extracted with diethyl ether (50 ml). The combined organic phase were washed with water, dried (MgSO$_4$) and the solvent removed in vacuo. The yellow oil was flash chromatographed (silica gel, 10-20% EtOAc-isohexane) to give the title compound as a clear oil (1.74 g, 80%). LC/MS RT=3.28 min [(2M−H$_2$O)H−]=589.3 c) 2-Benzyloxy-4"-chloro-[1,1';2',1"]terphenyl-2"-carboxylic acid ethyl ester A mixture of 2'-benzyloxy-biphenyl-2-boronic acid (61 mg, 0.2 mmol), ethyl 2-bromo-5-chlorobenzoate (53 mg, 0.2 mmol), potassium carbonate (207 mg, 1.5 mmol) and tetrakis(triphenylphosphine)palladium(0) (23 mg, 0.02 mmol) in 1:1 toluene/ethanol (3 ml) was stirred and heated at 90° C. under nitrogen for 2 hours. After cooling the mixture was diluted with diethyl ether and water and the organic phase dried (MgSO$_4$) and evaporated to dryness. The residue was purified using Biotage with ethyl acetate/iso-hexane (1:19) to yield the title compound as a colourless gum (63 mg, 71%).

$^1$H NMR (CDCl$_3$) δ: 0.97 (3H, br s), 3.99 (2H, br s), 4.87 (2H, br q), 6.75-6.81 (2H, m), 6.98-7.02 (2H, m), 7.14-7.41 (11H, m), 7.65 (1H, d, J=2 Hz).

d) 2-Benzyloxy-4"-chloro[1,1';2',1"]terphenyl-2"-carboxylic acid

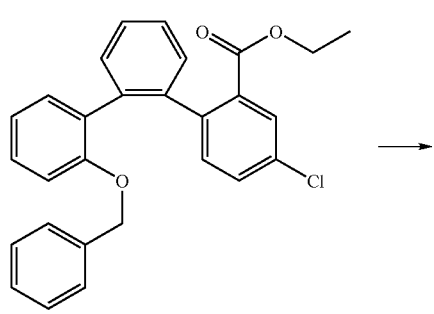

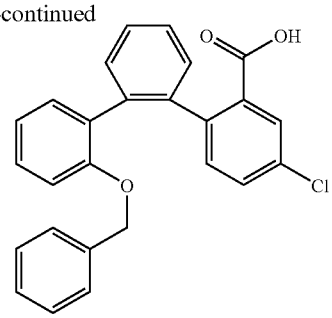

2-Benzyloxy-4"chloro-[1,1',2',1"]terphenyl-2"-carboxylic acid ethyl ester (58 mg, 0.137 mmol) was dissolved in ethanol (5 ml) and 2M sodium hydroxide (1 ml, 2 mmol) and heated at 75° C. for 9 hours. The resulting solution was diluted with water, washed with iso-hexane and the aqueous suspension separated, acidified with 1M hydrochloric acid and extracted with diethyl ether. The organic phase was dried (MgSO$_4$) evaporated to dryness and triturated with iso-hexane/diethyl ether to yield the title compound as a white solid. (26 mg, 48%).

$^1$H NMR (CDCl$_3$) δ: 4.91 (2H, br d), 6.71 (1H, d, J=8 Hz), 6.80-7.47 (14H, m), 7.69 (1H, d, J=2 Hz). LC/MS t=3.95, [MH−] 413, 415.

Examples 14 to 18 were prepared in a similar manner:

Example 14

2-Benzyloxy-5"-fluoro-[1,1';2',1"]terphenyl-2"-carboxylic acid a) 2-Benzyloxy-5"-fluoro[1,1';2',1"]terphenyl-2"-carboxylic acid ethyl ester $^1$H NMR (CDCl$_3$) δ: 0.94 (3H, br s), 3.98 (2H, br s), 4.90 (2H, br q), 6.76-6.79 (3H, m), 6.85-7.42 (12H, m), 7.70 (1H, dd, J=9 Hz).

b) 2-Benzyloxy-5"-fluoro-[1,1';2',1"]terphenyl-2"-carboxylic acid $^1$H NMR (CDCl$_3$) δ: 4.89 (2H, br q), 6.73 (2H, m), 6.80-7.45 (13H, m), 7.74 (1H, dd, J=9 Hz). LC/MS t=3.76, [MH−] 397.

Example 15

2-Benzyloxy-4"-fluoro-[1,1';2',1"]terphenyl-2"-carboxylic acid a) 2-Benzyloxy-4"-fluoro-[1,1';2',1"]terphenyl-2"-carboxylic acid ethyl ester $^1$H NMR (CDCl$_3$) δ: 0.96 (3H, br s), 3.99 (2H, br s), 4.88 (2H, br q), 6.76-6.78 (2H, m), 7.02-7.41(14H, m).

b) 2-Benzyloxy-4"-fluoro-[1,1';2',1"]terphenyl-2"-carboxylic acid $^1$H NMR (CDCl$_3$) δ: 4.91 (2H, br d), 6.71 (1H, d, J=8 Hz), 6.80-7.47 (15H, m). LC/MS t=3.79, [MH−] 397.

Example 16

2"-Benzyloxy-5-fluoro-[1,1';2',1"]terphenyl-3-carboxylic acid a) 2"-Benzyloxy-5-fluoro-[1,1';2',1"]terphenyl-3-carboxylic acid ethyl ester ¹H NMR (CDCl₃) δ: 1.30 (3H, t, J=7 Hz), 4.27 (2H, q, J=7 Hz), 4.72 (2H, br d), 6.76 (1H, d, J=8 Hz), 6.90-6.93 (2H, m), 7.04 (2H, d), 7.16-7.50 (10H, m), 7.63 (1H, s).

b) 2"-Benzyloxy-5-fluoro-[1,1';2',1"]terphenyl-3-carboxylic acid

¹H NMR (CDCl₃) δ: 4.78 (2H br d), 6.77 (1H, d, J=8 Hz), 6.92-7.06 (4H, m), 7.16-7.45 (9H, m), 7.56, (1H, d, J=8 Hz), 7.69 (1H, s). LC/MS t=3.98, [MH−] 397.1.

Example 17

4"-Amino-2-benzyloxy-[1,1';2',1"]terphenyl-3"-carboxylic acid a) 4"-Amino-2-benzyloxy-[1,1';2',1"]terphenyl-3"-carboxylic acid ethyl ester ¹H NMR (CDCl₃) δ: 1.21 (3H, t, J=7 Hz), 4.18, (2H, q, J=7 Hz), 5.62 (2H, br s), 6.39 (1H, d, J=8 Hz), 6.75, (1H, d, J=8 Hz), 6.86-6.96 (2H, m), 7.04 (1H, d, J=7 Hz), 7.16-7.41 (10H, m), 7.71 (1H, d, J=2 Hz). LC/MS t=4.04, [MH+] 424.1.

b) 4"-Amino-2-benzyloxy-[1,1';2',1"]terphenyl-3"-carboxylic acid

¹H NMR (CDCl₃) δ: 4.82 (2H, br s), 5.65 (2H, br s), 6.39 (1H, d, J=8 Hz), 6.76 (1H, d, J=8 Hz), 6.91 (1H, t), 6.96 (1H, dd), 7.06 (2H, d, J=7 Hz), 7.15-7.41 (9H, m), 7.77 (1H, d, J=2 Hz). LC/MS t=3.72, [MH−] 394.2.

Example 18

6"-Acetylamino-2-benzyloxy-[1,1';2',1"]terphenyl-2"-carboxylic acid

LC/MS t=3.38 [MH−] 436.

Example 19

2-Benzyloxy-5-chloro-[1,1';2',1"]terphenyl-2"-carboxylic acid a) 2-Benzyloxy-5-chloro-[1,1';2',1"]terphenyl-2"-carboxylic acid ethyl ester

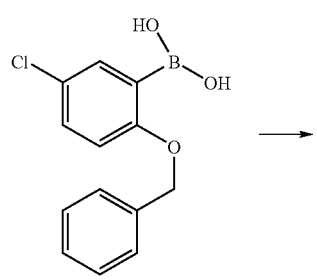

→

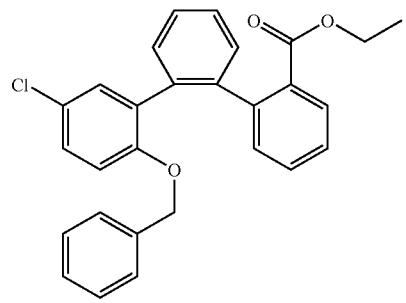

A mixture of 2'-benzyloxy-5'-chlorophenylboronic acid (947 mg, 3.61 mmol), 2'-Bromo-biphenyl-2-carboxylic acid ethyl ester (1.0 g, 3.28 mmol), potassium carbonate (3.39 g, 24.6 mmol), and tetrakis(triphenylphosphine)palladium (0) (379 mg, 0.32 mmol) in 1:1 toluene/ethanol (40 ml) was stirred and heated at 90° C. under nitrogen for 2 hours. After cooling the mixture was diluted with diethyl ether and water. The organic phase was dried and evaporated. The residue was chromatographed eluting with dichloromethane/iso-hexane (1:4 to 1:1) to yield the title compound as a colourless gum (1.28 g, 88%).

¹H NMR (CDCl₃) δ: 0.98(3H, br s), 4.09(2H, br s), 4.77 (2H, m), 6.61(1H, d, J=9 Hz), 7.0-7.4(14H, m), 7.69 (1H, d, J=8 Hz). LC/MS t=4.09.

b) 2-Benzyloxy-5-chloro-[1,1';2',1"]terphenyl-2"-carboxylic acid

The title compound was prepared in a manner similar to 2-benzyloxy-4"-chloro-[1,1';2',1"]terphenyl-2"-carboxylic acid.

¹H NMR (CDCl₃) δ: 4.83(2H, m), 6.58(1H, d, J=9 Hz), 6.95-7.33(14H, m), 7.75(1H, m) LC/MS t=3.79, [MH−] 413.1, 415.1(1×Cl).

Example 20

2-Benzyloxy-[1,1';2',1"]terphenyl-3"-carboxylic acid a) 2-Benzyloxy-[1,1';2',1"]terphenyl-3"-carboxylic acid ethyl ester

2'-Bromobiphenyl-3-carboxylic acid ethyl ester (153 mg, 0.5 mmol) and 2-benzyloxyphenylboronic acid (125 mg 0.55 mmol) were dissolved in 1:1 toluene:ethanol (5 ml) under nitrogen. Potassium carbonate (552 mg, 4 mmol) and tetrakis(triphenylphosphine)palladium(0) (58 mg, 0.05 mmol) were added and the mixture heated at 90° C. for 3 h. After cooling, the solvent was evaporated. The residue was partitioned between diethyl ether and water and the organic phase washed with water, dried (MgSO₄) and the solvent removed in vacuo. The residue was flash chromatographed (silica gel, 2-10% EtOAc-isohexane) to give the title compound as a clear oil (84 mg, 41%). LC/MS R_f=4.09 [(M−OEt)H+]=363.1.

b) 2-Benzyloxy-[1,1';2',1"]terphenyl-3"-carboxylic acid

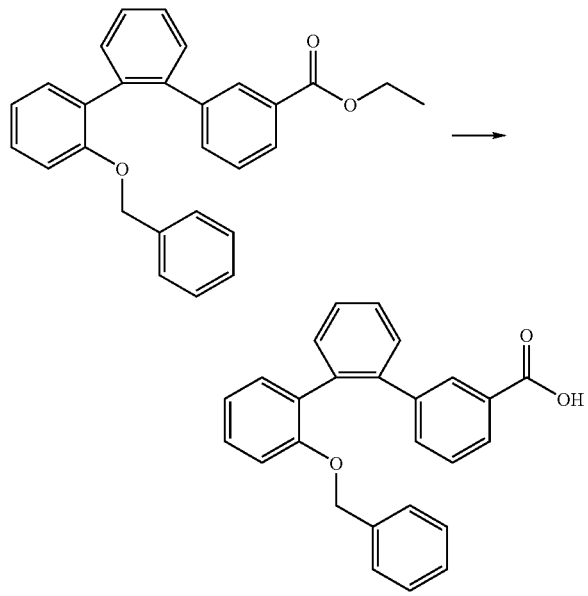

2-Benzyloxy-[1,1';2',1"]terphenyl-3"-carboxylic acid ethyl ester (84 mg, 0.206 mmol) was dissolved in ethanol (2 ml) and 2M sodium hydroxide (0.5 ml) added. The mixture was stirred and heated to 50° C. for 4 h. Water was added and the mixture extracted with isohexane. The aqueous layer was acidified with 2M hydrochloric acid and extracted with diethyl ether (2×10 ml). The combined organic phases were washed with water, dried (MgSO$_4$) and evaporated. The oil was triturated with isohexane and the resulting white solid filtered, washed with isohexane and dried in vacuo. (42 mg, 54%).
$^1$H NMR (CDCl$_3$) δ: 4.72 (2H, d (br)), 6.73 (1H, d, J=8 Hz) 6.92 (1H, t, J=7 Hz), 7.03 (2H, d, J=7 Hz), 7.15-7.26 (7H, m), 7.44 (4H, m), 7.89 (1H, d, J=8 Hz), 7.92 (1H, s).

Example 21

2-Benzyloxy-chloro-[1,1';2',1"]terphenyl-2"-carboxylic acid amide

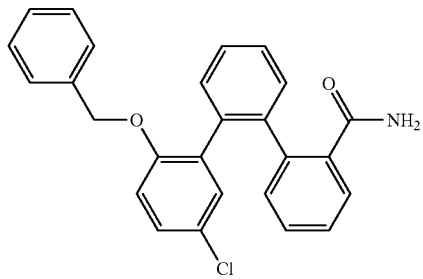

A solution of 2-benzyloxy-5-chloro-[1,1';2',1"]terphenyl-2"-carboxylic acid (100 mg 0.24 mmol) in toluene (1 ml) containing DMF (5 drops) was treated with thionyl chloride (0.035 ml, 0.48 mmol) and heated at 90° C. for 1 hour. After cooling to room temperature the sovent was evaporated. The residue was dissolved in tetrahydrofuran (1 ml), aqueous ammonia (1 ml) was added and the mixture stirred at room temperature for 3 hours. Addition of water (10 ml) gave a precipitate which was filtered off and dried. (74 mg 75%).
$^1$H NMR (DMSO-d$_6$) δ: 5.09(2H, s) 6.75-7.47(18H, m).
LC/MS t=3.57 [MH+] 414.0, 416.0(1Cl).

Example 22

5-(2-Benzyloxy-5-chloro-[1,1';2',1"]terphenyl-3"-yl)-1H-tetrazole a) 2'-Bromo-biphenyl-3-carbonitrile

A mixture of 3-cyanophenylboronic acid (735 mg, 5 mmol), 1,2-dibromobenzene (2.36 g, 10 mmol) potassium carbonate (6.9 g, 50 mmol) and tetrakis(triphenylphosphine)palladium(0) (580 mg, 0.5 mmol) in 1:1 toluene/ethanol (40 ml) was stirred and heated at 90° C. under nitrogen for 3 hours. After cooling the mixture was diluted with diethyl ether and water and the organic phase dried (MgSO$_4$) and evaporated to dryness. The residue was purified by chromatography using Biotage with ethyl acetate/iso-hexane (1:19) to yield the title compound as a white solid (895 mg 69%).
$^1$H NMR (CDCl$_3$) δ: 7.25-7.30 (3H, m), 7.40 (1H, t, J=7 Hz), 7.54 (1H, t, J=7 Hz), 7.65-7.71 (3H, m).

b) 5-(2'-Bromo-biphenyl-3-yl)-1H-tetrazole

A mixture of 2'-bromo-biphenyl-3-carbonitrile (200 mg, 0.77 mmol), sodium azide (66 mg, 1.01 mmol) and triethylamine hydrochloride (139 mg, 1.01 mmol) in toluene (2 ml) was heated at 90° C. for 24 hours. A further portion of sodium azide (66 mg, 1.01 mmol) and triethylamine hydrochloride (139 mg, 1.01 mmol) was added and heated for a further 24 hours. After cooling, the mixture was extracted with water (3×2 ml). The combined extracts were acidified and the precipitate filtered off and dried. (163 mg, 70%).
$^1$H NMR (DMSO-d$_6$) δ: 7.38-7.80(6H, m), 8.06-8.11(2H, m).
LC/MS t=3.82 [MH–] 300.9 (1Br).

c) 5-(2-Benzyloxy-5-chloro-[1,1';2',1"]terphenyl-3"-yl)-1H-tetrazole

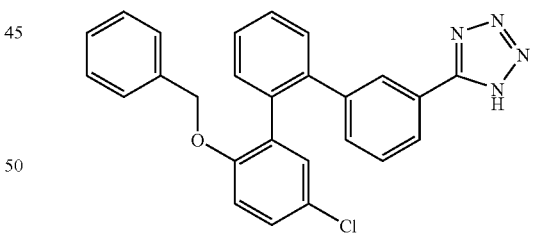

A mixture of 5-(2'-bromo-biphenyl-3-yl)-1H-tetrazole (163 mg, 0.54 mmol), 2-benzyloxy-5-chlorobenzeneboronic acid (156 mg, 0.59 mmol), potassium carbonate (589 mg, 4.33 mmol), and tetrakis(triphenylphosphine)palladium(0) (63 mg, 0.05 mmol) in 1.1 toluene/ethanol (5 ml) was stirred and heated under nitrogen for 16 hours. After cooling the mixture was diluted with dichloromethane and water. The organic phase was dried and evaporated.
The residue was chromatographed eluting with dichloromethane/methanol (95:5) to give the title compound as a colourless solid. (120 mg 51%).
$^1$H NMR (CDCl$_3$) δ: 4.75 (2H, br s), 6.63 (1H, d, J=8 Hz), 6.95-7.50 (14H, m), 7.88 (1H, m), 7.96 (1H, d, J=8 Hz).
LC/MS t=4.22 [MH+] 439.0, 441.0 (1 Cl).

Example 23

N-[1-(2-Benzyloxy-5-chloro-[1,1';2',1"]terphenyl-2"-yl)-methanoyl]-benzenesulfonamide

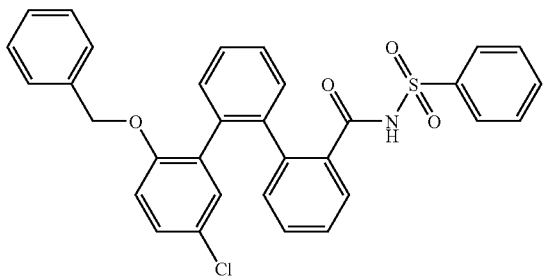

A mixture of 2-benzyloxy-5-chloro-[1,1';2',1"]terphenyl-2"-carboxylic acid (100 mg, 0.24 mmol), benzenesulphonamide (46 mg, 0.29 mmol), EDC (56 mg, 0.29 mmol), and 4-dimethylaminopyridine (5 mg, 0.03 mmol) in 1:1 dichloromethane/tetrahydrofuran (4 ml) was stirred at room temperature for 16 hours. The mixture was diluted with ethyl acetate (10 ml) and washed with aq. sodium bicarbonate (5 ml), dilute hydrochloric acid (5 ml), water (5 ml), and brine (5 ml). The organic phase was dried and evaporated. Purification by prep. HPLC gave the title compound. (27 mg 20%).

$^{1}$H NMR (CDCl$_3$) δ: 5.12(2H, q, J=10 Hz), 6.48(1H, d, J=6 Hz), 6.6-7.8(19H, m), 9.23(1H, br s). LC/MS t=3.98 [MH−] 552.2,554.2 (1 Cl).

Example 24

2-Benzyloxy-[1,1';2',1"]terphenyl-4"-sulfonic acid (1-phenyl-methanoyl)-amide

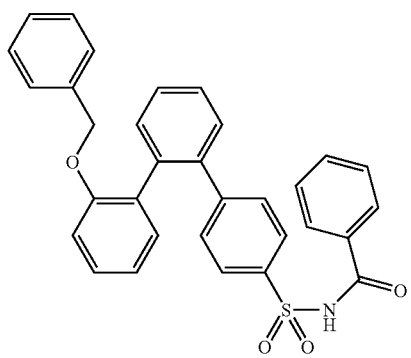

A mixture of 2'-benzyloxy-biphenyl-2-boronic acid (100 mg, 0.33 mmol), 4-bromo-N-(1-phenyl-methanoyl)-benzenesulfonamide (95 mg, 0.28 mmol), potassium carbonate (309 mg, 2.24 mmol), and tetrakis(triphenylphosphine)palladium(0) (38 mg, 0.033 mmol) in 1:1 toluene/ethanol (5 ml) was stirred and heated at 90° C. under nitrogen for 16 hours. After cooling the mixture was diluted with ethyl acetate and water. The organic phase was dried and evaporated. The residue was chromatographed eluting with ethyl acetate/iso-hexane (1:4-1:1) to give the title compound as a colourless solid. (40 mg 23%).

$^{1}$H NMR (CDCl$_3$) δ: 4.6(2H, br d), 6.64(1H, d, J=8 Hz), 6.9-7.8(17H, m), 7.79(2H, d, J=8 Hz), 7.83(2H, d, J=8 Hz), 9.0(1H, br s). LC/MS t=4.09 [MH+] 520.1.

Examples 25 and 26 were prepared in a similar manner:

Example 25

2-Benzyloxy-[1,1';2',1"]terphenyl-4"-sulfonic acid [1-(4-nitro-phenyl)-methanoyl]-amide

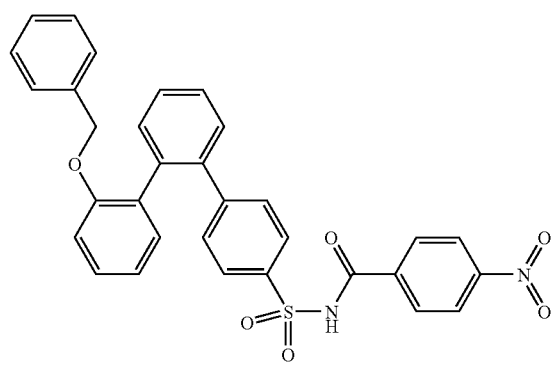

$^{1}$H NMR (CDCl$_3$) δ: 4.6(2H, br s), 6.59(1H, d, J=8 Hz), 6.8-7.9(20H, m). LC/MS t=4.57 [MH−] 563.

Example 26

2-Benzyloxy-[1,1';2',1"]terphenyl-3"-sulfonic acid acetyl-amide

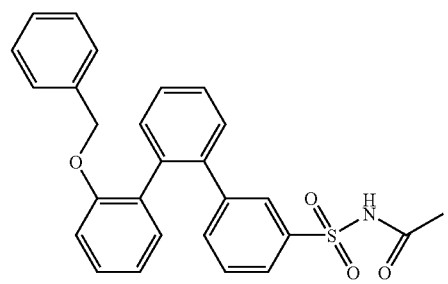

$^{1}$H NMR (CDCl$_3$) δ: 2.04(3H, s), 4.7(2H, br d), 6.70(1H, d, J=8 Hz), 6.92-7.46(14H, m), 7.74(1H, s), 7.84(1H, d, J=8 Hz), 8.1(1H, br s). LC/MS t=3.64 [MH−] 456.

Preparation of Intermediates

2-Benzyloxy-5-chloro-phenyl-boronic acid

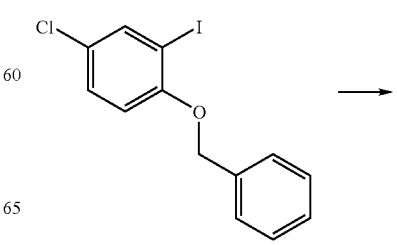

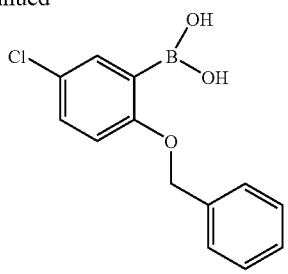

Butyllithium (11.5 ml, 28.7 mmol, 2.5 M) was added, under nitrogen, over 10 minutes, to a solution of 2-benzyloxy-5-chloro-iodobenzene (9 g, 26.2 mmol) in THF (40 ml) at −100° C. The reaction mixture was then warmed up at −78° C. and stirred for 1 hour (at −78° C.) before triisopropyl borate (18 ml, 78.4 mmol) was added over 10 minutes. The reaction mixture was then warmed to room temperature before a solution of HCl (60 ml, 1M) was added. The mixture was vigorously stirred for 1½ hours. The organic phase was separated, washed sequentially with water and brine, dried (MgSO$_4$) filtered and concentrated. The residue was triturated with a 30% solution of ether in iso-hexane and filtered to give the title compound (3.62 g, 53%) as a white solid.

$^1$H NMR(CDCl$_3$) δ 5.12(2H, s), 5.74(2H, s), 6.91(1H, d), 7.26(1H, s), 7.35-7.41(5H, m), 7.81(1H, s).

5-Chloro-2-hydroxy-[1,1';2',1"]terphenyl-3"-carboxylic acid ethyl ester

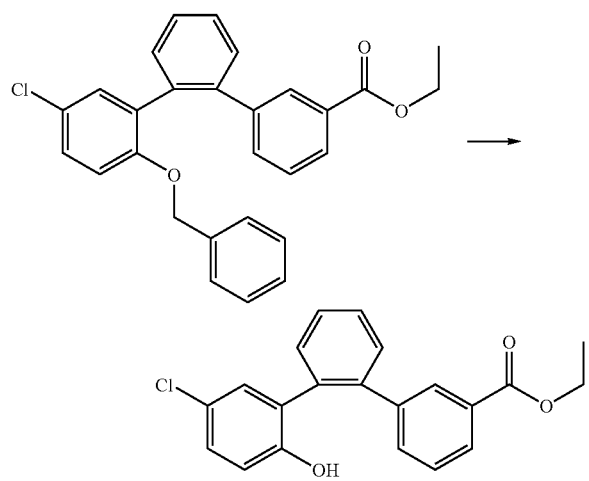

HBr (48% solution in acetic acid, 20 ml) was added to a solution of 2-benzyloxy-5-chloro-[1,1',2,2"]terphenyl-3"-carboxylic acid ethyl ester (690 mg, 1.5 mmol) in acetic acid (4 ml). The reaction mixture was stirred at room temperature for 30 minutes, then diluted with water and extracted with ether. The organic phase was washed with a saturated solution of NaHCO$_3$, dried (MgSO$_4$) and evaporated. The residue was redissolved in ethanol and a 30% aqueous ammonia solution (2 ml) was added. The reaction mixture was stirred overnight, concentrated in vacuo to an oil that was purified by chromatography, using Biotage®, with 15% of ethyl acetate in iso-hexane to yield the title compound (340 mg, 62%) as a yellow solid.

$^1$H NMR (CDCl$_3$) δ 1.36 (3H, t), 4.33(2H, q), 6.68(1H, d), 7.08-7.93(10H, m).

General Procedure A—Alkylation

5-Chloro-2-(3-methyl-butoxy)-[1,1';2',1"]terphenyl-3"carboxylic acid ethyl ester

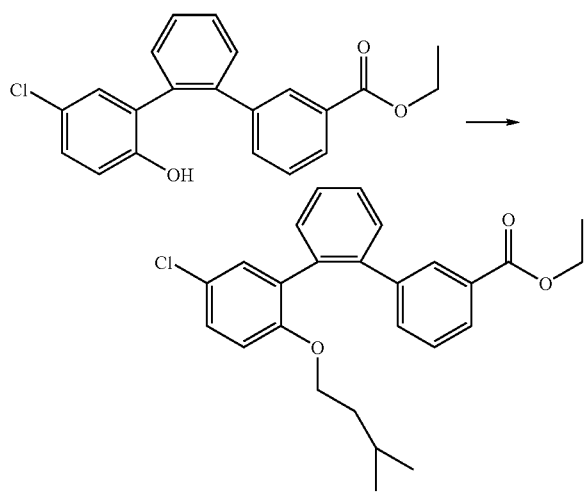

A mixture of 5-chloro-2-hydroxy-[1,1';2',1"]terphenyl-3"-carboxylic acid ethyl ester (50 mg, 0.14 mmol), potassium carbonate (48 mg, 0.35 mmol), and 1-bromo-3-methylbutane (23.5 mg, 0.15 mmol) was heated in N,N'-dimethylformamide (3 ml) at 90° C. for 4 hours. The reaction mixture was then poured into water and extracted with ethyl acetate; the organic layers were dried over MgSO$_4$ and evaporated. The residue was chromatographed through a SPE column using 10% ethyl acetate in iso-hexane as eluent to yield the title compound as a white solid (45 mg, 75%).

$^1$H NMR(CDCl$_3$) δ 0.76(6H, d), 1.24-1.45 (6H, m), 3.24-3.70(2H, br ) 4.32 (2H, br q), 6.58(1H, d), 7.13-7.43(8H, m), 7.85(1H, d), 7.91(1H, s).

5-Chloro-2-cyclopentylmethoxy-[1,1';2',1"]terphenyl-3"carboxylic acid ethyl ester General procedure A was employed to synthesise 5-chloro-2-cyclopentylmethoxy-[1,1';2',1"]terphenyl-3"carboxylic acid ethyl ester using the toluene 4-sulfonic acid cyclopentyl methyl ester.

The toluene 4-sulfonic acid cyclopentyl methyl ester was prepared by adding p-Toluenesulfonyl chloride (3.6 mmol, 684 mg) to a solution of cyclopentanemethanol (3 mmol, 300 mg) and pyridine (3 ml) in dichloromethane (3 ml). The resulting mixture was stirred for 2½ hours at room temperature, then diluted with dichloromethane and washed sequentially with HCl (1M solution) and a saturated solution of Na$_2$CO$_3$. The organic layer was then dried over MgSO$_4$ and evaporated to give the toluene-4-sulfonic acid cyclopentyl methyl ester. $^1$H NMR (CDCl$_3$) δ 1.17(2H, m), 1.53(4H, m), 1.69(2H, m), 2.20(1H, m), 2.45(3H, s), 3.89(2H, d), 7.34(2H, d), 7.78(2H, d).

The following intermediates were prepared following General Procedure A using the appropriate bromide as alkylating agent (all commercially available). $^1$H NMR spectra were recorded in CDCl$_3$ solution.

| COMPOUND NAME | ¹H NMR |
|---|---|
| 5-Chloro-2-(4-fluoro-benzyloxy)-[1,1';2',1"]terphenyl-3"carboxylic acid ethyl ester | 1.32(3H, t), 4.12(2H, br.q), 4.52-4.82(2H, br.d), 6.59(1H, d), 6.91(2H, d), 7.11-7.87(12H, m). |
| 5-Chloro-2-(2,4-difluoro-benzyloxy)-[1,1';2',1"]terphenyl-3"-carboxylic acid ethyl ester | 1.33(3H, t), 4.12(2H, br.q), 4.52-4.80(2H, br.d), 6.64(1H, d), 6.70-7.87(13H, m). |
| 5-Chloro-2-(4-chloro-benzyloxy)-[1,1';2',1"]terphenyl-3"carboxylic acid ethyl ester | 1.31(3H, t), 4.26(2H, br.q), 4.42-4.78(2H, br.d), 6.56(1H, d), 6.86(1H, d), 7.11-7.87(13H, m). |
| 5-Chloro-2-(2-fluoro-4-chloro-benzyloxy)-[1,1';2',1"]terphenyl-3"carboxylic acid ethyl ester | 1.32(3H, t), 4.12(2H, br.q), 4.45-4.81(2H, br.s), 6.61(1H, d), 6.74(1H, t), 6.99(2H, t), 7.14-7.87(10H, m). |
| 5-Chloro-2-(4-isobutoxy)-[1,1';2',1"]terphenyl-3"-carboxylic acid ethyl ester | 0.75(6H, d), 1.35(3H, t), 1.75-1.80(1H, m), 3.34(2H, br.s), 4.32(2H, q), 6.62(1H, d), 7.09-7.43(8H, m), 7.85(1H, d), 7.89(1H, s) |
| 5-Chloro-2-(pyridin-2-ylmethoxy)-[1,1';2',1"]terphenyl-3"carboxylic acid ethyl ester | 1.30(3H, t), 4.25(2H, q), 4.55-4.89(2H, br.s), 6.58(1H, d), 6.73(1H, d), 7.11-7.87(12H, m), 8.47(1H, d). |
| 5-Chloro-2-(pyridin-4-ylmethoxy)-[1,1';2',1"]terphenyl-3"carboxylic acid ethyl ester | 1.30(3H, t), 4.25(2H, br. s), 4.55-4.89(2H, br.d), 6.53(1H, d), 6.84(2H, d), 7.13-7.48(8H, m), 7.80(1H, s), 7.86(1H, d) 8.46(2H, d). |
| 5-Chloro-2-(pyridin-3-ylmethoxy)-[1,1';2',1"]terphenyl-3"carboxylic acid ethyl ester | 1.32(3H, t), 4.28(2H, br.q), 4.40-4.90(2H, br.d), 6.63(1H, d), 7.14-7.85(12H, m), 8.30(1H, s) 8.49(1H, d). |
| 5-Chloro-2-cyclohexylmethoxy-[1,1';2',1"]terphenyl-3"carboxylic acid ethyl ester | 0.75-1.72(14H, br. m), 3.28(2H, br.s), 4.32(2H, q), 6.62(1H, d), 7.11-7.44(8H, m), 7.85(1H, d), 7.91(1H, s). |
| 5-Chloro-2-(thiophen-3-ylmethoxy)-[1,1';2',1"]terphenyl-3"carboxylic acid ethyl ester | 1.33(3H, t), 4.28(2H, br.q), 4.50-4.82(2H, br.d), 6.64(1H, d), 6.75(1H, d), 6.84(1H, d), 7.11-7.86(11H, m). |
| 5-Chloro-2-(thiophen-2-ylmethoxy)-[1,1';2',1"]terphenyl-3"carboxylic acid ethyl ester | 1.34(3H, t), 4.30(2H, q), 4.71-4.84(2H, br.s), 6.71(1H, d), 6.77-7.85(13H, m). |
| 5-Chloro-2-cyclopentylmethoxy-[1,1';2',1"]terphenyl-3"carboxylic acid ethyl ester | 0.87-1.58(11H, m), 2.05(1H, m), 3.46(2H, br.s), 4.32(2H, q), 6.63(1H, d), 7.08-7.43(7H, m), 7.78(1H, d), 7.85(1H, d), 7.90(1H, s). |
| 5-Chloro-2-propoxy-[1,1';2',1"]terphenyl-3"carboxylic acid ethyl ester | 0.74(3H, t), 1.25(3H, t), 1.47(2H, m), 3.30-3.75(2H, br.d), 4.31(2H, q), 6.58(1H, d), 7.11-7.43(8H, m), 7.85(1H, s), 7.89(1H, s). |
| 2-Butoxy-5-chloro-[1,1';2',1"]terphenyl-3"carboxylic acid ethyl ester | 0.78(3H, t), 0.79-0.88(1H, m), 1.15-1.21(1H, m), 1.34(3H, t), 1.39-1.44(2H, m), 3.29-3.75(2H, br.d), 4.29(2H, q), 6.70(1H, d), 7.08-7.42(8H, m), 7.79-7.83(2H, m). |
| 5-Chloro-2-isopropoxy-[1,1';2',1"]terphenyl-3"carboxylic acid ethyl ester | 0.77-1.1(6H, br.s), 1.34(3H, t), 4.14(1H, m), 4.32(2H, q), 6.58(1H, d), 7.11-7.43(8H, m), 7.85(1H, d), 7.90(1H, s). |

General Procedure B—Mitsunobu Reaction

5-Chloro-2-phenethyloxy-[1,1';2',1"]terphenyl-3"-carboxylic acid ethyl ester

A mixture of 5-chloro-2-hydroxy-[1,1';2',1"]terphenyl-3"-carboxylic acid ethyl ester (100 mg, 0.28 mmol), phenethyl alcohol (31 mg, 0.25 mmol), triphenyl phosphine (74 mg, 0.28 mmol), diisopropyl azodicarboxylate (57 mg, 0.28 mmol) in THF (6 ml) was stirred at room temperature overnight. The mixture was then poured into water and extracted with ether, the organic layers were dried over MgSO$_4$ and evaporated. The residue was chromatographed through an SPE column using iso-hexane to yield the title compound (95 mg, 80%) as an oil.

¹H NMR (CDCl$_3$) δ 1.32(3H, t), 2.74(2H, t), 3.41-3.92(2H, br. d), 4.30(2H, q), 6.54(1H, d), 6.93-7.90(15 H, m).

General Procedure C—Ester Deprotection

Example 27

5-Chloro-2-(3-methyl-butoxy)-[1,1';2',1"]terphenyl-3"-carboxylic acid

5-Chloro-2-(3-methyl-butoxy)-[1,1';2',1"]terphenyl-3"-carboxylic acid ethyl ester (45 mg, 0.106 mmol) and NaOH (excess) were heated at 60° C. in ethanol (3 ml) for 2 hrs. The mixture was then cooled to room temperature, diluted with water, acidified with HCl (1M solution) and extracted with ethyl acetate. The combined extracts were dried (MgSO$_4$) and evaporated to yield the title compound (41 mg, 98%) as a white solid.

¹H NMR(CDCl₃) δ 0.78(6H, d), 1.35(2H, m), 1.44-1.49 (1H, m), 3.2-3.7(2H, br.s), 6.61(1H, d), 7.14-7.43(8H, m), 7.91(1H, d), 8.02(1H, s). LC/MS R$_t$=4.13 min. m/z [MH⁻] 393, 395

The following Examples 28-42 were prepared from the appropriate ester by methods analogous to General Procedure C. ¹H NMR spectra were recorded in CDCl₃ solution.

| EXAMPLE | COMPOUND NAME | LC/MS | ¹H NMR |
|---|---|---|---|
| 28 | 5-Chloro-2-(4-fluoro-benzyloxy)-[1,1';2',1'']terphenyl-3''carboxylic acid | R$_t$ = 3.97 min. [MH⁻] 431, 433 | 4.52-4.82(2H, br.d), 6.61(1H, d), 6.92-7.90(14H, m). |
| 29 | 5-Chloro-2-(2,4-difluoro-benzyloxy)-[1,1';2',1'']terphenyl-3''-carboxylic acid | R$_t$ = 3.99 min. [MH⁻] 449, 451 | 4.52-4.80(2H, br.s), 6.67(1H, d), 6.69-7.50(11H, m), 7.90(1H, s), 7.93(1H, s) |
| 30 | 5-Chloro-2-(4-chloro-benzyloxy)-[1,1';2',1'']terphenyl-3''carboxylic acid | R$_t$ = 4.12 min. [MH⁻] 447, 449 | 4.42-4.78(2H, br.d), 6.59(1H, d), 6.90(1H, d), 7.12-7.92(13H, m). |
| 31 | 5-Chloro-2-(2-fluoro-4-chloro-benzyloxy)-[1,1';2',1'']terphenyl-3''carboxylic | R$_t$ = 4.15 min. [MH⁻] 465, 467 | 4.45-4.81(2H, br.s), 6.64(1H, d), 6.80(1H, t), 7.0(2H, d), 7.14-7.93(10H, m). |
| 32 | 5-Chloro-2-(4-isobutoxy)-[1,1',2',1''] terphenyl-3''-carboxylic acid | R$_t$ = 4.05 min. [MH⁻] 379, 381 | 1.75-1.85(1H, m), 3.39(2H, br. s), 6.64(1H, d), 7.06-7.43(8H, m), 7.90(1H, d), 7.99(1H, s) |
| 33 | 5-Chloro-2-(pyridin-2-ylmethoxy)-[1,1';2',1''] terphenyl-3''carboxylic acid | R$_t$ = 3.61 min. [MH⁺] 416, 418 | 4.61(1H, br.s), 4.87(1H, br.s), 6.61(1H, d), 6.88(1H, d), 7.13-7.91(12H, m), 8.51(1H, br. s). |
| 34 | 5-Chloro-2-(pyridin-4-ylmethoxy)-[1,1';2',1''] terphenyl-3''carboxylic acid | R$_t$ = 3.37 min. [MH⁺] 416, 418 | |
| 35 | 5-Chloro-2-(pyridin-3-ylmethoxy)-[1,1';2',1''] terphenyl-3''carboxylic acid | R$_t$ = 3.47 min. [MH⁺] 416, 418 | 4.19(1H, br. s), 4.79(1H, br.s), 6.62(1H, d), 7.06-7.88(12H, m), 8.35(1H, br. s) 8.50(1H, br. s). |
| 36 | 5-Chloro-2-cyclohexylmethoxy-[1,1';2',1'']terphenyl-3''carboxylic acid | R$_t$ = 4.33 min. [MH⁺] 421 | 0.74-1.60(11H, br. m), 3.38(2H, br.s), 6.63(1H, d), 7.08-7.43(8H, m), 7.91(1H, d), 8.02(1H, s). |
| 37 | 5-Chloro-2-(thiophen-3-ylmethoxy)-[1,1';2',1''] terphenyl-3''carboxylic acid | R$_t$ = 3.91 min. [MH⁻] 419, 421 | 4.55-4.85(2H, br.d), 6.66(1H, d) 6.76(1H, d), 6.87(1H, s), 7.12-7.92(11H, m). |
| 38 | 5-Chloro-2-(thiophen-2-ylmethoxy)-[1,1';2',1''] terphenyl-3''carboxylic acid | R$_t$= 3.89 min. [MH⁻] 419, 420 | 4.84(2H, br.s), 6.73(1H, d), 6.79-7.92(13H, m). |
| 39 | 5-Chloro-2-cyclopentylmethoxy-[1,1';2',1'']terphenyl-3''carboxylic acid | R$_t$ = 4.22 min. [MH⁻] 405, 407 | 0.83-1.62(8H, br. m), 2.07(1H, m), 3.51(2H, br.s), 6.65(1H, d), 7.06-7.44(8H, m), 7.90(1H, d), 7.99(1H, s), |
| 40 | 5-Chloro-2-propoxy [1,1';2',1''] terphenyl-3''carboxylic acid | R$_t$ = 3.92 min. [MH⁻] 365, 367 | 0.77(3H, t), 1.50(2H, m), 3.30-3.70(2H, br.d), 6.61(1H, d), 7.13-7.44(8H, m), 7.90(1H, s), 8.00(1H, s). |
| 41 | 2-Butoxy-5-chloro-[1,1';2',1''] terphenyl-3''carboxylic acid | R$_t$ = 4.03 min. [MH⁻] 379, 381 | 0.81(3H, t), 1.16-1.25(2H, m), 1.42-1.49(2H, m), 3.29-3.75(2H, br.s), 6.61(1H, d), 7.12-7.45(8H, m), 7.91(1H, s), 8.02(1H, s). |
| 42 | 5-Chloro-2-isopropoxy-[1,1';2',1'']terphenyl-3''carboxylic acid | R$_t$ = 3.87 min. [MH⁻] 365, 367 | 0.73-0.93(6H, br.s), 4.14(1H, m), 6.81(1H, d), 7.16-7.46(9H, m), 7.77(1H, br. s), |

Example 43

5-Chloro-2-isobutoxy-[1,1';2',1"]terphenyl-2"-carboxylic acid a) 2'-Bromo-biphenyl-2-carboxylic acid ethyl ester

Prepared using the same conditions for the synthesis of 2'-bromo-biphenyl-3-carboxylic acid ethyl ester substituting 3-ethoxycarbonylphenyl boronic acid with 2-ethoxycarbonylphenylphenyl boronic acid.

$^1$H NMR (CDCl$_3$) δ 1.01 (3H, t, J=7 Hz), 4.10 (2H, m), 7.19-7.26 (3H, m), 7.33 (1H, t, J=7 Hz), 7.48 (1H, t, J=7 Hz), 7.55-7.62 (2H, m), 8.04 (1H, d, J=8 Hz).

b) 5-Chloro-2-hydroxy-[1,1';2',1"]terphenyl-2"-carboxylic acid ethyl ester Prepared using the same conditions used for the synthesis of 5-chloro-2-hydroxy-[1,1';2',1"]terphenyl-3"-carboxylic acid ethyl ester except 2-benzyloxy-5-chloro-[1,1',2,2']terphenyl-2"-carboxylic acid ethyl ester was used instead of 2-benzyloxy-5-chloro-[1,1',2,2']terphenyl-3"-carboxylic acid ethyl ester.

$^1$H NMR (CDCl$_3$) δ 1.24 (3H, t), 4.23(2H, q), 6.59(1H, d), 7.04-7.47(9H, m), 7.82(1H, dd).

c) 5-Chloro-2-isobutoxy-[1,1';2',1"]terphenyl-2"-carboxylic acid ethyl ester Prepared as in procedure A from 5-chloro-2-hydroxy-[1,1';2',1"]terphenyl-2"-carboxylic acid ethyl ester and 1-bromo-2-methyl-propane.

$^1$H NMR (CDCl$_3$) δ 0.85(6H, br. s), 1.04(3H, t), 1.91(1H, m), 3.49(2H, br. s), 4.07(2H, br. m), 6.63(1H, d), 7.03-7.37 (9H, m), 7.71(1H, d).

d) 5-Chloro-2-isobutoxy-[1,1';2',1"]terphenyl-2"-carboxylic acid

Prepared as in procedure C from 5-chloro-2-isobutoxy-[1, 1';2',1"]terphenyl-2"-carboxylic acid ethyl ester.

$^1$HNMR (CDCl$_3$) δ 0.78(6H, br. t), 1.88(1H, m), 3.49(2H, br. d), 6.63(1H, d), 7.07-7.41(9H, m), 7.79(1H, d). LC/MS R$_t$=3.91(100%) [M$^{-1}$ $^{m/z}$ 379, 381.

General Procedure D—Standard Hydrolysis Procedure

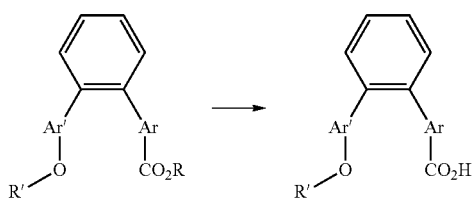

The ester (0.5 mmol) was dissolved in methanol or ethanol (2 ml) and 2M sodium hydroxide (1 ml) added. The mixture was stirred at from room temperature to reflux for from 30 minutes to 20 hours until the reaction was complete by tlc. The solution was diluted with water then extracted with isohexane or diethyl ether and acidified to pH4 with either hydrochloric acid or acetic acid. The mixture was extracted with diethyl ether or dichloromethane. The organic solution was dried over magnesium sulphate and evaporated to give the title compound.

General Procedure E—Preparation of Boronic Acid Intermediates

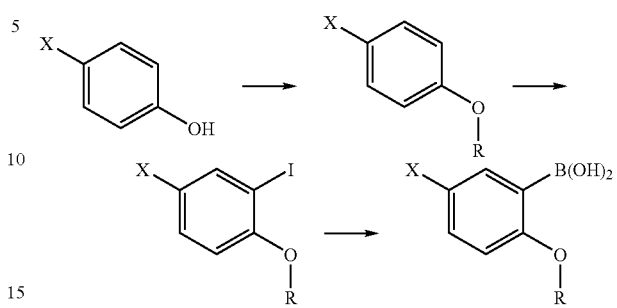

E(i) 4-(Benzyloxy)benzotrifluoride

A solution of 4-hydroxybenzotrifluoride (8.55 g, 52.78 mmol) in acetone (200 ml) was treated with benzyl bromide (9.87 g, 6.86 ml, 58.05 mmol) and potassium carbonate (10.94 g, 79.16 mmol). The mixture was stirred and heated to reflux under nitrogen for 3 h. After cooling, diethyl ether (400 ml) and water (400 ml) were added and the aqueous phase re-extracted with diethyl ether (100 ml). The combined organic layers were washed with water, dried (MgSO$_4$) and the solvent removed in vacuo to leave the title compound as a white solid. (12.71 g, 95%)

$^1$H NMR (CDCl$_3$) δ: 5.11 (2H, s), 7.03 (2H, d, J=9 Hz), 7.34-7.44 (5H, m), 7.55 (2H, d, J=9 Hz).

E(ii) 2-Benzyloxy-5(trifluoromethyl)iodobenzene

A solution of 4(benzyloxy)benzotrifluoride (12.71 g, 50.4 mmol) in acetonitrile (300 ml) was stirred under nitrogen and 1-(chloromethyl)-4-fluoro-1,4-diazoniabicyclo[2.2.2]octane bis(tetrafluoroborate) (17.75 g, 50.4 mmol) and iodine (6.4 g, 25.2 mmol) added. The mixture was stirred at room temperature for 88 h. The solvent was evaporated and the residue partitioned between ethyl acetate (400 ml) and water (400 ml). The organic layer was washed with water, dried (MgSO$_4$) and evaporated to an orange oil which was purified by flash chromatography (silica gel, 5% ethyl acetate:isohexane) to give the title compound as an orange oil (15.07 g, 79%)

$^1$H NMR (CDCl$^3$) δ: 5.21 (2H, s), 6.89 (1H, d J=9 Hz), 7.32-7.55 (6H, m), 8.04 (1H, d, J=2 Hz).

E(iii) 2-Benzyloxy-5-(trifluoromethyl)benzeneboronic acid

A solution of 4-benzyloxy-3-iodobenzotrifluoride (15.07 g, 39.85 mmol) in tetrahydrofuran (200 ml) was cooled to −40° C. with stirring under nitrogen. 2M isopropylmagnesium chloride in diethyl ether (39.85 ml, 79.7 mmol) was added dropwise and the mixture stirred at −40° C. for 40 minutes, then cooled to −75° C. Trimethyl borate (8.3 g, 9.2 ml, 79.7 mmol) was added at −75° C. over 10 minutes and the reaction stirred and allowed to reach 0° C. over 1 h. 1M hydrochloric acid (200 ml) was added and the mixture stirred vigorously for 1 h.

The layers were separated and the aqueous layer extracted with diethyl ether (100 ml). The combined organic layers were washed with water, dried (MgSO$_4$) and evaporated. The residue was flash chromatographed (silica gel, 5-20% ethyl acetate:isohexane) to give the title compound as a white solid. (7.71 g, 65%).

$^1$H NMR (CDCl$_3$) δ: 5.20 (2H, s), 5.79 (2H, s), 7.05 (1H, d, J=9 Hz), 7:39-7.44 (5H, m), 7.68 (1H, dd J=2 Hz, J=9 Hz), 8.15 (1H, d, J=2 Hz).

The following intermediates were prepared using analogous procedures.

4-[(4-Fluorobenzyl)oxy]benzotrifluoride

Prepared by general procedure E(i) but using 4-fluorobenzyl bromide instead of benzyl bromide.

$^1$H NMR (CDCl$_3$): δ: 5.07 (2H, s), 7.02 (2H, d, J=9 Hz), 7.07-7.11 (2H, m), 7.39-7.42 (2H, m), 7.52 (2H, d, J=9 Hz)

2-[(4-Fluorobenzyl)oxy]-5-trifluoromethyliodobenzene

Prepared by general procedure E(ii) but using 4-[(4-fluorobenzyl)oxy]benzotrifluoride instead of 4-(benzyloxy)benzotrifluoride.

$^1$H NMR (CDCl$_3$) δ: 5.16 (2H, s), 6.88 (1H, d, J=9 Hz), 7.08-7.13 (2H, m), 7.44-7.48 (2H, m), 7.54-7.57 (1H, dd, J=2 Hz, J=9 Hz), 8.04 (1H, d, J=2 Hz).

2-[(4-Fluorobenzyl)oxy]-5-trifluoromethylbenzeneboronic acid

Prepared by general procedure E(iii) but using 4-[(4-fluorobenzyl)oxy]-3-iodobenzotrifluoride instead of 4-benzyloxy-3-iodobenzotrifluoride.

$^1$H NMR (d$_6$DMSO) δ 5.22 (2H, s), 7.20-7.26 (3H, m), 7.54-7.58 (2H, m), 7.71 (1H, d, J=9 Hz), 7.75 (1H, s), 8.03 (2H, s).

4-[(2,4-Difluorobenzyl)oxy]benzotrifluoride

Prepared by general procedure E(i) but using 2,4-difluorobenzyl bromide instead of benzyl bromide.

$^1$H NMR (CDCl$_3$) δ5.12 (2H, s), 6.89 (2H, dt, J=2 Hz, J=9 Hz), 7.02-7.05 (2H, d, J=9 Hz), 7.33-7.49 (1H, q, J=8 Hz, J=15 Hz), 7.56 (2H, d, J=9 Hz)

2-[(2,4-Difluorobenzyl)oxy]-5-trifluoromethyliodobenzene

Prepared by general procedure E(ii) but using 4-[(2,4-difluorobenzyl)oxy]benzotrifluoride instead of 4-(benzyloxy)benzotrifluoride.

$^1$H NMR (CDCl$_3$): δ: 5.21 (2H, s), 6.84-6.95 (3H, m), 7.55-7.65 (2H, m), 8.04 (1H, s)

2-[(2.4-Difluorobenzyl)oxy]-5-trifluoromethylbenzeneboronic acid

Prepared by general procedure E(iii) but using 4-[(2,4-difluorobenzyl)oxy]-3-iodobenzotrifluoride instead of 4-benzyloxy-3-iodobenzotrifluoride.

$^1$H NMR (d$_6$DMSO) δ 5.26 (2H, s), 7.16 (1H, dt, J=2 Hz, J=9 Hz) 7.27 (1H, d, J=9 Hz), 7.33 (1H, dt, J=2 Hz, J=9 Hz), 7.68-7.75 (3H, m), 8.01 (2H, s).

2-Benzyloxy-5-bromoiodobenzene

Prepared as general procedure E(i) from 2-iodo-4-bromophenol $^1$H NMR (CDCl$_3$) δ 5.10(2H, s), 6.69(1H, d, J=9 Hz), 7.23-7.46(6H, m), 7.88(1H, s).

2-Benzyloxy-5-bromobenzeneboronic acid

Prepared as general procedure E(iii) from 2-benzyloxy-5-bromoiodobenzene.

$^1$H NMR (CDCl$_3$) δ 5.12(2H, s), 5.78(2H, s), 6.58(1H, d, J=9 Hz), 7.34-7.39(5H, m), 7.40(1H, d, J=9 Hz), 7.95(1H, s). LC/MS: Rt=3.44 [M–H] 305, 307 (1 Br)

2-(4-Fluorobenzyl)oxy-5-bromoiodobenzene

Prepared as general procedure E(i) from 2-iodo-4-bromophenol.

$^1$H NMR (CDCl$_3$) δ 5.06(2H, s), 6.69(1H, d, J=9 Hz), 7.07-7.10(2H, m), 7.35-7.45(3H, m), 7.89(1H, s).

2-(4-Fluorobenzyl)oxy-5-bromobenzeneboronic acid

Prepared as general procedure E(iii) from 2-(4-fluorobenzyl)oxy-5-bromoiodobenzene.

$^1$H NMR (CDCl$_3$) δ 5.07(2H, s), 5.83(2H, s), 6.84(1H, d, J=9 Hz), 7.10(2H, m), 7.37(2H, m), 7.50(1H, d, J=9 Hz), 7.95(1H, s).

2-(2,4-Difluorobenzyl)oxy-5-bromoiodobenzene

Prepared as general procedure E(i) from 2-iodo-4-bromophenol.

$^1$H NMR (CDCl$_3$) δ 5.12(2H, s), 6.74-6.95(3H, m), 7.40 (1H, d, J=9 Hz), 7.57-7.63(1H, m), 7.90(1H, s).

2-(2,4-Difluorobenzyl)oxy-5-bromobenzeneboronic acid

Prepared as general procedure E(iii) from 2-(2,4-difluorobenzyl)oxy-5-bromoiodobenzene.

$^1$HNMR (CDCl$_3$) δ 5.14(2H, s), 5.77(2H, br s), 6.86-6.95 (3H, m), 7.36-7.42(1H, m), 7.52(1H, d, J=9 Hz), 7.95(1H, s).

2-[(4-Fluorobenzyl)oxy]-5-chloroiodobenzene

Prepared as general procedure E(i) from 2-iodo-5-chlorophenol.

$^1$HNMR (CDCl$_3$) δ 5.08(2H, s), 6.75(1H, d, J=8 Hz), 7.06 (1H, d, J=8 Hz), 7.07(1H, d, J=8 Hz), 7.23(1H, s), 7.43-7.46 (2H, m), 7.76(1H, s).

2-[(4-Fluorobenzyl)oxy]-5-chlorobenzeneboronic acid

Prepared as general procedure E(iii) from 2-[(4-fluorobenzyl)oxy]-5-chloroiodobenzene $^1$H NMR (CDCl$_3$) δ 5.07(2H, s), 6.89(1H, d, J=8 Hz), 7.09(2H, m), 7.35-7.40(3H, m), 7.81(1H, s).

Ethyl 2-bromo-4-chlorobenzoate

A mixture of 2-bromo-4-chlorobenzoic acid (235 mg, 1 mmol) and thionyl chloride (238 mg, 146 ul, 2 mmol) in toluene (5 ml) was heated at 90° C. for 1 hour. The reaction mixture was cooled and the solvent evaporated. The residue was dissolved in THF (1 ml) and treated with ethanol (1 ml). The solution was evaporated to dryness leaving the title compound as a yellow oil 263 mg 100%

NMR (CDCl$_3$): δ: 1.41(3H, t, J=7 Hz), 4.40(2H, q, J=7 Hz), 7.28-7.32(1H, m), 7.57-7.60(1H, m), 7.90(1H, s).

Ethyl 2-bromo-5-chlorobenzoate

A solution of 2-bromo-5-chlorobenzoic acid in ethanol (10 ml) and sulphuric acid (0.5 ml) was refluxed for 20 hours then cooled and evaporated. The residue was dissolved in diethyl ether/water and the organic layer dried (magnesium sulphate) and evaporated to give 516 mg of light brown oil.

$^1$H NMR (CDCl$_3$) δ: 1.41 (3H, t), 4.40 (2H, q), 7.30 (1H, dd), 7.58, (1H, d), 7.65 (1H, d).

Ethyl 3-bromo-5-fluorobenzoate

Sulphuric acid (0.5 mL) was added to a stirring solution of 3-bromo-5-fluorobenzoic acid (473 mgs, 2.16 mmol) in ethanol (10 mL) and refluxed for 17 hours. The reaction mixture was cooled to room temperature and diluted with diethyl ether and water. The ether layer was washed with 5% sodium hydrogen carbonate solution, dried over magnesium sulphate and evaporated to dryness to give the title compound as a brown oil. (506 mg).

$^1$H NMR (CDCl$_3$) δ: 1.40 (3H, t, J=7 Hz), 4.39 (2H, q, J=7 Hz), 7.43 (1H, td, J=2 Hz, J=8 Hz), 7.67 (1H, dd, J=2 Hz, J=8 Hz), 7.98 (1H, s).

t-Butyl 3-bromo-5-iodobenzoate

A mixture of 3-bromo-5-iodobenzoic acid (50 g, 153 mmol), 1-(3-dimethylaminopropyl)-ethylcarbodiimide hydrochloride (30.8 g, 153 mmol), 4-dimethylaminopyridine (18.6 g, 153 mmol) and t-butanol (69.4 g, 90 ml, 153 mmol) in dichloromethane (500 ml) was stirred at room temperature overnight. The reaction mixture was washed with 2MHCl and saturated NaHCO$_3$. The organic phase was dried and evaporated to give the title compound as a light brown solid. (48 g; 85%).

$^1$H NMR: (CDCl$_3$) δ: 1.58(9H, s), 7.99(1H, s), 8.05(1H, s), 8.22(1H, s).

t-Butyl 3-bromo-5-cyanobenzoate

A mixture of t-butyl 3-bromo-5-iodobenzoate (1.91 g, 5 mmol), zinc cyanide (585 mg, 5 mmol), and tetrakis(triphenylphosphine)palladium(0) (300 mg, 5 mol %) in dimethylformamide (20 ml) was heated at 80° C. for 2 hours. The solvent was evaporated. The residue was dissolved in ethyl acetate (20 ml) and washed with water and brine. The organic phase was dried and evaporated. Chromatography with ethyl acetate/hexane (1:4) gave the title compound as a colourless oil (1.02 g, 73%).

$^1$H NMR: (CDCl$_3$) δ 1.60(9H, s), 7.92(1H, s), 8.18(1H, s), 8.32(1H, s).

Ethyl 3-bromo-5-nitrobenzoate

Thionyl chloride (15.7 g, 120 mmol) was added to a solution of 3-bromo-5-nitrobenzoic acid in toluene (100 ml). The mixture was refluxed for 6 hours. The solvent was evaporated and the residue dissolved in dry tetrahydrofuran (50 ml), ethanol (10 ml) was added and the mixture stirred at room temperature for 30 mins. The solvent was evaporated and the residue chromatographed in dichloromethane to give the title compound as an off-white solid (13 g, 79%)

$^1$H NMR (CDCl$_3$) δ 1.44(3H, t, J=7 Hz), 4.45(2H, q, J=7 Hz), 8.48(1H, s), 8.54(1H, s), 8.78(1H, s).

Ethyl 3-amino-5-bromobenzoate

A solution of ethyl 3-bromo-5-nitrobenzoate (4.4 g, 16 mmol) and tin(II) chloride (40 g, 170 mmol) in ethanol (125 ml) was heated at 80° C. for 2 hours. The mixture was cooled to room temperature and the solvent evaporated. The residue was suspended in ethyl acetate (250 ml) and washed with 2M NaOH (2×250 ml). The organic phase was washed with water, dried and evaporated to give the title compound as a yellow solid (3.6 g, 92%)

$^1$H NMR: (CDCl$_3$) δ 1.37(3H, t, J=7 Hz), 3.84(2H, br s), 4.34(2H, q, J=7 Hz), 6.98(1H, s), 7.25(1H, s), 7.52(1H, s).

Ethyl 3-bromo-5-[(4-chlorobutanoyl)amino]benzoate

4-Chlorobutyryl chloride (636 mg, 505 μl, 4.5 mmol) was added to a solution of ethyl 3-amino-5-bromobenzoate (1.0 g, 4.1 mmol) and triethylamine (455 mg, 630 ul, 4.5 mmol) in dichloromethane (25 ml) at 0° C. After complete addition the reaction mixture was stirred at room temperature for 30 minutes, then diluted with ethyl acetate (50 ml). The solution was washed with 2M HCl, saturated NaHCO$_3$, water and brine. The organic phase was dried and evaporated to give the title compound as a pale yellow solid (1.35 g, 94%)

$^1$H NMR: (CDCl$_3$) δ 1.26(3H, t, J=7 Hz), 2.20(2H, quintet, J=7 Hz), 2.60(2H, t, J=7 Hz), 3.67(2H, t, J=7 Hz), 4.37(2H, q, J=7 Hz), 7.53(1H, br s), 7.89-7.90(2H, m), 8.20(1H, s).

Ethyl 3-bromo-5-(2-oxo-1-pyrrolidinyl)benzoate

Sodium hydride, 60% suspension in oil (186 mg, 4.65 mmol) was added portionwise over 2 mins to a solution of ethyl 3-bromo-5-[(4-chlorobutanoyl)amino]benzoate (1.35 g, 3.87 mmol) in dry THF (50 ml) under nitrogen. The reaction mixture was stirred at room temperature for 2 hours. The reaction was quenched by the careful addition of water (25 ml). Diethyl ether (50 ml) was added. The organic phase was washed with water, dried and evaporated to give the title compound as a yellow solid (990 mg, 82%).

$^1$H NMR: (CDCl$_3$) δ 1.39(3H, t, J=7 Hz), 2.19(2H, quintet, J=7 Hz), 2.64(2H, t, J=7 Hz), 3.89(2H, t, J=7 Hz), 4.38(2H, q, J=7 Hz), 7.93(1H, s), 7.99(1H, s), 8.29(1H, s).

Methyl 4-(acetylamino)-2'-bromo-2-biphenylcarboxylate

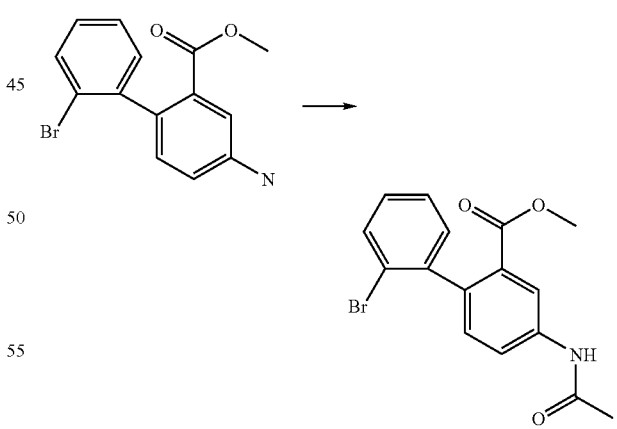

Acetyl chloride (70 mg, 63 μl, 0.89 mmol) was added to a solution of methyl 4-amino-2'-bromo-2-biphenylcarboxylate (227 mg, 0.74 mmol) and triethylamine (90 mg, 123 ul, 0.89 mmol) in diethyl ether (3 ml) and stirred at room temperature for 1 hour. The mixture was diluted with ethyl acetate(10 ml) and washed with 2M HCl, 5% NaHCO$_3$, water and brine the organic phase was dried and evaporated to leave the title compound as a yellow oil (226 mg, 88%).

The following intermediates were prepared using the above method.

| COMPOUND NAME | LCMS or $^1$H NMR |
|---|---|
| Methyl 4-(acetylamino)-2'-bromo-2-biphenylcarboxylate | (CDCl$_3$): 2.20(3H, s), 3.92(3H, s), 7.20-7.99(7H, m). |
| Methyl 2'-bromo-4-(propanoylamino)-2-biphenylcarboxylate | (CDCl$_3$) 1.26(3H, t, J=7Hz), 2.42(2H, m, J=7Hz), 3.90(3H, s), 7.20-8.03(7H, m). |
| Methyl 2'-bromo-4-[(2-methylpropanoyl)amino]-2-biphenylcarboxylate | (CDCl$_3$) 1.26(6H, d, J=7Hz), 2.51-2.57(1H, m), 3.91(3H, s), 7.20-8.06(7H, m). |

Example 44

2"-{[(4-Fluorophenyl)methyl]oxy}-5-[(methyloxy)carbonyl-5"]-(trifluoromethyl)-1,1':2',1"-terphenyl-3-carboxylic acid

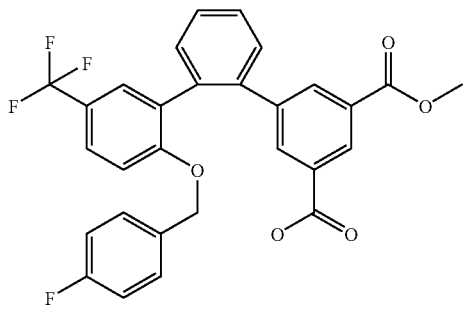

A solution of dimethyl 2"-{[(4-fluorophenyl)methyl]oxy}-5"-(trifluoromethyl)-1,1':2',1"-terphenyl-3,5-dicarboxylate (1.1 g, 2.04 mmol) and potassium hydroxide (35 mg, 0.62 mmol) in methanol (10 ml) and water (2 ml) was refluxed for 3 hours. After cooling to room temperature, water (30 ml) and diethyl ether (10 ml) were added. The aqueous phase was acidified with 2M HCl then extracted with ethyl acetate (2×10 ml). The combined extracts were dried and evaporated to give the title compound as a colourless solid.
LCMS: Rt=4.02 min. [M−H] 523.

Methyl 2"-{[(4-fluorophenyl)methyl]oxy}-5-{[(2-methylpropyl)amino]carbonyl}-5"-(trifluoromethyl)-1,1':2',1"-terphenyl-3-carboxylate

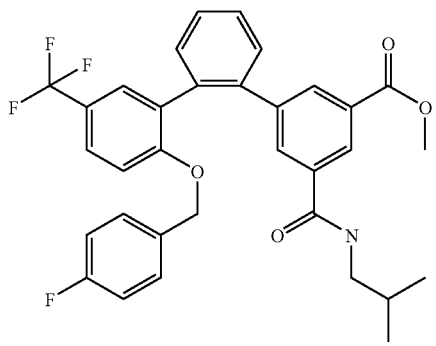

A mixture of 2"-{[(4-fluorophenyl)methyl]oxy}-5-[(methyloxy)carbonyl]-5"-(trifluoromethyl)-1,1':2',1"-terphenyl-3-carboxylic acid (90 mg, 0.17 mmol), 4-methylmorpholine (34 mg, 45 µl, 0.34 mmol), 1-hydroxybenzotriazole hydrate (30 mg, 0.2 mmol), 1-(3-dimethylaminopropyl)-ethylcarbodiimide hydrochloride (38 mg, 0.2 mmol), and isobutylamine (25 mg, 34 ul, 0.34 mmol) in dichloromethane (3 ml) was stirred at room temperature for 2 hours. The mixture was diluted with ethyl acetate (10 ml), then washed with saturated NaHCO3, 2M HCl, water and brine. The organic phase was dried and evaporated. The residue was purified by chromatography in ethyl acetate/hexane (1:9-1:4) to give the title compound as a colourless solid (51 mg, 50%). LCMS: Rt=4.10 min. [M+H] 580

Methyl 4-amino-2'-bromo-2-biphenylcarboxylate

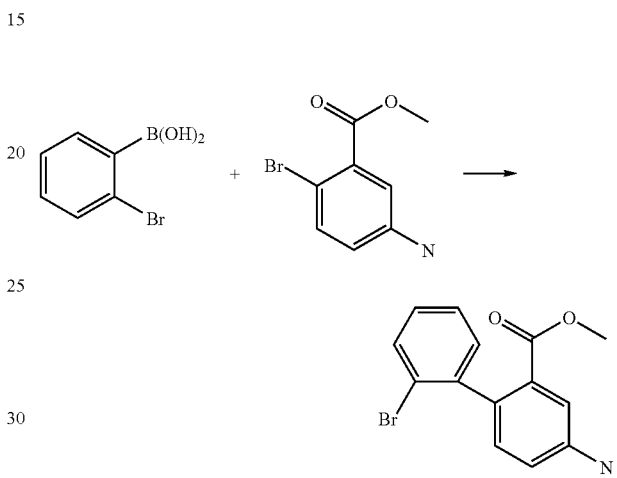

A mixture of 2-bromophenyl boronic acid (600 mg, 3.0 mmol), methyl 5-amino-2-bromobenzoate (1.5 g, 6.5 mmol), potassium carbonate (2.07 g, 15 mmol) and tetrakis(triphenylphosphine)palladium (0) (345 mg, 5 mol %) in 1:1 toluene/ethanol (20 ml) was stirred and heated at 90° C. under nitrogen for 12 hours. After cooling the mixture was diluted with diethyl ether and water and the organic phase dried (MgSO$_4$) and evaporated to dryness. The residue was chromatographed with dichloromethane/iso-hexane (1:2->1:1) to yield the title compound as a pale yellow gum. (682 mg, 74%).

The following intermediates were prepared using the above method.

| COMPOUND NAME | LCMS/$^1$H NMR |
|---|---|
| Methyl 4-amino-2'-bromo-2-biphenylcarboxylate | CDCl$_3$: 3.85(3H, s), 6.80(1H, d), 6.97-7.33(5H, m), 7.57(1H, d). |
| t-Butyl 2'-bromo-5-cyano-3-biphenylcarboxylate | Rt = 3.99 min [M + H$_2$O] 375, 377(1Br) |
| Ethyl 2'-bromo-5-(2-oxo-1-pyrrolidinyl)-3-biphenylcarboxylate | Rt = 3.51 min. [M + H] 388, 390(1Br) |
| Dimethyl 2'-bromo-3,5-biphenyldicarboxylate | Rt = 3.71 min. [M + H] 349, 351(1Br) |

61

Ethyl 5-chloro-2''-[(phenylmethyl)oxy]-1,1':2',1''-terphenyl-2-carboxylate

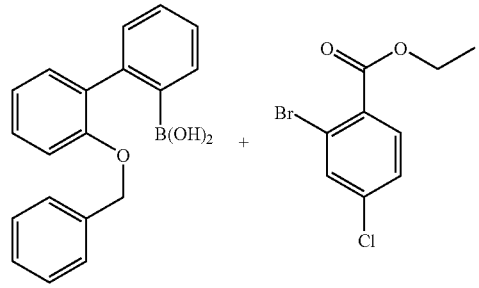

A mixture of 2'-benzyloxybiphenyl boronic acid (50 mg, 0.16 mmol), ethyl 2-bromo-4-chlorobenzoate (66 mg, 0.25 mmol), potassium carbonate (88 mg, 0.64 mmol) and tetrakis(triphenylphosphine)palladium(0) (10 mg, 5 mol %) in 1:1 toluene/ethanol (2 ml) was stirred and heated at 90° C. under nitrogen for 12 hours. After cooling the mixture was diluted with diethyl ether and water and the organic phase dried (MgSO$_4$) and evaporated to dryness. The residue was chromatographed with ethyl acetate/iso-hexane (1:9) to yield the title compound as a pale yellow gum. (46 mg, 66%).

The following intermediates were prepared using the above method.

62

Methyl 4-(acetylamino)-2''-{[(2, 4-difluorophenyl)methyl]oxy}-5''-(trifluoromethyl)-1,1':2',1''-terphenyl-2-carboxylate

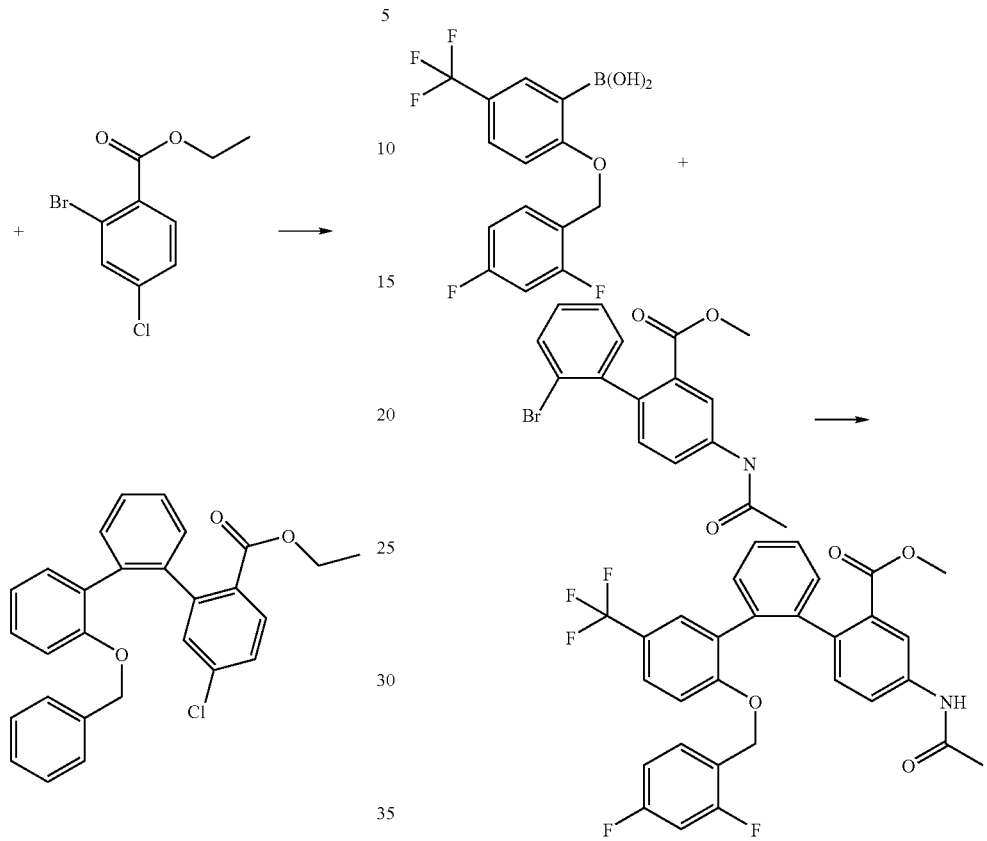

A mixture of 2-[(2,4-difluorobenzyl)oxy]-5-trifluoromethylbenzene boronic acid (66 mg, 0.2 mmol), methyl 4-(acetylamino)-2'-bromo-2-biphenylcarboxylate (110 mg, 0.32 mmol), potassium carbonate (138 mg, 1 mmol) and tetrakis(triphenylphosphine)palladium(0) (23 mg, 5 mol %) in 1:1 toluene/ethanol (4 ml) was stirred and heated at 90° C. under nitrogen for 2 hours. After cooling the mixture was diluted with diethyl ether and water and the organic phase dried (MgSO$_4$) and evaporated to dryness. The residue was chromatographed with ethyl acetate/iso-hexane (2:3) to yield the title compound as a pale yellow gum. (90 mg).

The following intermediates were prepared by the above method.

| COMPOUND NAME | LCMS/$^1$H NMR |
| --- | --- |
| Ethyl 5-chloro-2''-[(phenylmethyl)oxy]-1,1':2',1''-terphenyl-2-carboxylate | (CDCl$_3$) δ: 1.39(3H, t J=9Hz), 4.38(2H, q J=9Hz), 4.84-4.93(2H, br s), 6.75(2H, m), 6.95-7.45(12H, m), 7.50-7.70(1H, m), 7.90-8.03(1H, m) |
| Methyl 4-amino-2''-[(phenylmethyl)oxy]-1,1':2',1''-terphenyl-2-carboxylate | (CDCl$_3$) δ: 3.51(2H, s), 3.63(3H, s), 4.88-4.91(2H, br s), 6.54(br d), 6.75-6.89(3H, m), 6.97-7.08(2H, m), 7.10-7.14(1H, m), 7.23-7.36(9H, m). |
| Ethyl 5-fluoro-2''-[(phenylmethyl)oxy]-1,1':2',1''-terphenyl-3-carboxylate | (CDCl$_3$) δ: 1.25(3H, t), 4.27(2H, q), 4.55-4.90(2H, br s), 6.76(1H, d), 6.90-6.93(2H, m), 7.03-7.05(2H, d), 7.16-7.25(4H, m), 7.41-7.44(4H, m), 7.50-7.52(1H, d), 7.63(1H, s) |

| COMPOUND NAME | LCMS/$^1$H NMR |
|---|---|
| Methyl 4-(acetylamino)-2"-{[(2,4-difluorophenyl)methyl]oxy}-5"-(trifluoromethyl)-1,1':2',1"-terphenyl-2-carboxylate. | (CDCl$_3$) 2.05(3H, s), 3.56(3H, s) 4.88-4.90(2H, br s), 6.76-6.79(2H, m), 6.99-7.01(1H, m), 7.26-7.40(4H, m), 7.46-8.00(6H, m) |
| Methyl 2"-{[(2,4-difluorophenyl)methyl]oxy}-4-(propanoylamino)-5"-(trifluoromethyl)-1,1':2',1"-terphenyl-2-carboxylate. | (CDCl$_3$) 1.21-1.28(3H, m), 2.36-2.41(2H, m), 3.52(3H, s), 4.82-5.03(2H, br s), 6.76-6.79(2H, m), 7.00-7.02(2H, m), 7.26-7.42(6H, m), 7.65-7.99(3H, m). |
| Methyl 2"-{[(2,4-difluorophenyl)methyl]oxy}-4-[(2-methylpropanoyl)amino]-5"-(trifluoromethyl)-1,1':2',1"-terphenyl-2-carboxylate | (CDCl$_3$) 1.23-1.28(6H, m), 2.49-2.56(1H, m), 3.53-3.58(1H, br s), 4.82-5.03(2H, br s), 6.77-6.79(2H, m), 6.95-7.00(1H, m), 7.20-7.55(6H, m), 7.70-8.02(4H, m). |
| t-Butyl 5"-bromo-5-cyano-2"-[(phenylmethyl)oxy]-1,1':2',1"-terphenyl-3-carboxylate | Rt = 4.38 min [M + H$_2$O] 583. |
| t-Butyl 5"-bromo-5-cyano-2"-[(phenylmethyl)oxy]-1,1':2',1"-terphenyl-3-carboxylate | Rt = 4.42 min. [M + H$_2$O] 557, 559(1Br) |
| t-Butyl 5-cyano-2"-[(phenylmethyl)oxy]5"-(trifluoromethyl)-1,1':2',1"-terphenyl-3-carboxylate | Rt = 4.37 min. [M + H2O] 547 |
| Ethyl 2"-{[phenylmethyl]oxy}-5-oxo-1-pyrrolidinyl)-5"-(trifluoromethyl)-1,1':2',1"-terphenyl-3-carboxylate | Rt = 4.06 min. [M + H] 560 |
| Dimethyl 2"-{[(4-fluorophenyl)methyl]oxy}-5"-(trifluoromethyl)-1,1':2',1"-terphenyl-3,5 dicarboxylate | (CDCl$_3$) δ: 3.82(6H, s), 4.45-4.55(1H, b rs), 4.70-4.80(1H, b rs), 6.73(1H, d, J=8Hz), 6.94(3H, m), 7.39-7.56(7H, m), 7.89(1H, s), 8.48(1H, m) |
| Methyl 2"-[(phenylmethyl)oxy]-5-(propanoylamino)-5"-(trifluoromethyl)-1,1':2',1"-terphenyl-3-carboxylate | Rt = 4.04 min [M − H] 532 |
| Ethyl 2"-{[(4-fluorophenyl)methyl]oxy}-5-(propanoylamino)-5"-(trifluoromethyl)-1,1':2',1"-terphenyl-3-carboxylate | Rt = 3.96 min [M − H] 564 |
| Methyl 2"-{[(2,4-difluorophenyl)methyl]oxy}-5-(propanoylamino)-5"-(trifluoromethyl)-1,1':2',1"-terphenyl-3-carboxylate | Rt = 4.00 min [M − H] 568 |

The following compounds were prepared in a similar manner to 2-Benzyloxy-5-chloro-5"-propionylamino[1,1';2',1"]terphenyl-3"-carboxylic acid ethyl ester (Example 6a):

| COMPOUND NAME | LC/MS |
|---|---|
| Ethyl 5"-chloro-5-{[(methyloxy)acetyl]amino}-2"-[(phenylmethyl)oxy]-1,1':2',1"-terphenyl-3-carboxylate | Rt = 3.97 min [M + H] 528, 530 |
| Ethyl 5"-chloro-2"-[(phenylmethyl)oxy]-5-[(2-thienylacetyl)amino]-1,1':2',1"-terphenyl-3-carboxylate | Rt = 4.16 min [M + H] 580, 582 |
| Ethyl 5"-chloro-2"-[(phenylmethyl)oxy]-5-({[(phenylmethyl)oxy]acetyl}amino)-1,1':2',1"-terphenyl-3-carboxylate | Rt = 4.23 min [M + H] 604, 606 |
| Ethyl 4-{[(1-acetyl-5-piperidinyl)carbonyl]amino}-5"-chloro-2"-[(phenylmethyl)oxy]-1,1':2',1"-terphenyl-3-carboxylate | Rt = 3.80 min [M + H] 609, 611 |
| Ethyl 5"-chloro-5-[(phenylcarbonyl)amino]-2"-[(phenylmethyl)oxy]-1,1':2',1"-terphenyl-3-carboxylate | Rt = 4.18 min [M + H] 574, 576 |
| Ethyl 5"-chloro-5-{[(3,5-dimethyl-4-isoxazolyl)carbonyl]amino}-2"-[(phenylmethyl)oxy]-1,1':2',1"-terphenyl-3-carboxylate | Rt = 4.09 min [M + H] 579, 581 |
| Methyl 5"-chloro-5-[(3-methylbutanoyl)amino]-2"-[(phenylmethyl)oxy]1,1':2',1"-terphenyl-3-carboxylate | Rt = 4.17 min [M + H] 540, 542 |
| Methyl 5"-chloro-5-[(N-{[(9H-fluoren-9-ylmethyl)oxy]carbonyl}glycyl)amino]-2"-[(phenylmethyl)oxy]-1,1':2',1"-terphenyl-3-carboxylate | Rt = 4.24 min [M − H] 723 |
| Methyl 2"-[(phenylmethyl)oxy]-4-(propanoylamino)-1,1':2',1"-terphenyl-2-carboxylate | Rt = 3.74 min [M − H] 464 |
| Methyl 4-[(2-methylpropanoyl)amino]-2"-[(phenylmethyl)oxy]-1,1':2',1"-terphenyl-2-carboxylate | Rt = 3.84 min [M − H] 479 |

The following Examples 45-65 were prepared from the appropriate ester intermediate by the standard hydrolysis procedure (General Procedure D):

| EXAMPLE | COMPOUND NAME | LC/MS | H NMR |
|---|---|---|---|
| 45 | 5-Chloro-2"-[(phenylmethyl)oxy]-1,1':2',1"-terphenyl-2-carboxylic acid | Rt=3.92 min [M − H] 413 (1 Cl) | (CDCl₃) 4.89-4.92(2H, br s), 6.71(1H, d, J=9Hz), 6.93-7.68(15H, m). |
| 46 | 4-(Methoxy)-2"-[(phenylmethyl)oxy]-1,1':2',1"-terphenyl-2-carboxylic acid | Rt = 3.69 min [M − H] 409 | (d6-DMSO) 3.72(3H, s), 5.02(2H, br s), 6.72-7.32(15H, m), 12.50(1H, br s). |
| 47 | 2"-{[(2,4-Difluorophenyl)methyl]oxy}-4-(propanoylamino)-5"-(trifluoromethyl)-1,1':2',1"-terphenyl-2-carboxylic acid | Rt = 3.69 min [M − H] 554 | (CDCl₃) 1.24(3H, s, J=7Hz), 2.39(2H, q, J=7Hz), 4.87(2H, br s), 6.74-6.79(3H, m), 7.00-7.02(2H, m), 7.15(1H, br s), 7.26-7.42(5H, m), 7.81(1H, s), 7.82(1H, s). |
| 48 | 2"={[(2,4-Difluorophenyl)methyl]oxy}-4-[(2-methylpropanoyl)amino]-5"-(trifluoromethyl)-1,1':2',1"-terphenyl-2-carboxylic acid | Rt = 3.78 min [M − H]=568 | (CDCl₃) 1.24(6H, d, J=7Hz), 2.50(1H, m, J=7Hz), 4.86(2H, br s), 6.75-6.78(3H, m), 6.95-7.03(2H, m), 7.23-7.42(6H, m), 7.84(1H, m), 7.85(1H, d). |
| 49 | 5-(2-Oxo-1-pyrrolidinyl)-2"-[(phenylmethyl)oxy]-5"-(trifluoromethyl)-1,1':2',1"-terphenyl-3-carboxylic acid | Rt = 3.80 min [M − H] 530 | (CDCl₃) 2.4(2H, m)2.54(2H, t, J=8Hz), 3.30-3.50(2H, br s)4.60-4.92(2H, br s), 6.77(1H, d, J=8Hz), 6.98-7.00(2H, m), 7.22-7.26(4H, m), 7.36-7.66(7H, m), 8.30(1H, s). |
| 50 | 2"-{[(4-Fluorophenyl)methyl]oxy}-5"-(trifluoromethyl)-1,1':2',1"-terphenyl-3,5-dicarboxylic acid | Rt = 3.86 min [M − H] 509 | (d₆-DMSO) 4.65(1H, br s), 4.95(1H, br s), 7.05-7.09(5H, m), 7.41-7.82(7H, m), 8.28-8.45(2H. m). |
| 51 | 2"-{[(4-Fluorophenyl)methyl]oxy}-5-}[(2-methylpropyl)amino]carbonyl}-5"-(trifluoromethyl)-1,1':2',1"-terphenyl-3-carboxylic acid | Rt = 3.97 min [M − H] 564 | (CDCl₃) 0.92(6H, d, J=6Hz), 1.76-1.83(1H, m), 3.19(2H, br s), 4.61(1H, br s), 4.79(1H, br s), 5.78(1H, br s), 6,78(1H, d, J=8Hz), 6.91-6.99(4H, m), 7.40-7.66(7H, m), 7.95(1H, s), 8.33(1H, s). |
| 52 | 6-[2'-{[(4-Fluorophenyl)methyl]oxy}-5'-(trifluoromethyl)-2-biphenylyl]-2-pyrazinecarboxylic acid | Rt = 3.92 min [M + H] 469 | (D₄-MeOD) 4.80(2H, br s), 6.97(2H, t, J=9Hz) 7.06(3H, t, J=8Hz), 7.43(1H, d, J=8Hz), 7.52(1H, s), 7.56-7.58(3H, m), 7.82(1H, d, J=8Hz, 8.21(1H, s), 8.98(1H, s). |
| 53 | 2"-{[(4-Fluorophenyl)methyl]oxy}-5-(propanoylamino)-5"-(trifluoromethyl)-1,1':2',1"-terphenyl-3-carboxylic acid | Rt = 3.80 min [M − H] 536 | (CDCl₃) 1.21(3H, t), 2.33(2H, q), 4.60-4.89(2H, br), 5.30(1H, s), 6.78(1H, d), 6.92-7.04(7H, m), 7.38-7.56(9H, m), 7.96(1H, s). |
| 54 | 2"-[(Phenylmethyl)oxy]-5-(propanoylamino)-5"-(trifluoromethyl)-1,1':2',1"-terphenyl-3-carboxylic acid | Rt = 3.76 min [M − H] 518 | (CDCl₃) 1.21(3H, t), 2.32(2H, q), 4.55-4.98(2H, br), 6.79(1H, d), 6.88(1H, s), 7.04(2H, d), 7.24-7.28(4H, m), 7.41-7.48(5H, m), 7.52(1H, s), 8.03(1H, s). |

-continued

| EXAMPLE | COMPOUND NAME | LC/MS | H NMR |
|---|---|---|---|
| 55 | 2"-{[(2,4-Difluorophenyl)methyl]oxy}-5-(propanoylamino)-5"-(trifluoromethyl)-1,1':2',1"-terphenyl-3-carboxylic acid | Rt = 3.81 min [M − H] 554 | (CDCl$_3$) 1.21(3H, t), 2.34(2H, q), 4.73-5.00(2H, br), 6.75(2H, m), 6.83(1H, d), 6.94-6.99(2H, m), 7.36-7.39(2H, m), 7.44-7.51(4H, m), 7.68(1H, s), 7.90(1H, s). |
| 56 | 5"-Chloro-5-{[(methyloxy)acetyl]amino}-2"-[(phenylmethyl)oxy]-1,1':2',1"-terphenyl-3-carboxylic acid | Rt = 3.69 min [M + H] 500, 502 | (CDCl$_3$) 3.48(3H, s), 3.98(2H, s), 4.59-4.89(2H, br), 6.66(1H, d), 7.03(2H, d), 7.12(1H, d), 7.19(1H, s), 7.23-7.25(5H, m), 7.42-7.45(3H, m), 7.59(1H, d), 8.10(1H, d). |
| 57 | 5"-Chloro-2"-[(phenylmethyl)oxy]-5-[(2-thienylacetyl)amino]-1,1':2',1"-terphenyl-3-carboxylic acid | Rt = 3.95 min [M + H] 552, 554 | (CDCl$_3$) 3.89(2H, s), 4.50-4.87(2H, br), 6.64(1H, d), 7.00(3H, d), 7.06-7.11(3H, m), 7.16(1H, s), 7.23(3H, d), 7.32(2H, s), 7.37-7.44(3H, m), 7.61(1H, s), 8.01(1H, s). |
| 58 | 5"-Chloro-2"-[(phenylmethyl)oxy]-5-({[(phenylmethyl)oxy]acetyl}amino)-1,1':2',1"-terphenyl-3-carboxylic acid | Rt = 4.03 min [M + H] 576, 578 | (CDCl$_3$) 4.06(2H, s), 4.64(2H, s), 4.64-4.85(2H, br), 6.65(1H, d), 7.02(2H, d), 7.11(1H, d), 7.17-7.23(4H, m), 7.35-7.44(9H, m), 7.56(1H, s), 7.61(1H, s), 8.05(1H, s), 8.16(1H, s). |
| 59 | 5-{[(1-Acetyl-4-piperidinyl)carbonyl]amino}-5"-chloro-2"-[(phenylmethyl)oxy]-1,1':2',1"-terphenyl-3-carboxylic acid | Rt = 3.51 min [M + H] 581, 583 | (d$_6$-DMSO) 1.45-1.61(2H, m), 1.78(2H, d), 2.02(3H, s), 4.02(2H, broad singlet), 4.84(2H, s), 6.90(1H, d), 7.00(1H, s), 7.12(2H, d), 7.17(1H, d), 7.20(3H, d), 7.30(1H, d), 7.35-7.42(3H, m), 7.70(1H, s), 7.92(1H, s), 9.37(1H, s). |
| 60 | 5"-Chloro-5-[(phenylacetyl)amino]-2"-[(phenylmethyl)oxy]-1,1':2',1"-terphenyl-3-carboxylic acid | Rt = 3.98 min [M + H] 546, 548 | (CDCl$_3$) 3.68(2H, s), 4.45-4.86(2H, br), 6.62(1H, d), 6.85(1H, s), 7.01(2H, s), 7.10(1H, d), 7.14(1H, s), 7.21(3H, s), 7.28-7.43(10H, m), 7.58(1H, s), 7.96(1H, s). |
| 61 | 5"-Chloro-5-{[(3,5-dimethyl-4-isoxazolyl)carbonyl]amino}-2"-[(phenylmethyl)oxy]-1,1':2',1"-terphenyl-3-carboxylic acid | Rt = 3.84 min [M + H] 551, 553 | (CDCl$_3$) 2.43(3H, s), 2.62(3H, s), 4.56-4.90(2H, br), 6.67(1H, d), 6.98(1H, s), 7.01(2H, d), 7.14(1H, d), 7.21-7.24(3H, m), 7.36-7.10(2H, m), 7.46-7.48(3H, m), 7.70(1H, s), 8.23(1H, s). |
| 62 | 5"-Chloro-5-[(3-methylbutanoyl)amino]-2"-[(phenylmethyl)oxy]-1,1':2',1"-terphenyl-3-carboxylic acid | Rt = 3.95 min [M + H] 512, 514 | (CDCl$_3$) 0.98-1.02(6H, m), 1.07-1.34(1H, m), 2.18(2H, s), 4.56-4.90(2H, br), 6.65(1H, d), 6.89(1H, s), 7.03(2H, d), 7.11(1H, d), 7.19(1H, s), 7.22-7.25(2H, m), 7.38-7.46(5H, m), 7.60(1H, s), 8.07(1H, s). |

| EXAMPLE | COMPOUND NAME | LC/MS | H NMR |
|---|---|---|---|
| 63 | 5"-Chloro-5-(glycylamino)-2"-[(phenylmethyl)oxy]-1,1':2',1"-terphenyl-3-carboxylic acid | Rt = 2.91 min [M + H] 485, 487 | ($d_6$DMSO) 4.65-4.95(2H, br), 6.92(1H, d), 7.06-7.09(3H, m), 7.23-7.27(2H, m), 7.34-7.47(5H, m), 7.67(1H, s), 8.10(1H, s). |
| 64 | 2"-[(Phenylmethyl)oxy]-4-(propanoylamino)-1,1':2',1"-terphenyl-2-carboxylic acid | Rt = 3.54 min [M − H] 450 | ($d_6$-DMSO) 1.07(3H, t), 2.30(2H, q), 4.20-5.07(2H, br), 6.70(1H, t), 6.79(1H, d), 6.95(2H, t), 7.06-7.15(2H, m), 7.22-7.32(8H, m), 7.46(1H, d), 7.91(1H, s), 9.91(1H, s), 12.37-12.60(1H, br). |
| 65 | 4-[(2-Methylpropanoyl)amino]-2"-[(phenylmethyl)oxy]-1,1':2',1"-terphenyl-2-carboxylic acid | Rt = 3.64 min [M − H] 464 | ($d_6$-DMSO) 1.08(6H, d), 5.02(2H, s), 6.72(1H, t), 6.79(1H, d), 6.96(2H, t), 7.08-7.15(2H, m), 7.25-7.33(8H, m), 7.47(1H, d), 7.94(1H, s), 9.90(1H, s), 12.34-12.60(1H, br). |

Examples 66-68 were prepared by cleavage of their t-butyl esters using 25% trifluoroacetic acid in dichloromethane.

| EXAMPLE | COMPOUND NAME | LC/MS | $^1$H NMR |
|---|---|---|---|
| 66 | 5-Cyano-2"-{[(2,4-difluorophenyl)methyl]oxy}-5"-(trifluoromethyl)-1,1':2',1"-terphenyl-3-carboxylic acid | Rt = 3.99 min [M − H] 508 | (CDCl$_3$) 5.16(2H, s), 6.90-7.43(9H, m), 7.72(1H, d, J=9Hz), 7.95(1H, s), 8.37(1H, s), 8.40(1H, s). |
| 67 | 5"-Bromo-5-cyano-2"-[(phenylmethyl)oxy]-1,1':2',1"-terphenyl-3-carboxylic acid | Rt = 4.03 min [M − H] 482, 484(1Br) | (CDCl$_3$) 4.60(1H, br s), 4.80(1H, br s), 6.64(1H, d, J=9Hz), 6.99-7.01(2H, m), 7.27-7.52(10H, m), 8.03(1H, s), 8.17(1H, s). |
| 68 | 5-Cyano-2"-[(phenylmethyl)oxy]-5"-(trifluoromethyl)-1,1':2',1"-terphenyl-3-carboxylic acid | Rt = 3.99 [M − H] 472 | |

General Reaction F

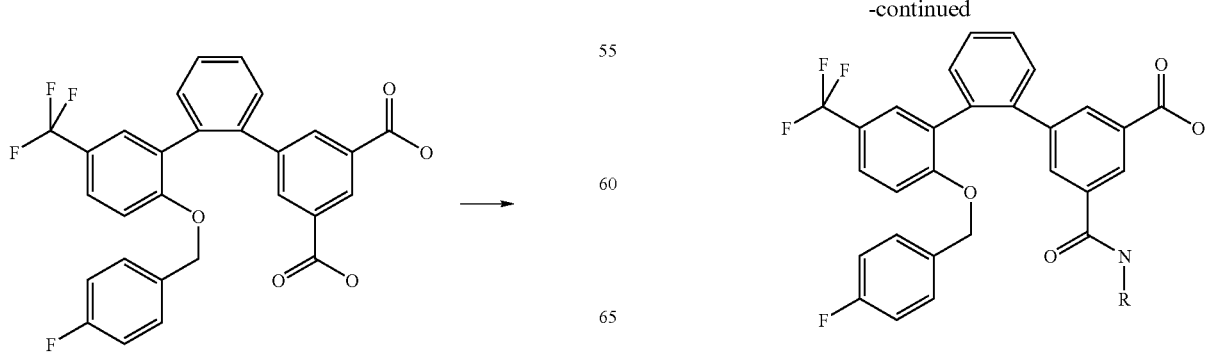

A mixture of 2"-[(4-fluorophenyl)methyl]oxy)5"-(trifluoromethyl)-1,1':2',1"-terphenyl-3,5-dicarboxylic acid (50 mg, 0.1 mmol), 4-methylmorpholine (20 mg, 22 μl, 0.2 mmol), 1-hydroxybenzotriazole hydrate (18 mg, 0.12 mmol), 1-(3-dimethylaminopropyl)-ethylcarbodiimide hydrochloride (23 mg, 0.12 mmol), and the amine (0.1 mmol) in dichloromethane (3 ml) was stirred at room temperature for 2 hours. The mixture was diluted with ethyl acetate (10 ml), then washed with saturated NaHCO$_3$, 2M HCl, water and brine. The organic phase was dried and evaporated. The residue was purified by mass directed preparative LCMS to give the following Examples 69-71:

stirring for 15 minutes triisopropyl borate (9.61 g, 51.12 mmol) was added over 2 minutes and the mixture allowed to warm to room temperature. 2M hydrochloric acid (150 ml) was added with vigorous stirring for 25 minutes and the organic phase was separated, dried (magnesium sulphate) and evaporated. The residue was purified by chromatography on silica eluting with ethyl acetate/iso-hexane (1:4) then triturated with iso-hexane to give 5.15 g of white solid.

$^1$H NMR (CDCl$_3$) δ: 1.94-1.98 (2H, m), 2.64-2.74 (4H, m), 4.37 (2H, s), 5.07 (2H, s), 6.90 (1H, d, J=9 Hz), 7.15-7.38 (7H, m).

| EXAMPLE | COMPOUND NAME | LC/MS | $^1$H NMR |
|---|---|---|---|
| 69 | 5-(Aminocarbonyl)-2"-{[(4-fluorophenyl)methyl]oxy}-5"-(trifluoromethyl)-1,1':2',1"-terphenyl-3-carboxylic acid | Rt = 3.60 min [M − H] 508 | (CDCl$_3$) 4.65(1H, br s), 4.82(1H, br s), 5.80(1H, br s), 6.05(1H, br s), 6.78(1H, d, J=9Hz), 6.99-7.02(4H, m), 7.41-7.51(6H, m), 7.71(1H, s), 7.97(1H, s), 8.34(1H, s). |
| 70 | 2"-{[(4-Fluorophenyl)methyl]oxy}-5-{[(2-hydroxyethyl)amino]carbonyl}-5"-(trifluoromethyl)-1,1':2',1"-terphenyl-3-carboxylic acid | Rt = 3.52 min [M − H] 552 | (CDCl$_3$) 3.60(2H, br s), 3.86(2H, t, J=4Hz), 4.65(1H, br s), 4.80(1H, br s), 6.71(1H, d, J=8Hz), 6.89-6.94(3H, m), 7.37-7.49(5H, m), 7.83(1H, s), 7.86(1H, s), 8.45(1H, s). |
| 71 | 2"-{[(4-Fluorophenyl)methyl]oxy}-5-{[(3-pyridinylmethyl)amino]carbonyl}-5"-(trifluoromethyl)-1,1':2',1"-terphenyl-3-carboxylic acid | Rt = 3.54 min [M + H] 601 [M − H] 599 | (CDCl$_3$) 4.57(1H, br s), 4.69(1H, br s), 6.66-6.94(6H, m), 7.26-7.48(6H, m), 7.72-7.74(2H, m), 7.90(1H, s), 8.38(1H, s), 8.40-8.50(1H, br s), 8.65-8.75(1H, br s). | preparation of Intermediates

2'-Bromo-5-chloro-2-[(phenylmethyl)oxy]biphenyl

A mixture of 2-bromophenylboronic acid (2.01 g, 10 mmol), 4-chloro-2-iodo-1-[(phenylmethyl)oxy]benzene (3.445 g, 10 mmol), potassium carbonate (5.52 g, 40 mmol) and tetrakis(triphenylphosphine)palladium(0) (580 mg, 0.5 mmol) in 1:1 toluene/ethanol (45 ml) was stirred and heated at 90° C. under nitrogen for 2 hours when a further 1 g (4.98 mmol) of 2-bromophenylboronic acid and 0.2 g (0.17 mmol) of tetrakis(triphenylphosphine)palladium(0) were added. The mixture was heated for 6 hours then cooled, diluted with diethyl ether/water and the organic phase separated, dried (magnesium sulphate) and evaporated. The residue was purified by chromatography on silica eluting with ethyl acetate/iso-hexane (1:49) then rechromatographed eluting with dichloromethane/iso-hexane (1:9) to give 2.06 g of colourless gum which slowly crystallised.

$^1$H NMR (CDCl$_3$) δ: 5.04 (2H, s), 6.92 (1H, d, J=9 Hz), 7.18-7.35 (5H, m), 7.66 (1H, dd, J=8 Hz, 1 Hz).

{5'-Chloro-2'-[(phenylmethyl)oxy]-2-biphenylyl}boronic acid 1.6M butyllithium in hexanes (16.8 ml, 26.88 mmol) was added over 10 minutes to a stirred solution of 2'-bromo-5-chloro-2-[(phenylmethyl)oxy]biphenyl (9.29 g, 25.56 mmol) in tetrahydrofuran (120 ml) at −78° C. under nitrogen. After Ethyl 6-{5'-chloro-2'-[(phenylmethyl)oxy]-2-biphenylyl}2-pyridinecarboxylate

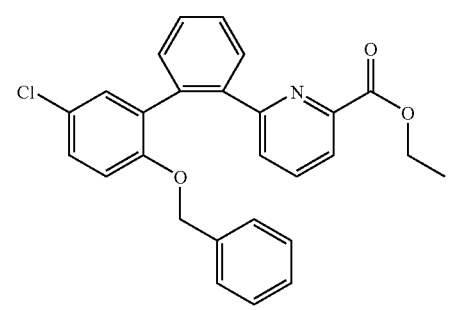

A mixture of {5'-chloro-2'-[(phenylmethyl)oxy]-2-biphenylyl}boronic acid (1.32 g, 3.9 mmol), ethyl 6-bromopicolinate (851 mg, 3.7 mmol), potassium carbonate (2.76 g, 20 mmol) and tetrakis(triphenylphosphine)palladium(0) (232 mg, 0.2 mmol) in 1:1 toluene/ethanol (25 ml) was stirred and heated at 90° C. under nitrogen for 1.5 hours. After cooling and dilution with diethyl ether/water the organic phase was separated, dried (magnesium sulphate) and evaporated. The residue was chromatographed on silica eluting with ethyl acetate/iso-hexane (3:17) to give 1.37 g of white solid. LC/MS t=3.76, [MH+] 444.3

Ethyl 6-(5'-chloro-2'-hydroxy-2-biphenylyl)-2-pyridinecarboxylate

Ethyl 6-{5'-chloro-2'-[(phenylmethyl)oxy]-2-biphenylyl}-2-pyridinecarboxylate (1.22 g, 2.75 mmol) was dissolved in acetic acid (5 ml) and 48% hydrogen bromide in acetic acid (5 ml), left at room temperature for 0.5 hours then diluted with diethyl ether/water and basified with potassium carbonate. The organic phase was separated, dried (magnesium sulphate), evaporated and chromatographed on silica eluting with ethyl acetate/iso-hexane (1:3). The product was dissolved in ethanol (20 ml), 60% sodium hydride (2 mg) added and the solution left at room temperature for 16 hours. The resulting solution was acidified with acetic acid, diluted with water/ether and the organic phase washed with saturated sodium bicarbonate solution, dried (magnesium sulphate), evaporated and chromatographed on silica to give 801 mg of colourless gum. LC/MS t=3.33, [MH+] 354.3, 356.3

Ethyl 6-(5'-chloro-2'-{[(4-fluorophenyl)methyl]oxy}-2-biphenylyl)-2-pyridinecarboxylate

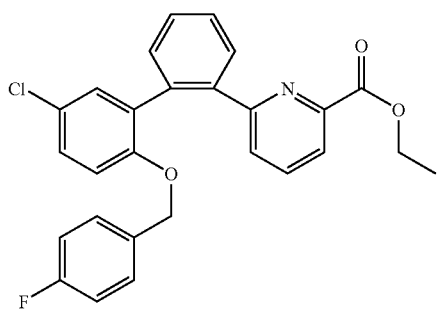

A mixture of ethyl 6-(5'-chloro-2'-hydroxy-2-biphenylyl)-2-pyridinecarboxylate (177 mg, 0.5 mmol), potassium carbonate (138 mg, 1 mmol) and 4-fluorobenzyl bromide (104 mg, 0.55 mmol) in acetone (4 ml) was stirred and refluxed for 2 hours then cooled, filtered, evaporated and chromatographed on silica eluting with ethyl acetate/iso-hexane (1:9) to give 190 mg of white solid. LC/MS t=3.79, [MH+] 462.3

Ethyl 6-(5'-chloro-2'-{[(2,4-difluorophenyl)methyl]oxy}-2-biphenylyl)-2-pyridinecarboxylate

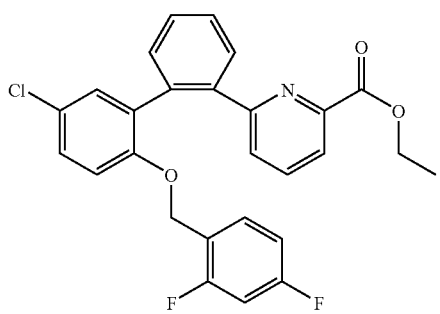

Prepared in a similar manner to ethyl 6-(5'-chloro-2'-{[(4-fluorophenyl)methyl]oxy}-2-biphenylyl)-2-pyridinecarboxylate but using 2,4-difluorobenzyl bromide in place of 4-fluorobenzyl bromide. LC/MS t=3.82, [MH+] 480.3

2'-Bromo-2-{[(4-fluorophenyl)methyl]oxy}-5-(trifluoromethyl)biphenyl

Prepared as for 2'-bromo-5-chloro-2-[(phenylmethyl)oxy]biphenyl but using 1-{[(4-fluorophenyl)methyl]oxy}-2-iodo-4-(trifluoromethyl)benzene instead of 4-chloro-2-iodo-1-[(phenylmethyl)oxy]benzene.
$^1$H NMR (CDCl$_3$) δ: 5.08 (2H, s), 6.99 (2H, t), 7.04 (1H, d), 7.12-7.36 (5H, m), 7.46 (1H, d), 7.60 (1H, dd), 7.66 (1H, d).

[2'-{[(4-Fluorophenyl)methyl]oxy}-5'-(trifluoromethyl)-2-biphenylyl]boronic acid Prepared as for {5'-chloro-2'-[(phenylmethyl)oxy]-2-biphenylyl}boronic acid but using 2'-bromo-2-{[(4-fluorophenyl)methyl]oxy}-5-(trifluoromethyl)biphenyl instead of 2'-bromo-5-chloro-2-[(phenylmethyl)oxy]biphenyl. LC/MS t=3.63, [MH−] 389.0

Ethyl 2-[2'{[(4-fluorophenyl)methyl]oxy}-5'-(trifluoromethyl)-2-biphenylyl]-4-pyridinecarboxylate

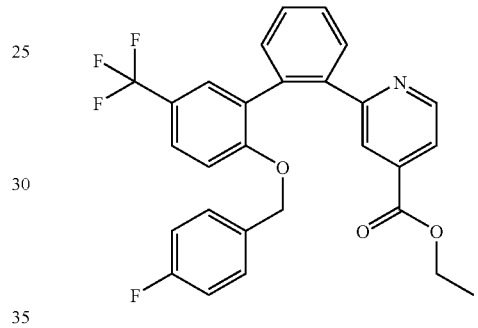

A mixture of [2'{[(fluorophenyl)methyl]oxy}-5'-(trifluoromethyl)-2-biphenylyl]boronic acid (98 mg, 0.25 mmol), ethyl 2-bromo-4-pyridinecarboxylate (58 mg, 0.25 mmol), potassium carbonate (276 mg, 2 mmol) and tetrakis(triphenylphosphine)palladium(0) (29 mg, 0.025 mmol) in 1:1 toluene/ethanol (4 ml) was stirred and heated at 90° C. under nitrogen for 2 hours. After cooling and dilution with diethyl ether/water the organic phase was separated, dried (magnesium sulphate) and evaporated. The residue was chromatographed on silica eluting with ethyl acetate/iso-hexane (1:9) to give 81 mg of colourless gum. LC/MS t=4.10, [MH+] 496.1

Ethyl 3-amino-6-[2'-{[(4-fluorophenyl)methyl]oxy}-5'-(trifluoromethyl)-2-biphenylyl]-2-pyrazinecarboxylate

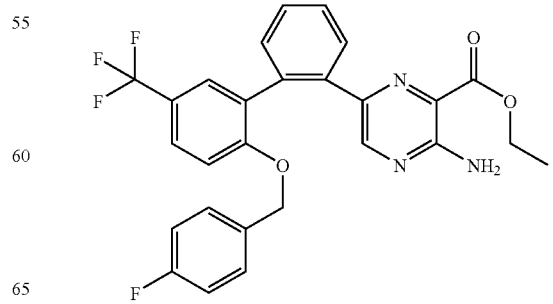

Prepared as a white solid in a similar manner to ethyl 2-[2'-{[(4-fluorophenyl)methyl]oxy}-5'-(trifluoromethyl)-2-biphenylyl]-4-pyridinecarboxylate but using methyl 3-amino-6-bromo-2-pyrazinecarboxylate in place of ethyl 2-bromo-4-pyridinecarboxylate.
LC/MS t=3.96, [MH+] 512.1

Ethyl 5-(acetylamino)-2-bromobenzoate

A mixture of 5-(acetylamino)-2-bromobenzoic acid (2.58 g, 10 mmol), 1-hydroxybenzotriazole (1.68 g, 11 mmol), dimethylaminopyridine (1.22 g, 10 mmol) and 1-(3-dimethylaminopropyl)-ethylcarbodiimide hydrochloride (2.20 g, 11.5 mmol) in dichloromethane/ethanol (5:1, 30 ml) was stirred at room temperature for 2 hours then washed with saturated sodium bicarbonate solution, dried (magnesium sulphate) and chromatographed on silica eluting with ethyl acetate/iso-hexane (2:3) to give 2.18 g of white solid.
$^1$H NMR (CDCl$_3$) δ: 1.40 (3H, t), 2.19 (3H, s), 4.39 (2H, q), 7.27 (1H, br s), 7.58 (1H, d), 7.64 (1H, dd), 7.84 (1H, d).

Ethyl 4-(acetylamino)-2'-bromo-2-biphenylcarboxylate

A mixture of 2-bromophenylboronic acid (1.61 g, 8.0 mmol), ethyl 5-(acetylamino)-2-bromobenzoate (2.15 g, 7.5 mmol), potassium carbonate (5.52 g, 40 mmol) and tetrakis(triphenylphosphine)palladium(0) (869 mg, 0.75 mmol) in 1:1 toluene/ethanol (40 ml) was stirred and heated at 90° C. under nitrogen for 2 hours. After cooling the mixture was diluted with diethyl ether and water and the organic phase dried (MgSO$_4$) and evaporated to dryness. The residue was chromatographed with ethyl acetate/iso-hexane (2:3) to yield 1.33 g of the title compound as a white foam.
LC/MS t=3.26, [MH+] 364.0

Ethyl 4-(acetylamino)-2''-[(phenylmethyl)oxy]-5''-(trifluoromethyl)-1,1':2',1''-terphenyl-2-carboxylate

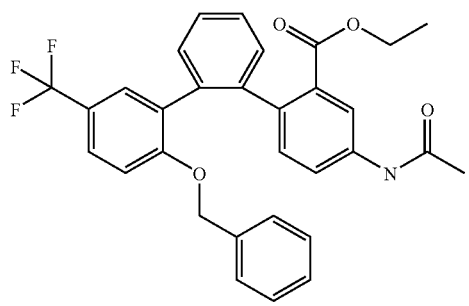

A mixture of [2-[(phenylmethyl)oxy]-5-(trifluoromethyl)phenyl]boronic acid (118 mg, 0.4 mmol), ethyl 4-(acetylamino)-2'-bromo-2-biphenylcarboxylate (121 mg, 0.33 mmol), potassium carbonate (414 mg, 3 mmol) and tetrakis(triphenylphosphine)palladium(0) (39 mg, 0.033 mmol) in 1:1 toluene/ethanol (5 ml) was stirred and heated at 90° C. under nitrogen for 2 hours. After cooling the mixture was diluted with diethyl ether and water and the organic phase dried (MgSO$_4$) and evaporated to dryness. The residue was chromatographed with ethyl acetate/iso-hexane (1:2) to yield 121 mg of the title compound as a colourless gum.
LC/MS t=3.88, [MH−] 532.2

The following intermediates were prepared by a similar route to ethyl 4-(acetylamino)-2''-[(phenylmethyl)oxy]-5''-(trifluoromethyl)-1,1':2',1''-terphenyl-2-carboxylate from the appropriate intermediates.

| COMPOUND NAME | LCMS |
|---|---|
| Ethyl 4-(acetylamino)-2''-{[(4-fluorophenyl)methyl] oxy}-5''-(trifluoromethyl)-1,1':2',1''-terphenyl-2-carboxylate | Rt = 3.89, [MH−] 550.1 |
| Ethyl 4-(acetylamino)-2''-{[(2,4-difluorophenyl)methyl] oxy}-5''-(trifluoromethyl)-1,1':2',1''-terphenyl-2-carboxylate | Rt = 3.90, [MH−] 568.1 |

Ethyl 2'-bromo-4-methyl-2-biphenylcarboxylate

Prepared in a similar way to ethyl 4-(acetylamino)-2'-bromo-2-biphenylcarboxylate but using ethyl 2-bromo-5-methylbenzoate instead of ethyl 5-(acetylamino)-2-bromobenzoate.
LC/MS t=3.77, [MH+] 319.0

Ethyl 4-methyl-2''-[(phenylmethyl)oxy]-1,1':2',1''-terphenyl-2-carboxylate

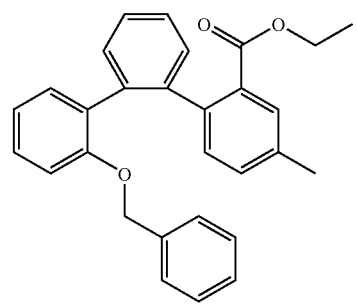

Prepared in a similar way to ethyl 4-(acetylamino)-2''-[(phenylmethyl)oxy]-5''-(trifluoromethyl)-1,1':2',1''-terphenyl-2-carboxylate but using {2'-[(phenylmethyl)oxy]-2-biphenylyl}boronic acid instead of [2-[(phenylmethyl)oxy]-5-(trifluoromethyl)phenyl]boronic acid and ethyl 2'-bromo-4-methyl-2-biphenylcarboxylate instead of ethyl 4-(acetylamino)-2'-bromo-2-biphenylcarboxylate. LC/MS t=4.11, [MH+] 423.1

Ethyl 2''-{[(2,4-difuorophenyl)methyl]oxy}-4-methyl-5''-(trifluofomethyl)-1,1':2',1''-terphenyl-2-carboxylate

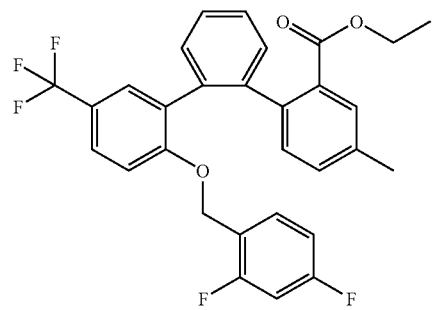

Prepared in a similar way to ethyl 4-(acetylamino)-2''-[(phenylmethyl)oxy]-5''-(trifluoromethyl)-1,1':2',1''-terphenyl-2-carboxylate but using [2'-{[(2,4-difluorophenyl)methyl]oxy}5'-(trifluoromethyl)-2-biphenylyl]boronic acid instead of [2-[(phenylmethyl)oxy]-5-(trifluoromethyl)phenyl]boronic acid and ethyl 2'-bromo-4-methyl-2-biphenylcarboxylate instead of ethyl 4-(acetylamino)-2'-bromo-2-biphenylcarboxylate.

$^1$H NMR (CDCl$_3$) δ: 0.89 (3H, t), 2.31 (3H, t), 3.95 (2H, q), 4.91 (2H, q), 6.77-7.55 (9H, m).

The following Examples 72-81 were prepared by the standard hydrolysis procedure (General Procedure D):

| EXAMPLE | COMPOUND NAME | LC/MS | $^1$H NMR |
|---|---|---|---|
| 72 | 6-{5'-Chloro-2'-[(phenylmethyl)oxy]-2-biphenylyl}-2-pyridinecarboxylic acid | Rt = 3.61 [MH+] 416.3 | (CDCl$_3$) 4.40-4.83(2H, br d), 6.69(1H, d, J=8Hz), 6.92-6.94(2H, m), 7.20-7.29(5H, m), 7.37-7.45(2H, m), 7.51-7.56(2H, m), 7.64-7.73(2H, m), 7.99(1H, d, J=8Hz) |
| 73 | 6-(5'-Chloro-2'-{[(4-fluorophenyl)methyl]oxy}-2-biphenylyl)-2-pyridinecarboxylic acid | Rt = 3.62 [MH+] 434.3 436.3 | (CDCl$_3$) 4.35-4.78(2H, br d), 6.69(1H, d, J=8Hz), 6.90-6.93(4H, m), 7.21-7.28(3H, m), 7.37-7.41(2H, m), 7.53-7.56(2H, m), 7.62-7.64(1H, m), 7.72(1H, t), 7.99(1H, d, J=8Hz) |
| 74 | 6-(5'-Chloro-2'-{[(2,4-difluorophenyl)methyl]oxy}-2-biphenylyl)-2-pyridinecarboxylic acid | Rt = 3.64 [MH+] 452.2 454.2 | (CDCl$_3$) 4.43-4.78(2H, br d), 6.67-6.76(3H, m), 6.89(1H, q), 7.23-7.28(3H, m), 7.37-7.40(2H, m), 7.53-7.55(2H, m), 7.63-7.66(1H, m), 7.74(1H, t, J=8Hz), 8.00(1H, d, J=8Hz) |
| 75 | 2-[2'-{[(4-Fluorophenyl)methyl]oxy}-5'-(trifluoromethyl)-2-biphenylyl]-4-pyridinecarboxylic acid | Rt = 3.86 [MH+] 468.1 | (DMSO-d$_6$) 4.65-5.10(2H, br s), 7.09-7.11(5H, m), 7.39-7.71(8H, m), 8.61(1H, d, J=5Hz), 13.4(1H, br s) |
| 76 | 3-Amino-6-[2'-{[(4-fluorophenyl)methyl]oxy}-5'-(trifluoromethy)-2-biphenylyl]-2-pyrazinecarboxylic acid | Rt = 3.83 [MH+] 484.1 | (DMSO-d$_6$) 4.65-5.10(2H, br s), 7.05-7.15(5H, m), 7.34-7.39(3H, m), 7.46-7.54(3H, m), 7.64(1H, d, J=9Hz), 7.73(1H, d, J=9Hz), 7.78(1H, s), 12.8(1H, br s) |
| 77 | 4-(Acetylamino)-2''-[phenylmethyl)oxy]-5''-(trifluoromethyl)-1,1':2',1''-terphenyl-2-carboxylic acid | Rt = 3.56 [MH−] 504.0 | (CDCl$_3$) 2.18(3H, s), 4.78-4.95(2H, m), 6.75(1H, d, J=9Hz), 7.01-7.49(14H, m), 7.80(1H, dd, J=8Hz, 2Hz) |
| 78 | 4-(Acetylamino)-2''-{[(4-fluorophenyl)methyl]oxy}-5''-(trifluoromethyl)-1,1':2',1''-terphenyl-2-carboxylic acid | Rt = 3.58 [MH−] 522.0 | (CDCl$_3$) 2.18(3H, s), 4.78-4.95(2H, m), 6.74(1H, d, J=9Hz), 6.90-7.09(5H, m), 7.15(1H, br s), 7.27-7.50(7H, m), 7.80(1H, d, J=8Hz) |
| 79 | 4-(Acetylamino)-2''-{[(2,4-difluorophenyl)methyl]oxy}-5''-(trifluoromethyl)-1,1':2',1''-terphenyl-2-carboxylic acid | Rt = 3.60 [MH−] 540.0 | (DMSO-d$_6$) 2.02(3H, s), 5.12(2H, br d), 6.74(1H, br d,), 7.05-7.38(9H, m), 7.50(2H, dd), 7.89(1H, d, J=2Hz), 10.0(1H, s), 12.6(1H, br s) |
| 80 | 4-Methyl-2''-[(phenylmethyl)oxy]-1,1':2',1''-terphenyl-2-carboxylic acid | Rt = 3.80 [MH−] 393.0 | (DMSO-d$_6$) 2.26(3H, s), 5.02(2H, br s), 6.70(1H, t), 6.79(1H, d), 6.95-7.13(5H, m), 7.25-7.34(8H, m), 7.47(1H, s), 12.5(1H, br s) |
| 81 | 2''-{[(2,4-Difluorophenyl)methyl]oxy}-4-methyl-5''-(trifluoromethyl)-1,1':2',1''-terphenyl-2-carboxylic acid | Rt = 3.97 [MH−] 497.1 | (DMSO-d$_6$) 2.26(3H, s), 5.11(2H, br q), 6.72(1H, d), 6.79(1H, d), 7.05-7.16(3H, m), 7.23(1H, d, J=9Hz), 7.26-7.44(5H, m), 7.49-7.51(2H, m), 12.6(1H, br s) | preparation of Intermediates

2-Methoxy-5-fluoro[1,1',2,2']terphenyl-3"-carboxylic acid ethyl ester

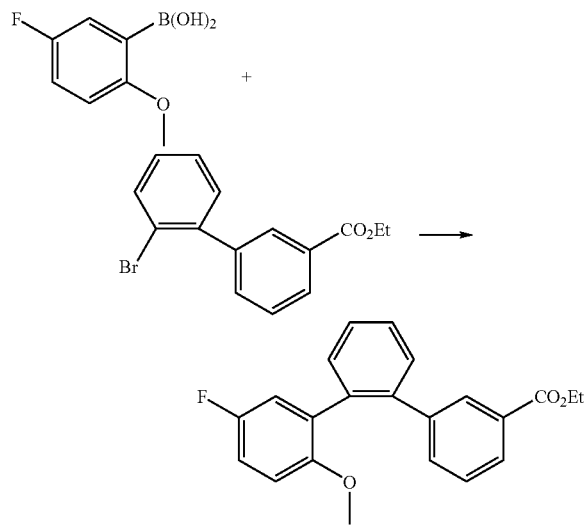

2'-Bromobiphenyl-3-carboxylic acid ethyl ester (1.53 g, 5 mmol), 2-methoxy-5-fluorophenylboronic acid (935 mg, 5.5 mmol), tetrakis(triphenylphosphine)palladium(0) (580 mg, 0.5 mmol) and potassium carbonate (5.52 g, 40 mmol) were heated in toluene-ethanol(1:1, 50 ml) at 90° C. for 3 hours. Upon cooling, the mixture was diluted with diethyl ether and water, the combined organic layers were dried (MgSO$_4$), filtered and concentrated. The residue was purified by chromatography using Biotage® with 10% ethyl acetate in isohexane as eluent to yield the title compound (930 mg).

$^1$H NMR (CDCl$_3$) δ 1.34(3H, t), 3.30(3H, s), 4.31(2H, q), 6.59(1H, dd), 6.89-6.92(2H, m), 7.23-7.27(2H, m), 7.37-7.45 (4H, m), 7.87(1H, dd), 7.89(1H, s).

2-Hydroxy-5-fluoro[1,1',2,2']terphenyl-3"-carboxylic acid

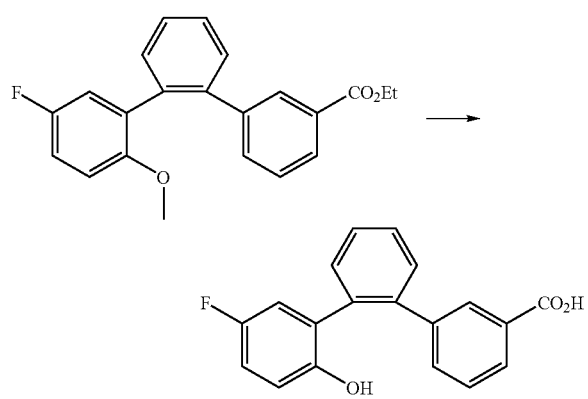

2-Methoxy-5-fluoro[1,1',2,2']terphenyl-3"-carboxylic acid ethyl ester (930 mg, 2.66 mmol) was dissolved in dichloromethane (20 ml), cooled to 0° C. and 1M BBr$_3$ in dichloromethane (5.32 ml, 5.32 mmol) added dropwise at 0° C. The mixture was allowed to reach room temperature and stirred for 17 hours. The reaction was poured onto ice and extracted with diethyl ether which was washed with water, dried (MgSO$_4$) and evaporated. The residue was partitioned between isohexane and 2M sodium hydroxide solution and filtered. The aqueous layer was acidified with 2M hydrochloric acid solution and the product extracted into diethyl ether (×2), which was washed with water, dried (MgSO$_4$) and evaporated to a cream foam (409 mg)

LC/MS Rt=3.40 min [M−H] 307

2-Benzyloxy 5-fluoro[1,1',2,2']terphenyl-3"-carboxylic acid benzyl ester

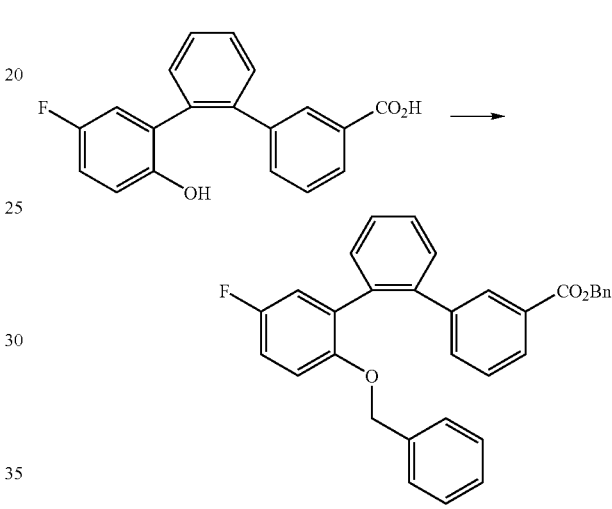

2-Hydroxy-5-fluoro[1,1',2,2']terphenyl-3"-carboxylic acid (136 mg, 0.442 mmol) was stirred in acetone (5 ml) and potassium carbonate (183 mg, 1.327 mmol) added, followed by benzyl bromide (166 mg, 116 μl, 0.973 mmol). The mixture was stirred at reflux for 16 hours. After cooling, diethyl ether and water were added and the organic phase washed with brine, dried (MgSO$_4$) and evaporated to a clear oil (200 mg).

$^1$H NMR (CDCl$_3$) δ 4.63(2H, br s), 5.27(2H, s), 6.61(1H, dd), 6.90-7.44(18H, m), 7.86(1H, s), 7.89(1H, dd).

The following intermediates were prepared from the appropriate intermediates using a similar route to that used for the preparation of 2-Benzyloxy-5-fluoro[1,1',2,2']terphenyl-3"-carboxylic acid benzyl ester

| COMPOUND NAME | LCMS/$^1$H NMR |
|---|---|
| 2-(4-Fluorobenzyl)oxy-5-fluoro[1,1',2,2']terphenyl-3"-carboxylic acid 4-fluorobenzyl ester | CDCl$_3$ δ: 4.66(2H, br s), 5.23(2H, s), 6.60(1H, dd), 6.90-7.44(16H, m), 7.81(1H, s), 7.87(1H, dd) |
| 2-(2,4-Difluorobenzyl)oxy-5-fluoro[1,1',2,2']terphenyl-3"-carboxylic acid 2,4-difluorobenzyl ester | CDCl$_3$ δ: 4.65(2H, br s), 5.29(2H, s), 6.69-7.44(15H, m), 7.80(1H, s), 7.87(1H, dd) |

Example 82

2-Benzyloxy-5-fluoro[1,1',2,2']terphenyl-3"-carboxylic acid

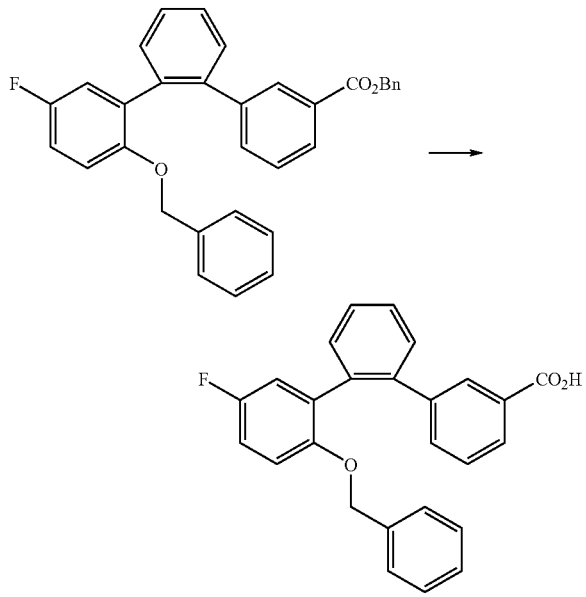

The compound was prepared by the standard hydrolysis procedure (General Procedure D). The residue was triturated with isohexane containing a trace of diethyl ether. The off-white solid was filtered and dried (87 mg).

$^1$H NMR (CDCl$_3$) δ 4.71(2H, br s), 6.66(1H, dd), 6.82-6.92 (2H, m), 7.01(2H, m), 7.22-7.46(9H, m), 7.91 (2H, m), LC/MS Rt=3.87 min [M–H] 433

The following Examples 83 and 84 were prepared from the appropriate ester by standard hydrolysis (General Procedure D).

| EX-AM-PLE | COMPOUND NAME | LC/MS | $^1$H NMR |
|---|---|---|---|
| 83 | 2-(4-Fluorobenzyl)oxy-5-fluoro[1,1',2,2']terphenyl-3"-carboxylic acid | Rt = 3.89 min [M – H] 415 | CDCl$_3$ δ: 4.66(2H, br s), 6.66(1H, dd), 6.91-6.98(6H, m), 7.22-7.26(2H, m), 7.39-7.47(4H, m), 7.90-7.93(2H, m) |
| 84 | 2-(2,4-Difluorobenzyl)-oxy-5-fluoro[1,1',2,2']terphenyl-3"-carboxylic acid | Rt = 3.92 min [M – H] 433 | CDCl$_3$ δ: 4.65(2H, br s), 6.70-6.75(3H, m), 6.88-6.95(3H, m), 7.23-7.26(2H, m), 7.38-7.46(4H, m), 7.88-7.93(2H, m) | preparation of Intermediates

3-Bromo-5-chloro-2-pyridinol

5-Chloro-2-pyridinol (5.18 g, 40 mmol) was dissolved in glacial acetic acid (50 ml) and bromine (7.51 g, 2.41 ml, 47 mmol) added. The mixture was stirred at room temperature for 48 hours. Ethyl acetate and water were added and the organic layer washed with water (×3), dried (MgSO$_4$) and evaporated. The residue was triturated with diethyl ether and the buff solid filtered and dried (5.59 g).

$^1$H NMR (CDCl$_3$) 7.52(1H, d J=3 Hz), 7.87(1H, d J=3 Hz).

2-(Benzyloxy)-3-bromo-5-chloropyridine

3-Bromo-5-chloro-2-pyridinol (7.0 g, 33.6 mmol) was stirred in toluene (160 ml) and silver carbonate (10.23 g, 36.9 mmol) added, followed by benzyl bromide (6.32 g, 4.39 ml, 36.9 mmol). The mixture was heated to reflux for 1 hour. After cooling, the mixture was filtered, washed with water (×2), dried (MgSO$_4$) and evaporated. The residue was triturated with isohexane and the pale yellow solid filtered and dried. (8.36 g).

$^1$H NMR (CDCl$_3$) 5.43(2H, s), 7.32-7.48(5H, m), 7.82(1H, d J=2 Hz), 8.04(1H, d J=2 Hz).

3-(2-Bromophenyl)-5-chloro-2-(benzyloxy)pyridine 2-(Benzyloxy)-3-bromo-5-chloropyridine (150 mg, 0.5 mmol) and 2-bromophenylboronic acid (100 mg, 0.5 mmol) were dissolved in toluene/ethanol (1:1, 5 ml) under nitrogen. Potassium carbonate (550 mg, 4 mmol) was added, followed by tetrakis(triphenylphosphine)palladium(0) (58 mg, 0.05 mmol). The resulting mixture was heated at 70° C. in a Smithcreator® microwave for 10 minutes. After cooling, diethyl ether(10 ml) and water (10 ml) were added, The organic layer was washed with water, dried (MgSO$_4$) and evaporated. The product was purified by flash chromatography (silica gel, 2% ethyl acetate:isohexane) to give the title compound as a clear oil (80 mg).

LC/MS Rt=4.14 min [M+H] 376

2'-{5-Chloro-2-(benzyloxy)-3-pyridinyl]-3-biphenyl-carboxylic acid ethyl ester

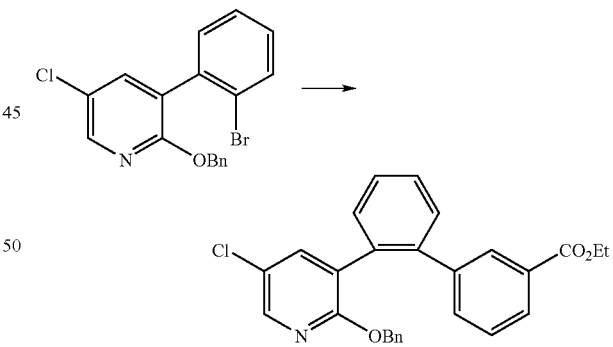

3-(2-Bromophenyl)-5-chloro-2-(benzyloxy)pyridine (80 mg, 0.214 mmol) and 3-(carbethoxy)phenylboronic acid (42 mg, 0.214 mmol) were dissolved in toluene/ethanol (1:1 1 ml) under nitrogen. Potassium carbonate (236 mg, 1.71 mmol) and tetrakis(triphenylphosphine)palladium(0) (25 mg, 0.0214 mmol) were added and the resulting mixture was heated at 70° C. in a Smithoreator® microwave for 15 minutes. After cooling, diethyl ether (5 ml) and water (5 ml) were added. The organic layer was washed with water, dried (MgSO$_4$) and evaporated. The product was purified by flash chromatography (silica gel, 2-3% ethyl acetate:isohexane) to give the title compound as a clear oil (31 mg).

¹H NMR (CDCl₃) 1.34(3H, t J=4.5 Hz) 4.29 (2H, q J=4.5 Hz), 5.01 (2H, br s), 7.09(2H, m), 7.18-7.26(5H, m), 7.37(1H, m), 7.42-7.46(4H, m), 7.81(1H, s), 7.87(1H, m), 8.00(1H, d J=2 Hz).

Example 85

2-{5-Chloro-2-benzyloxy)-3-pyridinyl]-3-biphenyl-carboxylic acid

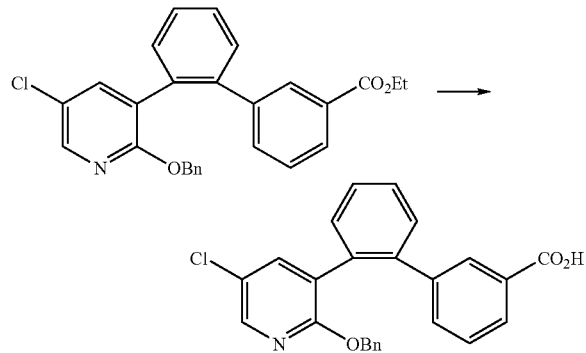

The compound was prepared by the standard hydrolysis procedure. The residue was triturated with isohexane. The off-white solid was filtered and dried (8.4 mg).

¹H NMR (CDCl₃) δ 5.03(2H, br s), 7.11(2H, m), 7.21-7.26 (5H, m), 7.37(1H, m), 7.44-7.47(4H, m), 7.89(1H, s), 7.91 (1H, m), 8.01(1H, d J=2 Hz). LC/MS R$_f$=4.00 min [M+H] 416.

Preparation of Intermediates

6-Chloro-2-iodo-3-pyridinol

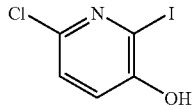

6-Chloro-3-pyridinol (2.0 g, 15.44 mmol) was stirred in water (40 ml) containing sodium carbonate (3.43 g, 32.36 mmol) and iodine (3.92 g, 15.44 mmol) was added. The mixture was stirred at room temperature for 72 hours. The pH was adjusted to pH8 with 1M hydrochloric acid solution and the mixture extracted with ethyl acetate (×2). The combined organic extracts were washed with brine and dried (MgSO₄). The aqueous layer was acidified to pH5 with 1M hydrochloric acid solution and extracted with ethyl acetate, which was washed with brine, dried (MgSO₄) and the combined solutions evaporated to leave the title compound as a buff solid (3.70 g).

¹H NMR (CDCl₃) δ: 7.18 (1H, d, J=2.5 Hz), 7.31 (1H, d, J=2.5 Hz), 9.53 (1H, br s).

6-Chloro-2-iodo-3-[(phenylmethyl)oxy]pyridine

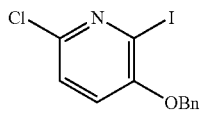

6-Chloro-2-iodo-3-pyridinol (1.28 g, 5 mmol) and silver carbonate (1.52 g, 5.5 mmol) were dissolved in toluene (25 ml) and benzyl bromide (654 μl, 5.5 mmol) added. The mixture was heated to reflux under nitrogen for 1 hour. After cooling, the mixture was filtered, washed with water (×2), dried (MgSO₄) and evaporated to an orange oil which was flash chromatographed eluting with 5% ethyl acetate in isohexane to give the title compound as an oil which crystallised on standing. LC/MS t=3.70, [MH⁺] 346, 348.

2-(2-Bromophenyl)-6-chloro-3-[(phenylmethyl)oxy] pyridine

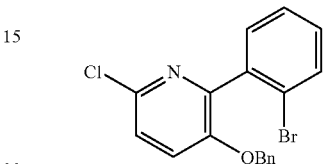

6-Chloro-2-iodo-3-[(phenylmethyl)oxy]pyridine (346 mg, 1 mmol) and 2-bromophenylboronic acid (201 mg, 1 mmol) were dissolved in 1:1 toluene/ethanol (10 ml) and potassium carbonate (1.1 g, 8 mmol) and tetrakis(triphenylphosphine)palladium(0) (116 mg, 0.1 mmol) added. The mixture was stirred under nitrogen and heated at 90° C. for 2 hours. After cooling, diethyl ether and water were added and the organic layer washed with water, dried (MgSO₄) and evaporated. The yellow oil was flash chromatographed, eluting with 2-10% ethyl acetate/isohexane to give the title compound as a clear oil (308 mg) LC/MS t=3.77, [MH+] 376, 378.

The following intermediates were prepared from the appropriate precursors using a similar route to that used for the preparation of 2'-{5-Chloro-2-(benzyloxy)-3-pyridinyl]-3-biphenylcarboxylic acid ethyl ester

| COMPOUND NAME | LCMS |
|---|---|
| Ethyl 2'-{6-chloro-3-[(phenylmethyl)oxy]-2-pyridinyl}-3-biphenylcarboxylate | Rt = 3.97 [MH⁺] 444, 446 |
| Methyl 5-amino-2'-{6-chloro-3-[(phenylmethyl)oxy]-2-pyridinyl}-3-biphenylcarboxylate | Rt = 3.61 [MH⁺] 445, 447 |

The following Examples 86 and 87 were prepared from the appropriate ester by standard hydrolysis (General Procedure D).

| EXAMPLE | COMPOUND NAME | LC/MS | ¹H NMR |
|---|---|---|---|
| 86 | 2'-{6-Chloro-3-[(phenylmethyl)oxy]-2-pyridinyl}-3-biphenylcarboxylic acid | Rt = 3.68 [MH⁺] 416, 418 | CDCl₃: 4.61(2H, s), 6.91-6.93(3H, m), 7.12(1H, d, J=3Hz), 7.23-7.26(5H, m), 7.43-7.57(4H, m), 7.93-7.94(2H, m) |
| 87 | 5-Amino-2'{6-chloro-3-[(phenylmethyl)oxy]-2-pyridinyl}-3-biphenylcarboxylic acid | Rt = 3.38 [MH⁺]431, 433 | CDCl₃: 4.67(2H, s), 6.59(1H, s), 6.95-6.97(3H, m), 7.11-7.12(1H, d, J=3Hz), 7.24-7.30(5H, m), 7.40-7.53(4H, m) |

Example 88

5-{2'-[(Phenylmethyl)oxy]-2-biphenylyl}-3-pyridinecarboxylic acid a) Ethyl 5-{2'-[(phenylmethyl)oxy]-2-biphenylyl}-3-pyridinecarboxylate

A mixture of ethyl 5-bromonicotinate (46 mg, 0.2 mmol), {2'-[(phenylmethyl)oxy]-2-biphenylyl}boronic acid (61 mg, 0.2 mmol), potassium carbonate (221 mg, 1.6 mmol) and tetrakis(triphenylphosphine)palladium(0) (23 mg, 0.02 mmol) was stirred and heated at 90° C. under nitrogen for 2 hours. After cooling the mixture was diluted with ether/water and the organic phase dried (magnesium sulphate), evaporated and chromatographed on silica eluting with ethyl acetate/iso-hexane (1:5) to give 66 mg of colourless gum.
LC/MS t=3.84, [MH+] 410.2.

b) 5-{2'-[(Phenylmethyl)oxy]-2-biphenylyl}-3-pyridinecarboxylic acid

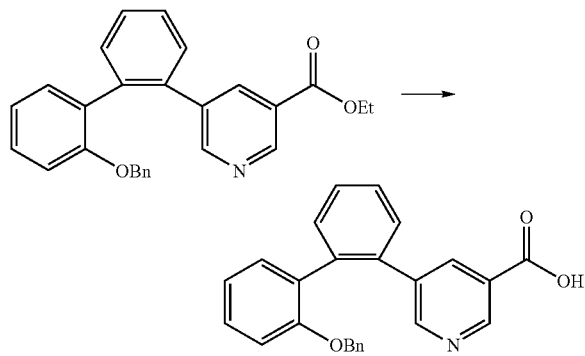

Prepared from ethyl 5-{2'-[(phenylmethyl)oxy]-2-biphenylyl}-3-pyridinecarboxylate using the standard hydrolysis procedure.
LC/MS t=3.60, [MH+] 382.2.

Example 89

4"-Chloro-2"-[(phenylmethyl)oxy]-1,1':2',1"-terphenyl-2-carboxylic acid a) 1-Bromo-4-chloro-2-[(phenylmethyl)oxy]benzene

A mixture of 2-bromo-5-chlorophenol (3.93 g, 18.94 mmol), benzyl bromide (3.42 g, 20 mmol) and potassium carbonate (10 g, 72.46 mmol) in acetone (80 ml) was stirred and refluxed for 3 hours then cooled, evaporated and dissolved in ether/water. The organic phase was dried (magnesium sulphate) evaporated and purified by chromatography on silica eluting with ethyl acetate/iso-hexane (1:99) to give 5.51 g of white solid.
$^1$HNMR (CDCl$_3$) δ: 5.13 (2H, s), 6.84 (1H, dd, J=8 Hz, 2 Hz), 6.93 (1H, d, J=2 Hz), 7.34-7.48 (6H, m).

b) {4-Chloro-2-[(phenylmethyl)oxy]phenyl}boronic acid 1-bromo-4-chloro-2-[(phenylmethyl)oxy]benzene (2.976 g, 10 mmol) in dry tetrahydrofuran (40 ml) was cooled to −100° C. n-Butyl lithium, 1.6M solution in hexanes (6.9 ml, 11 mmol) was added dropwise over 10 min under nitrogen. The reaction mixture was then allowed to warm to −70° C. for 1 h. Triisopropylborate (5.514, 30 mmol) was added dropwise under nitrogen. The cooling bath was then removed and the reaction mixture was allowed to warm to room temperature before being quenched with 2N hydrochloric acid (30 mL) and stirred vigorously at room temperature for 1 h. The product was then extracted with ether, dried over magnesium sulphate and evaporated down to an oil which was dissolved in iso-hexane and the solid which separated out was filtered off and dried. Yield 1.89 g.
$^1$H NMR (CDCl$_3$) δ: 5.11 (2H, s), 5.79 (2H, s), 6.99 (1H, d, J=2 Hz), 7.04 (1H, dd, J=8 Hz, 2 Hz), 7.37-7.43 (5H, m), 7.79 (1H, d, J=8 Hz).

c) Ethyl 4"-chloro-2"-[(phenylmethyl)oxy]-1,1':2',1"-terphenyl-2-carboxylate A mixture of ethyl 2'-bromo-2-biphenylcarboxylate (153 mg, 0.5 mmol), {4-chloro-2-[(phenylmethyl)oxy]phenyl}boronic acid (144 mg, 0.55 mmol), potassium carbonate (552 mg, 4 mmol) and tetrakis(triphenylphosphine) palladium(0) (58 mg, 0.05 mmol) was stirred and heated at 90° C. under nitrogen for 18 hours. After cooling the mixture was diluted with ether/water and the organic phase dried (magnesium sulphate), evaporated and chromatographed on silica eluting with ethyl acetate/iso-hexane (1:19) to give 104 mg of colourless gum.
$^1$H NMR (CDCl$_3$) δ: 0.95 (3H, br s), 3.98 (2H, br s), 4.87 (2H, q,), 6.74 (1H, dd, J=8 Hz, 2 Hz), 6.77 (1H, d, J=2 Hz), 6.89-7.05 (2H, m), 7.18-7.39 (11H, m), 7.71 (1H, m).

d) 4"-Chloro-2"-[(phenylmethyl)oxy]-1,1':2',1"-terphenyl-2-carboxylic acid

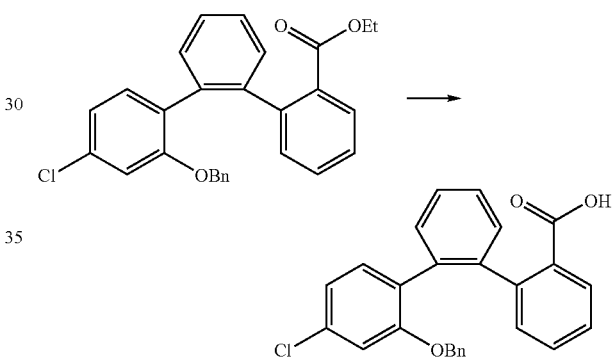

The title compound was prepared from ethyl 4"-chloro-2"-[(phenylmethyl)oxy]-1,1':2',1"-terphenyl-2-carboxylate using the standard hydrolysis procedure.
LC/MS t=3.60, [MH−] 413.1, 415.1

Example 90

6"Fluoro-2-benzyloxy-[1,1':2',1"]terphenyl-3"-carboxylic acid

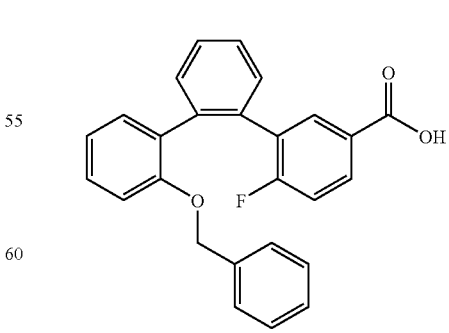

{2'-[(phenylmethyl)oxy]-2-biphenylyl}boronic acid (60 mg, 0.19 mmol) and 3-bromo-4-fluorobenzoic acid (69 mg, 0.31 mmol) were dissolved in 1:1 toluene:ethanol (6 ml)

under nitrogen. Potassium carbonate (290 mg, 2.1 mmol) and tetrakis(triphenylphosphine)palladium(0) (23 mg, 0.019 mmol) were added and the mixture heated at 90° C. for 1 h. After cooling, the reaction mixture was poured into water, acidified with 1M HCl solution and extracted with ethyl acetate (15×2 ml), the combined organic layer were dried and evaporated. The residue was then purified on an SPE column using 40% of ethyl acetate in iso-hexane to give the title compound as white solid.

LC/MS t=3.84, [MH–] 397, 398

It is to be understood that the present invention covers all combinations of particular and preferred subgroups described herein above.

Assays for Determining Biological Activity

The compounds of formula (I) can be tested using the following assays to demonstrate their prostanoid antagonist or agonist activity in vitro and in vivo and their selectivity. The prostaglandin receptors investigated are DP, $EP_1$, $EP_2$, $EP_3$, $EP_4$, FP, IP and TP.

The ability of compounds to antagonise $EP_1$ & $EP_3$ receptors may be demonstrated using a functional calcium mobilisation assay. Briefly, the antagonist properties of compounds are assessed by their ability to inhibit the mobilisation of intracellular calcium ($[Ca^{2+}]_i$) in response to activation of $EP_1$ or $EP_3$ receptors by the natural agonist hormone prostaglandin $E_2$ ($PGE_2$). Increasing concentrations of antagonist reduce the amount of calcium that a given concentration of $PGE_2$ can mobilise. The net effect is to displace the $PGE_2$ concentration-effect curve to higher concentrations of $PGE_2$. The amount of calcium produced is assessed using a calcium-sensitive fluorescent dye such as Fluo-3, AM and a suitable instrument such as a Fluorimetric Imaging Plate Reader (FLIPR). Increasing amounts of $[Ca^{2+}]_i$ produced by receptor activation increase the amount of fluorescence produced by the dye and give rise to an increasing signal. The signal may be detected using the FLIPR instrument and the data generated may be analysed with suitable curve-fitting software.

The human $EP_1$ or $EP_3$ calcium mobilisation assay (hereafter referred to as 'the calcium assay') utilises Chinese hamster ovary-K1 (CHO-K1) cells into which a stable vector containing either $EP_1$ or $EP_3$ cDNA has previously been transfected. Cells are cultured in suitable flasks containing culture medium such as DMEM:F-12 supplemented with 10% v/v foetal calf serum, 2 mM L-glutamine, 0.25 mg/ml geneticin and 10 μg/ml puromycin.

For assay, cells are harvested using a proprietary reagent that dislodges cells such as Versene. Cells are re-suspended in a suitable quantity of fresh culture media for introduction into a 384-well plate. Following incubation for 24 hours at 37° C. the culture media is replaced with a medium containing fluo-3 and the detergent pluronic acid, and a further incubation takes place. Concentrations of compounds are then added to the plate in order to construct concentration-effect curves. This may be performed on the FLIPR in order to assess the agonist properties of the compounds. Concentrations of $PGE_2$ are then added to the plate in order to assess the antagonist properties of the compounds.

The data so generated may be analysed by means of a computerised curve-fitting routine. The concentration of compound that elicits a half-maximal inhibition of the calcium mobilisation induced by $PGE_2$ ($pIC_{50}$) may then be estimated.

Binding Assay for the Human Prostanoid $EP_1$ Receptor

Competition assay using [³H]-PGE2.

Compound potencies are determined-using a radioligand binding assay. In this assay compound potencies are determined from their ability to compete with tritiated prostaglandin $E_2$ ([³H]-$PGE_2$) for binding to the human $EP_1$ receptor.

This assay utilises Chinese hamster ovary-K1 (CHO-K1) cells into which a stable vector containing the $EP_1$ cDNA has previously been transfected. Cells are cultured in suitable flasks containing culture medium such as DMEM:F-12 supplemented with 10% v/v foetal calf serum, 2 mM L-glutamine, 0.25 mg/ml geneticin, 10 μg/ml puromycin and 10 μM indomethacin.

Cells are detached from the culture flasks by incubation in calcium and magnesium free phosphate buffered saline containing 1 mM disodium ethylenediaminetetraacetic acid ($Na_2EDTA$) and 10 μM indomethacin for 5 min. The cells are isolated by centrifugation at 250×g for 5 mins and suspended in an ice cold buffer such as 50 mM Tris, 1 mM $Na_2EDTA$, 140 mM NaCl, 10 μM indomethacin (pH 7.4). The cells are homogenised using a Polytron tissue disrupter (2×10 s burst at full setting), centrifuged at 48,000×g for 20 mins and the pellet containing the membrane fraction is washed three times by suspension and centrifugation at 48,000×g for 20 mins. The final membrane pellet is suspended in an assay buffer such as 10 mM 2-[N-morpholino]ethanesulphonic acid, 1 mM $Na_2EDTA$, 10 mM $MgCl_2$ (pH 6). Aliquots are frozen at −80° C. until required.

For the binding assay the cell membranes, competing compounds and [³H]-$PGE_2$ (3 nM final assay concentration) are incubated in a final volume of 100 μl for 30 min at 30° C. All reagents are prepared in assay buffer. Reactions are terminated by rapid vacuum filtration over GF/B filters using a Brandell cell harvester. The filters are washed with ice cold assay buffer, dried and the radioactivity retained on the filters is measured by liquid scintillation counting in Packard TopCount scintillation counter.

The data are analysed using non linear curve fitting techniques (GraphPad Prism 3) to determine the concentration of compound producing 50% inhibition of specific binding ($IC_{50}$).

By application of these techniques, compounds of the Examples had an antagonist $pIC_{50}$ value of 6.0 to 9.0 at $EP_1$ receptors and $pIC_{50}$ value of <6.0 at $EP_3$ receptors.

No toxicological effects are indicated/expected when a compound (of the invention) is administered in the above mentioned dosage range.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims:

The invention claimed is:

1. A compound of formula (I):

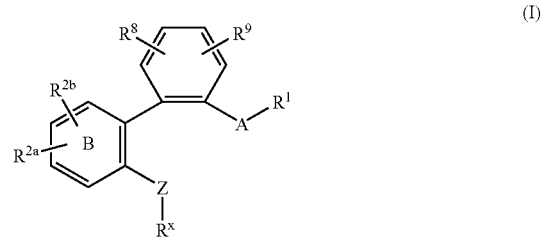

wherein:
A is an optionally substituted aryl, or an optionally substituted 5- or 6-membered heterocyclyl ring, or an optionally substituted bicyclic heterocyclyl group;
B is a phenyl or pyridyl ring;
Z is O, S, SO, or $SO_2$;
$R^1$ is $CO_2R^4$, CN, $CONR^5R^6$, $CH_2CO_2R^4$, optionally substituted alkyl, optionally substituted alkenyl, optionally substituted $SO_2$alkyl, $SO_2NR^5R^6$, $NR^5CONR^5R^6$, COalkyl, 2H-tetrazol-5-yl-methyl, optionally substituted bicyclic heterocycle or optionally substituted heterocyclyl;
$R^{2a}$ and $R^{2b}$ independently are hydrogen, halogen, optionally substituted alkyl, optionally substituted alkoxy, CN, $SO_2$alkyl, $SR^5$, $NO_2$, optionally substituted aryl, $CONR^5R^6$ or optionally substituted heteroaryl;
$R^x$ is optionally substituted $CQ^aQ^b$-heterocyclyl optionally substituted $CQ^aQ^b$-bicyclic heterocyclyl or optionally substituted $CQ^aQ^b$-aryl;
$R^4$ is hydrogen or an optionally substituted alkyl;
$R^5$ is hydrogen or an optionally substituted alkyl;
$R^6$ is hydrogen or optionally substituted alkyl, optionally substituted heteroaryl, optionally substituted $SO_2$aryl, optionally substituted $SO_2$alkyl, optionally substituted $SO_2$heteroaryl, CN, optionally substituted $CQ^aQ^b$aryl, optionally substituted $CQ^aQ^b$heteroaryl or $COR^7$;
$R^7$ is hydrogen, optionally substituted alkyl, optionally substituted heteroaryl or optionally substituted aryl;
$R^8$ and $R^9$ independently are hydrogen, chloro, fluoro, $CF_3$, $C_{1-3}$alkoxy or $C_{1-3}$alkyl;
$Q^a$ and $Q^b$ are independently selected from hydrogen and $CH_3$;
wherein when A is a 6-membered ring the $R^1$ substituent and phenyl ring are attached to carbon atoms 1,2-, 1,3- or 1,4-relative to each other, and when A is a five-membered ring or bicyclic heterocyclyl group the $R^1$ substituent and phenyl ring are attached to substitutable carbon atoms 1,2- or 1,3-relative to each other;
and
provided that the corn pound is not 2-benzyloxy[1,1';2',1"] terphenyl-4"-carboxylic acid; or a pharmaceutically acceptable salt thereof.

2. A compound according to claim 1 wherein when A is a 6-membered ring, the $R^1$ substituent and phenyl ring are attached to carbon atoms 1,2-, or 1,3-relative to each other.

3. A compound according to claim 1 wherein A is phenyl, pyridyl, or pyrazinyl.

4. A compound of formula (Ia):

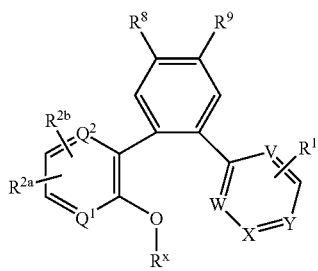

(Ia)

wherein:
W, X, and Y each are $CR^{12}$ or N;
V is $CR^1$, $CR^{12}$ or N;
wherein at least two of W, X, Y or V is $CR^{12}$; and $R^{12}$ is independently selected from hydrogen, halogen, CN, optionally substituted $CO_2C_{1-6}$alkyl, $CONR^5R^6$, $NR^5R^6$, optionally substituted $NR^5COC_{1-6}$alkyl, optionally substituted $NR^5CO$phenyl, optionally substituted $NR^5CO$piperidinyl, optionally substituted $NR^5CO$heterocyclyl, optionally substituted $NR^5SO_2C_{1-6}$alkyl, OH, optionally substituted $OC_{1-6}$alkyl, optionally substituted $C_{1-6}$alkyl and $NR^{10}R^{11}$;
$Q^1$ and $Q^2$ each is CH, or one of $Q^1$ and $Q^2$ is N and the other is CH;
$R^1$ is $CO_2H$, optionally substituted $CONHSO_2$aryl, $CH_2CO_2H$, $SO_2NHCOR^7$, $SO_2NHCOC_{1-6}$alkyl or tetrazolyl and is positioned 1,2-, or 1,3-relative to the phenyl ring;
$R^{2a}$ and $R^{2b}$ are independently selected from hydrogen, halo, and $CF_3$;
$R^x$ is optionally substituted $CQ^aQ^b$-heterocyclyl or optionally substituted $CQ^aQ^b$-phenyl wherein $Q^a$ and $Q^b$ are independently selected from hydrogen and $CH_3$;
$R^4$ hydrogen or an optionally substituted $C_{1-6}$alkyl;
$R^5$ is hydrogen or an optionally substituted $C_{1-6}$alkyl;
$R^6$ is hydrogen or an optionally substituted $C_{1-6}$alkyl, optionally substituted $SO_2$phenyl, optionally substituted $SO_2$heterocyclyl group, CN, optionally substituted $CH_2$phenyl or $COR^7$;
$R^7$ is hydrogen, optionally substituted heteroaryl or optionally substituted phenyl;
$R^8$ and $R^9$ independently represent hydrogen, chloro, fluoro, $CF_3$, $C_{1-3}$alkoxy or $C_{1-3}$alkyl; and
$R^{10}$ and $R^{11}$ together with the nitrogen atom to which they are attached form a morpholine ring, a 5- or 6-membered lactam ring or a 5- or 6-membered cyclic sulphonamide;
or a pharmaceutically acceptable salt thereof.

5. A compound according to claim 1 wherein $R^x$ is optionally substituted $C_{1-8}$alkyl, optionally substituted $CH_2$phenyl, $CH_2$pyridyl, or $CH_2$thienyl.

6. A compound according to claim 1 wherein $R^{2b}$ is positioned 1,4-relative to the Z substituent and 1,3-relative to the phenyl ring.

7. A compound selected from the group consisting of:
2-benzyloxy-5-chloro-[1,1';2',1"]terphenyl-3"-carboxylic acid;
(2-benzyloxy-5-chloro-[1,1';2',1"]terphenyl-3"-yl)-acetic acid;
(2-benzyyloxy-5-chloro[1,1';2',1"]terphenyl-2"-yl)acetic acid;
(2-benzyloxy-5-chloro[1,1';2',1"]terphenyl-4"-yl)acetic acid;
5"-acetylamino-2-benzyloxy-5-chloro[1,1';2',1"]terphenyl-3"-carboxylic acid;
2-benzyloxy-5-chloro-5"-propionylamino[1,1';2',1"]terphenyl-3"-carboxylic acid;
2-benzyloxy-5-chloro-5"-(2-methylpropanoylamino)-[1,1';2',1"]terphenyl-3"-carboxylic acid;
2-benzoyloxy-5"-butyrylamino-5-chloro[1,1';2',1"]terphenyl-3"-carboxylic acid;
2-benzyloxy-5-chloro-5"-[(1-phenyl-methanoyl)amino]-[1,1';2',1"]terphenyl-3"-carboxylic acid;
2-benzyloxy-5-chloro-5"-methanesulfonylamino-[1,1';2',1"]terphenyl-3"-carboxylic acid;
5"-amino-2-benzyloxy-5-chloro[1,1';2',2"]-3"-carboxylic acid;
2-benzyloxy-5"-butyrylamino-5-trifluoromethyl[1,1';2',1"]terphenyl-3"-carboxylic acid-3-carboxylic acid;
2-benzyloxy-4"-chloro[1,1';2',1"]terphenyl 2-carboxylic acid;
2-benzyloxy-5"-fluoro-[1,1';2',1"]terphenyl-2"-carboxylic acid;

2-benzyloxy-4"-fluoro-[1,1';2',1"]terphenyl-2"-carboxylic acid;
2"-benzyloxy-5-fluoro-[1,1';2',1"]terphenyl-3-carboxylic acid;
4"-amino-2-benzyloxy-[1,1';2',1"]terphenyl-3"-carboxylic acid; 5"-acetylamino-2-benzyloxy-[1,1';2',1"]terphenyl-2"-carboxylic acid;
2-benzyloxy-5-chloro-[1,1';2',1"]terphenyl-2"-carboxylic acid;
2-benzyloxy-[1,1';2',1"]terphenyl-3"-carboxylic acid;
2-benzyloxy-5-chloro-[1,1';2',1"]terphenyl-2"-carboxylic acid amide;
5-(2-benzyloxy-5-chloro-[1,1';2',1"]terphenyl-3"-yl)-1H-tetrazole;
N-[1-(2-benzyloxy-5-chloro-[1,1';2',1"]terphenyl-2"-yl)-methanoyl]-benzenesulfonamide;
2-benzyloxy-[1,1';2',1"]terphenyl-4"-sulfonic acid (1-phenyl-methanoyl)-amide;
2-benzyloxy-[1,1';2',1"]terphenyl-4"-sulfonic acid [1-(4-nitro-phenyl)-methanoy]-amide;
2-benzyloxy-[1,1';2',1"]terphenyl-3"-sulfonic acid acetylamide;
5-chloro-2-(4-fluoro-benzyloxy-[1,1';2',1"]terphenyl-3"-carboxylic acid;
5-chloro-2-(2,4-difluoro-benzyloxy)-[1,1';2',1"]terphenyl-3"-carboxylic acid;
5-chloro-2-(4-chloro-benzyloxy)-[1,1';2',1"]terphenyl-3"carboxylic acid;
5-chloro-2-(2-fluoro-4-chloro-benzyloxy)-[1,1';2',1"]terphenyl-3"carboxylic;
5-chloro-2-(pyridin-2-ylmethoxy)-[1,1';2',1"]terphenyl-3"carboxylic acid;
5-chloro-2-(pyridin-4-ylmethoxy)-[1,1';2',1"]terphenyl-3"carboxylic acid;
5-chloro-2-(pyridin-3-ylmethoxy)-[1,1';2',1"]terphenyl-3"carboxylic acid;
5-chloro-2-cyclohexylmethoxy-[1,1';2',1"]terphenyl-3"carboxylic acid;
5-chloro-2-(thiophen-3-ylmethoxy)-[1,1';2',1"]terphenyl-3"carboxylic acid;
5-chloro-2-(thiophen-2-ylmethoxy)-[1,1';2',1"]terphenyl-3"carboxylic acid;
5-chloro-2-cyclopentylmethoxy-[1,1';2',1"]terphenyl-3"carboxylic acid;
2"-{[(4-Fluorophenyl)methyl]oxy}-5-[(methyloxy)carbonyl]-5"-(trifluoromethyl)-1,1':2',1"-terphenyl-3-carboxylic acid;
5-Chloro-2"-[(phenylmethyl)oxy]-1,1':2',1"-terphenyl-2-carboxylic acid;
4-(methoxy)-2"-[(phenylmethyl)oxy]-1,1':2',1"-terphenyl-2-carboxylic acid;
2"-{[(2,4-Difluorophenyl)methyl]oxy}-4-(propanoylamino)-5"-(trifluoromethyl)-1,1':2',1"-terphenyl-2-carboxylic acid;
2"-{[(2,4-Difluorophenyl)methyl]oxy}-4-[(2-methylpropanoyl)amino]-5"-(trifluoromethyl)-1,1':2',1"-terphenyl-2-carboxylic acid;
5-(2-Oxy-1-pyrrolidinyl)-2"-[(phenylmethyl)oxy]-5"-(trifluoromethyl-1,1':2',1"-terphenyl-3-carboxylic acid;
2"-{[(4-Fluorophenyl)methyl]oxy}-5"-(trifluoromethyl)-1,1':2',1"-terphenyl-3,5-dicarboxylic acid;
2"-{[(4-Fluorophenyl)methyl]oxy}-5-{[(2-methylpropyl)amino]carbonyl}-5"-(trifluoromethyl)-1,1':2',1"-terphenyl-3-carboxylic acid;
6-[2'-{[(4-Fluorophenyl)methyl]oxy}-5'-(trifluoromethyl)-2-biphenylyl]-2-pyrazinecarboxylic acid;
2"-{[(4-Fluorophenyl)methyl]oxy}-5-(propanoylamino)-5"-(trifluoromethyl)-1,1':2',1"-terphenyl-3-carboxylic acid;
2"-[(Phenylmethyl)oxy]-5-(propanoylamino)-5"-(trifluoromethyl)-1,1':2',1"-terphenyl-3-carboxylic acid;
2"-{[(2,4-Difluorophenyl)methyl]oxy}-5-(propanoylamino)-5"-(trifluoromethyl)-1,1':2',1"-terphenyl-3-carboxylic acid;
5"-Chloro-5-{[(methyloxy)acetyl]amino}-2"-[(phenylmethyl)oxy]-1,1':2',1"-terphenyl-3-carboxylic acid;
5"-Chloro-2"-[(phenylmethyl)oxy]-5-[(2-thienylacetyl)amino]-1,1':2',1"-terphenyl-3-carboxylic acid;
5"-Chloro-2"-[(phenylmethyl)oxy]-5-({[(phenylmethyl)oxy]acetyl}amino)-1,1':2',1"-terphenyl-3-carboxylic acid;
5-{[(1-Acetyl-4-piperidinyl)carbonyl]amino}-5"-chloro-2"-[(phenylmethyl)oxy]-1,1':2',1"-terphenyl-3-carboxylic acid;
5"-Chloro-5-[(phenylacetyl)amino]-2"-[(phenylmethyl)oxy]-1,1':2',1"-terphenyl-3-carboxylic acid;
5"-Chloro-5-{[(3,5-dimethyl-4-isoxazoly)carbonyl]amino}-2"-[(phenylmethyl)oxy]-1,1':2',1"-terphenyl-3-carboxylic acid;
5"-Chloro-5-[(3-methylbutanoyl)amino]-2"-[(phenylmethyl)oxy]-1,1':2',1"-terphenyl-3-carboxylic acid;
5"-Chloro-5-(glycylamino)-2"-[(phenylmethyl)oxy]-1,1':2',1"-terphenyl-3-carboxylic acid;
2"-[(Phenylmethyl)oxy]-4-(propanoylamino)-1,1':2',1"-terphenyl-2-carboxylic acid;
4-[(2-Methylpropanoyl)amino]-2"-[(phenylmethyl)oxy]-1,1':2',1"-terphenyl-2-carboxylic acid;
5-Cyano-2"-{[(2,4-difluorophenyl)methyl]oxy}-5"-(trifluoromethyl)-1,1':2',1"-terphenyl-3-carboxylic acid;
5"-Bromo-5-cyano-2"-[(phenylmethyl)oxy]-1,1':2',1"-terphenyl-3-carboxylic acid;
5-Cyano-2"-[(phenylmethyl)oxy]-5"-(trifluoromethyl)-1,1':2',1"-terphenyl-3-carboxylic acid;
5-(Aminocarbonyl)-2"-{[(4-fluorophenyl)methyl]oxy}-5"-(trifluoromethyl)-1,1':2',1"-terphenyl-3-carboxylic acid;
2"-{[(4-Fluorophenyl)methyl]oxy}-5-{[(2-hydroxyethyl)amino]carbonyl}-5"-(trifluoromethyl)-1,1':2',1"-terphenyl-3-carboxylic acid;
2"-{[(4-Fluorophenyl)methyl]oxy}-5-{[(3-pyridinylmethyl)amino]carbonyl}-5"-(trifluoromethyl)-1,1':2',1"-terphenyl-3-carboxylic acid;
6-{5'-Chloro-2'-[(phenylmethyl)oxy]-2-biphenylyl}-2-pyridinecarboxylic acid;
6-(5'-Chloro-2'-{[(4-fluorophenyl)methyl]oxy}-2-biphenyly)-2-pryridinecarboxylic acid;
6-(5'-Chloro-2'-{[(2,4-difluorophenyl)methyl]oxy}-2-biphenylyl)-2-pyridinecarboxylic acid;
2-[2'-{[(4-Fluorophenyl)methyl]oxy}-5'-(trifluoromethyl)-2-biphenylyl]-4-pyridinecarboxylic acid;
3-Amino-6-[2'-{[(4-fluorophenyl)methyl]oxy}-5'-(trifluoromethyl)-2-biphenylyl]-2-pyrazinecarboxylic acid;
4-(Acetylamino)-2"-[(phenylmethyl)oxy]-5"-(trifluoromethyl)-1 ,1 ':2',1"-terphenyl-2-carboxylic acid;
4-(Acetylamino)-2"-{[(4-fluorophenyl)methyl]oxy}-5"-(trifluoromethyl)-1,1':2',1"-terphenyl-2-carboxylic acid;
4-(Acetylamino)-2"-{[(2,4-difluorophenyl)methyl]oxy}-5"-(trifluoromethyl)-1,1':2',1"-terphenyl-2-carboxylic acid;
4-Methyl-2"-[(phenylmethyl)oxy]-1,1':2',1"-terphenyl-2-carboxylic acid;

2"-{[(2,4-Difluorophenyl)methyl]oxy}-4-methyl-5"-(trifluoromethyl)-1,1':2',1"-terphenyl-2-carboxylic acid;
2-(4-Fluorobenzyl)oxy-5-fluoro[1,1',2,2']terphenyl-3"-carboxylic acid;
2-(2,4-Difluorobenzyl)oxy-5-fluoro[1,1',2,2']terphenyl-3"-carboxylic acid;
2'-{6-Chloro-3-[(phenylmethyl)oxy]-2-pyridinyl}-3-biphenylcarboxylic acid;
5-Amino-2'-{6-chloro-3-[(phenylmethyl)oxy]-2-pyridinyl}-3-biphenylcarboxylic acid;
4"-Chloro-2"-[(phenylmethyl)oxy]-1,1':2',1"-terphenyl-2-carboxylic acid; and
6"Fluoro-2-benzyloxy-[1,1';2',1"]terphenyl-3"-carboxylic acid; or a pharmaceutically acceptable salt thereof.

8. A pharmaceutical composition comprising a compound according to claim 1 together with a pharmaceutical carrier and/or excipient.

9. A process for the preparation of a compound of formula (I) as defined in claim 1 comprising:
reacting a compound of formula (IV):

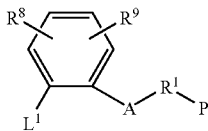

(IV)

wherein $R^8$, $R^9$, A, and $R^1$ are as hereinbefore defined above for a compound of formula (I), $L^1$ is a leaving group and P is an optional protecting group;
with a compound of formula (III):

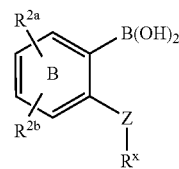

(III)

wherein $R^{2a}$, $R^{2b}$, B, Z, and $R^x$ are as hereinbefore defined above for a compound of formula (I);
and where required converting:
one group A to another group A, and/or
one group $R^x$ to another group $R^x$;
and where required carrying out the following optional steps in any order:
effecting deprotection; and/or
converting one group $R^1$ to another group $R^1$; and/or
forming a derivative of the compound of formula (I) so formed.

* * * * *